United States Patent
Okamoto et al.

(10) Patent No.: US 12,139,546 B2
(45) Date of Patent: Nov. 12, 2024

(54) METHODS OF TREATING UREA CYCLE DISORDERS BY INTERFERING WITH GLUCAGON RECEPTOR SIGNALING

(71) Applicant: Regeneron Pharmaceuticals, Inc., Tarrytown, NY (US)

(72) Inventors: Haruka Okamoto, New York, NY (US); Xiping Cheng, Northvale, NJ (US); Jesper Gromada, Concord, MA (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 802 days.

(21) Appl. No.: 16/640,907

(22) PCT Filed: Aug. 21, 2018

(86) PCT No.: PCT/US2018/047286
§ 371 (c)(1),
(2) Date: Feb. 21, 2020

(87) PCT Pub. No.: WO2019/040471
PCT Pub. Date: Feb. 28, 2019

(65) Prior Publication Data
US 2021/0130480 A1 May 6, 2021

Related U.S. Application Data

(60) Provisional application No. 62/548,632, filed on Aug. 22, 2017.

(51) Int. Cl.
*C07K 16/28* (2006.01)
*A61K 31/7088* (2006.01)
*A61K 45/06* (2006.01)

(52) U.S. Cl.
CPC ...... *C07K 16/2869* (2013.01); *A61K 31/7088* (2013.01); *A61K 45/06* (2013.01)

(58) Field of Classification Search
CPC ............ C07K 16/2869; A61K 31/7088; A61K 45/06; A61K 2039/505; A61P 3/00
See application file for complete search history.

(56) References Cited

U.S. PATENT DOCUMENTS

| | | | |
|---|---|---|---|
| 4,206,199 A | 6/1980 | Fujino et al. |
| 4,221,777 A | 9/1980 | Nishino |
| 4,272,433 A | 6/1981 | Nishino |
| 4,407,965 A | 10/1983 | Yanaihara |
| 4,423,034 A | 12/1983 | Nakagawa et al. |
| 4,816,567 A | 3/1989 | Cabilly et al. |
| 4,946,778 A | 8/1990 | Ladner et al. |
| 5,712,105 A | 1/1998 | Yanaihara et al. |
| 5,770,445 A | 6/1998 | Kindsvogel et al. |
| 7,947,809 B2 | 5/2011 | Yan et al. |
| 8,545,847 B2 | 10/2013 | Okamoto et al. |
| 2004/0101920 A1 | 5/2004 | Radziejewski et al. |
| 2009/0041784 A1 | 2/2009 | Yan et al. |
| 2009/0252727 A1 | 10/2009 | Korytko et al. |
| 2011/0223160 A1 | 9/2011 | Yan et al. |
| 2011/0306624 A1 | 12/2011 | Lin et al. |
| 2016/0075778 A1 | 3/2016 | Okamoto et al. |

FOREIGN PATENT DOCUMENTS

| | | |
|---|---|---|
| EP | 0658200 B1 | 12/2004 |
| EP | 2074149 B1 | 6/2013 |
| FR | 2959129 A1 * | 10/2011 |
| WO | WO2005065680 A1 | 7/2005 |
| WO | WO2005121097 A2 | 12/2005 |
| WO | WO2005123688 A2 | 12/2005 |
| WO | WO2006014618 A2 | 2/2006 |
| WO | WO2006017055 A2 | 2/2006 |
| WO | WO2006086488 A2 | 8/2006 |
| WO | WO2006102067 A1 | 9/2006 |
| WO | WO2006104826 A2 | 10/2006 |

(Continued)

OTHER PUBLICATIONS

Trevisani et al (Am J Gastroenterol 83: 646-51, 1988).*
Janecka et al (Pept Res 58: 91-107, 2001) (Abstract only).*
<Glycerol phenylbutyrate | C33H38O6 | ChemSpider> downloaded on Oct. 11, 2022, pp. 1-2.*
Hyperammonemia Wikipedia, downloaded < Hyperammonemia—Wikipedia>, on Oct. 10, 2022, pp. 1-4.*
Matoori et al (Adv Drug Del Rev 90: 55-68, 2015).*
Batshaw et al (J Pediatr 138: S46-S55, 2001).*

(Continued)

*Primary Examiner* — Kimberly Ballard
*Assistant Examiner* — Stacey N Macfarlane
(74) *Attorney, Agent, or Firm* — FisherBroyles, LLP; Cara L. Crowley-Weber; Trisha Agrawal

(57) ABSTRACT

Provided herein are methods of treating a subject with hyperammonemia or a urea cycle disorder. The methods comprise administering to a subject in need thereof a therapeutic amount of a glucagon signaling pathway inhibitor, such that ammonia levels are lowered or that amino acid metabolism enzymes are down-regulated, or a condition or disease characterized by hyperammonemia is mediated, or at least one symptom or complication associated with the condition or disease is alleviated or reduced in severity. The glucagon signaling pathway inhibitor can be a small molecule inhibitor of the signaling pathway, an antisense inhibitor of the signaling pathway, shRNA, siRNA, a GCG neutralizing monoclonal antibody, a GCGR antagonist, a peptide inhibitor of the signaling pathway, a DARPin, a Spiegelmer, an aptamer, engineered Fn type-III domains, etc. The therapeutic methods are useful for treating a human suffering from hyperammonemia or a urea cycle disorder.

18 Claims, 8 Drawing Sheets
Specification includes a Sequence Listing.

(56) References Cited

FOREIGN PATENT DOCUMENTS

| | | |
|---|---|---|
| WO | WO2007047676 A1 | 4/2007 |
| WO | WO2007124463 A1 | 11/2007 |
| WO | WO2008036341 A2 | 3/2008 |
| WO | WO2008042223 A1 | 4/2008 |
| WO | WO2008098244 A1 | 8/2008 |
| WO | WO2009140342 A1 | 11/2009 |
| WO | WO2010030722 A1 | 3/2010 |
| WO | WO2010071750 A1 | 6/2010 |
| WO | WO2010088061 A1 | 8/2010 |
| WO | WO2010098948 A1 | 9/2010 |
| WO | WO2010098994 A1 | 9/2010 |
| WO | WO2011007722 A1 | 1/2011 |
| WO | WO2012071372 A2 | 5/2012 |
| WO | WO2013048558 A2 | 4/2013 |
| WO | WO2013081993 A1 | 6/2013 |

OTHER PUBLICATIONS

Kostic et al. (2018) "A First-in-Human Pharmacodynamic and Pharmacokinetic Study of a Fully Human Anti-Glucagon Receptor Monoclonal Antibody in Normal Healthy Volunteers", Diabetes Obes Metab., 20:283-291.
Okamoto et al. (2017) "Glucagon Receptor Inhibition Normalizes Blood Glucose in Sever Insulin-Resistant Mice", PNAS, 114(10):2753-2758.
Okamoto et al. (2015) "Glucagon Receptor Blockade with a Human Antibody Normalizes Blood Glucose in Diabetic Mice and Monkeys", Endocrinology, 156(8):2781-2794.
Al-Lazikani et al. (1997) "Standard Conformations for the Canonical Structures of Immunoglobulins" J. Mol. Biol. 273:927-948.
Almdal, et al. (1992) "Glucagon Immunoneutralization in Diabetic Rats Normalizes Urea Synthesis and Decreases Nitrogen Wasting" Diabetes, 41:12-16.
Burcelin et al. (1995) "Cloning and Sequence Analysis of the Murine Glucagon Receptor-Encoding Gene" Gene 164(2):305-310.
De Laszlo et al. (1999) "Potent, Orally Absorbed Glucagon Receptor Antagonists" Bioorg. Med. Chem. Lett. 9:641-646.
Häberle (2013) "Clinical and Biochemical Aspects of Primary and Secondary Hyperammonemic Disorders" Archives of Biochemistry and Biophysics 536(2):101-108.
International Search Report from PCT/US2018/047286 dated Jan. 2, 2019, 16 pages.
Kabadi et al. (1985) "Elevated Plasma Ammonia Level in Hepatic Cirrhosis: Role of Glucagon" Gastroenterology, 88(3):750-756.
Kabat (1991) "Sequences of Proteins of Immunological Interest," National Institutes of Health, Bethesda, Md.
Kohler et al. (1975) "Continuous Cultures of Fused Cells Secreting Antibody of Predefined Specificity" Nature 256:495-497.
Kufer et al. (2004) "A Revival of Bispecific Antibodies" Trends Biotechnol. 22:238-244.
Langer (1990) "New Methods of Drug Delivery" Science 249:1527-1533.
Lloyd (1999) "The Art, Science and Technology of Pharmaceutical Compounding" American Pharmacists Association.
Martin et al. (1989) "Modeling Antibody Hypervariable Loops: A Combined Algorithm" Proc Natl Acad Sci 86:9268-9272.
McCafferty et al. (1990) "Phage Antibodies: Filamentous Phage Displaying Antibody Variable Domains" Nature 348:552-554.
McNally et al. (2004) "Cloning and Characterization of the Glucagon Receptor from Cynomologous Monkey" Peptides 25:1171-1178.
Powell et al. (1998) "Compendium of excipients for parenteral formulations" PDA J Pharm Sci Technol 52:238-311.
Tutt et al. (1991) "Trispecific F(ab')3 Derivatives that Use Cooperative Signaling Via the TCR/CD3 Complex and CD2 to Activate and Redirect Resting Cytotoxic T Cells" J. Immunol. 147:60-69.
Yang et al. (2016) "A Dual AAV System Enables the Cas9-Mediated Correction of a Metabolic Liver Disease in Newborn Mice" Nat Biotechnol. 34(3):334-8.
Wu et al. (1987) "Receptor-Mediated in Vitro Gene Transformation by a Soluble DNA Carrier System" J. Biol. Chem. 262:4429-4432.
Eriksson and Johansson (1990) "Is Glucagon of Importance for the Hyperammonemia in Patients with Liver Cirrhosis?", Scandinavian Journal of Gastroenterology, 25(Supplement 176):14.

* cited by examiner

\*: p<0.05 between the two treatments in *Otc* mutant mice, \*\*\*\*: p<0.0001 between the two treatments in *Otc* mutant mice, ^^^^: p<0.0001 between the two treatments in wild-type mice \*\*: p<0.01 between the two treatments in *Otc* mutant mice, \*\*\*\*: p<0.0001 between the two treatments in *Otc* mutant mice

*: $p<0.05$ between the two treatments in *Otc* mutant mice, **: $p<0.01$ between the two treatments in *Otc* mutant mice

METHODS OF TREATING UREA CYCLE DISORDERS BY INTERFERING WITH GLUCAGON RECEPTOR SIGNALING

CROSS-REFERENCE TO RELATED APPLICATIONS

This application is a National Stage Application of PCT/US2018/047286, filed Aug. 21, 2018, which claims the benefit under 35 USC § 119 (e) of U.S. Provisional Application No. 62/548,632, filed Aug. 22, 2017 each of which are incorporated herein by reference. To the extent appropriate, a claim of priority is made to each of the above-disclosed applications.

TECHNICAL FIELD

The invention relates to methods of using a glucagon (GCG) inhibitor or a glucagon receptor (GCGR) antagonist to treat urea cycle disorders and/or hyperammonemia, and/or reducing the therapeutic dose of sodium phenylbutyrate or sodium benzoate in a subject in need thereof.

SEQUENCE LISTING

An official copy of the sequence listing is submitted concurrently with the specification electronically via EFS-Web as an ASCII formatted sequence listing with a file name of 10366WO01_US_SEQ_LIST_ST25, a creation date of Aug. 21, 2018, and a size of about 116 kilobytes. The sequence listing contained in this ASCII formatted document is part of the specification and is herein incorporated by reference in its entirety.

BACKGROUND

Glucagon is a 29 residue polypeptide hormone, which in cooperation with insulin, mediates homeostatic regulation of the amount of glucose in the blood. Glucagon primarily acts by stimulating certain cells, for example, liver cells, to release glucose when blood glucose levels fall to maintain normal blood glucose levels. The action of glucagon is opposite to that of insulin, which stimulates cells to take up and store glucose whenever blood glucose levels rise. Glucagon is produced in the alpha cells of the pancreas, whereas insulin is secreted from the neighboring beta cells. The glucagon receptor is a member of the class B G-protein coupled family of receptors, and is activated by glucagon binding. Glucagon receptors are predominantly expressed in the liver and kidney.

The action of glucagon can be suppressed by providing an antagonist, such as a small molecule inhibitor, shRNA, siRNA, a GCG antibody, or a GCGR antibody, as described herein. Anti-GCG antibodies are mentioned, e.g., in U.S. Pat. Nos. 4,206,199; 4,221,777; 4,423,034; 4,272,433; 4,407,965; 5,712,105; and in PCT publications WO2007/124463 and WO2013/081993. Anti-GCGR antibodies are described in U.S. Pat. Nos. 5,770,445, 7,947,809, and 8,545,847; European patent application EP2074149A2; EP patent EP0658200B1; US patent publications 2009/0041784; 2009/0252727; and 2011/0223160; and PCT publication WO2008/036341. Small molecule inhibitors of GCG or GCGR are mentioned, e.g. in WO 07/47676; WO 06/86488; WO 05/123688; WO 05/121097; WO 06/14618; WO 08/42223; WO 08/98244; WO 2010/98948; US 20110306624; WO 2010/98994; WO 2010/88061; WO 2010/71750; WO 2010/30722; WO 06/104826; WO 05/65680; WO 06/102067; WO 06/17055; WO 2011/07722; or WO 09/140342. Inhibition of glucagon affects the GCG/GCGR downstream signaling pathway, inhibiting cAMP and PKA.

Urea cycle disorders (UCDs) result from genetic mutations causing defects in the metabolism of nitrogen produced by the breakdown of protein and other nitrogen-containing compounds. Deficiencies in N-acetylglutamate synthetase (NAGS), carbamoylphosphate synthetase I (CPSI), ornithine transcarbamylase (OTC), argininosuccinate synthetase (ASS, also referred to as Citrullinemia I), citrin (Citrullinemia II), argininosuccinate lyase (Argininosuccinic Aciduria), arginase (Hyperargininemia), and ornithine translocase (HHH Syndrome) are associated with the disease, though there are differences in timing of presentation of hyperammonemia crisis as some affect newborns, others affect adults, and some, for example, Citrullinemia II, can present in either newborns or adults. Amino acid metabolism enzymes are upstream of the urea cycle and are involved in ammonia production through degradation of amino acids. The enzymes involved include cystathionase (CTH), serine dehydratase (SDS), ornithine aminotransferase (OAT), and glutaminase 2 (GLS-2).

Urea cycle disorders and hyperammonemia cause a plethora of symptoms, but typically result in intellectual and developmental disabilities and eventual death without treatment. Available treatment options include dietary protein restriction and nitrogen disposal using phenylbutyrate, though ultimately many subjects with hyperammonemia and/or a urea cycle disorder require liver transplantation.

Given the absence of effective therapies to treat, or to slow the progression of severe hyperammonemia and/or urea cycle disorders, i.e., to extend the life and/or improve the quality of life of a subject having hyperammonemia and/or a urea cycle disorder, there is a need to identify and explore the use of other agents for treating these diseases, such as the glucagon signaling pathway inhibitors and antagonists as described herein.

BRIEF SUMMARY

Provided herein are methods for treating a subject with a condition or disease characterized by hyperammonemia, by administering a glucagon signaling pathway antagonist, e.g. a GCG inhibitor or a GCGR antagonist, or a pharmaceutical composition comprising a GCG inhibitor or GCGR antagonist. A GCG inhibitor or GCGR antagonist is a compound capable of blocking or inhibiting the glucagon receptor signaling pathway. The antagonist may take the form of a small molecule inhibitor, shRNA, siRNA, peptide inhibitor, CRISPR technology (Clustered regularly interspaced short palindromic repeats; CRISPR technology can generate GCGR knock-down or deletion of regulatory sequences affecting GCGR activity), an antisense inhibitor, DARPin, and a GCG or GCGR neutralizing monoclonal antibody. The glucagon signaling pathway antagonist can be administered alone, in a pharmaceutical composition, or in conjunction with one or more therapeutic agents, supplements, or therapeutic procedures useful in treating a condition or disease associated with hyperammonemia, or in treating one or more symptoms associated with a urea cycle disorder, or in lowering blood ammonia levels in a subject having a condition or disease associated with a urea cycle disorder.

In some embodiments, the method comprises administering to a subject having hyperammonemia a therapeutically effective amount of a composition comprising a glucagon signaling pathway antagonist such that serum ammonia levels are lowered or that the condition or disease is mediated, or at least one symptom or complication associated with the condition or disease is alleviated or reduced in severity. In some aspects, the hyperammonemia is congenital hyperammonemia. For example, the congenital hyperammonemia can be caused by a defect in a urea cycle enzyme selected from the group consisting of carbamyl phosphate synthetase (CPS1), N-acetylglutamate synthetase (NAGS), ornithine transcarbamylase (OTC), argininosuccinic acid synthetase (ASS), argininosuccinate lyase (ASL), and arginase (AR1); or a defect in a urea cycle transporter, e.g. ornithine translocase (ORNT1) and citrin. The congenital hyperammonemia can be caused by methylmalonic aciduria, propionic aciduria, or isovaleric aciduria. The congenital hyperammonemia can be caused by medium-chain acyl-CoA dehydrogenase deficiency, multiple acyl-CoA dehydrogenase deficiency, carnitine palmitoyltransferase II deficiency, carnitine-acylcarnitine translocase, lysinuric protein intolerance, pyrroline-5-carboxylate synthetase deficiency, pyruvate carboxylase deficiency, ornithine aminotransferase deficiency, carbonic anhydrase Va deficiency, hyperinsulinism-hyperammonemia syndrome, mitochondrial disorders, and glutamine synthetase deficiency. In some aspects, the hyperammonemia is acquired. For example, the hyperammonemia can be caused by liver disease and complications thereof; by treatment with a therapeutic agent (L-asparaginase or pegaspargase), 5-pentanoic acid, valproic acid, a corticosteroid, or a cyclophosphamide.

In some aspects, the hyperammonemia is caused by herpes simplex infection, hepatitis B infection, or infection with urease-producing organisms.

In some aspects, the hyperammonemia is caused by total parenteral nutrition (with relative arginine deficiency), L-asparaginase treatment, nutritional carnitine deficiency, cystoscopy with glycine-containing solutions, post-lung/bone marrow transplantation, vascular malformations, or transient hyperammonemia of the newborn.

Provided herein are methods for treating a subject with a urea cycle disorder, wherein the subject exhibits elevated levels of ammonia. In some embodiments, the method comprises administering to the subject a therapeutically effective amount of a composition comprising a glucagon signaling pathway antagonist.

Provided herein are methods for treating a subject with a urea cycle disorder, wherein the subject does not exhibit elevated levels of ammonia. In some embodiments, the method comprises administering to the subject a therapeutically effective amount of a composition comprising a glucagon signaling pathway antagonist.

Provided herein are methods for lowering blood ammonia levels, or for treating a condition or disease associated with, or characterized in part by hyperammonemia, or at least one symptom or complication associated with the condition or disease. In some embodiments, the method comprises administering to a subject a therapeutically effective amount of a composition comprising glucagon signaling pathway antagonist, such that blood ammonia levels are lowered or that the condition or disease is mediated, or at least one symptom or complication associated with the condition or disease is alleviated or reduced in severity.

In some aspects, the glucagon signaling pathway antagonist is selected from a small molecule inhibitor, shRNA, siRNA, a peptide inhibitor, CRISPR technology (Clustered regularly interspaced short palindromic repeats; CRISPR technology can generate GCGR knock-down or deletion of regulatory sequences affecting GCGR activity), an antisense inhibitor, a DARPin, and a GCG inhibitor or a GCGR antagonist (such as a neutralizing monoclonal antibody).

In some aspects, the GCGR antagonist can be an anti-GCGR antibody. The anti-GCGR antibody can inhibit or antagonize the GCGR. The anti-GCGR antibody can inhibit or block the GCGR signaling pathway. In some aspects, the GCG inhibitor can be an anti-GCG antibody. The anti-GCG antibody can inhibit binding of GCG to the GCGR.

In certain embodiments, the antibody or antigen-binding fragment specifically binds hGCGR, and comprises the heavy and light chain CDR domains contained within heavy and light chain sequence pairs selected from the group consisting of SEQ ID NO: 2/10, 18/26, 34/42, 50/58, 66/68, 70/78, 86/88, 90/98, 106/108, 110/118, 126/128, 130/138 and 146/148.

In certain embodiments, the antibody or antigen-binding fragment comprises the heavy and light chain CDR domains contained within the HCVR/LCVR amino acid sequence pair of SEQ ID NOs: 86/88.

In certain embodiments, the antibody or antigen-binding fragment comprises a HCVR/LCVR amino acid sequence pair of SEQ ID NOs: 86/88.

In one embodiment, the human antibody or antigen-binding fragment of a human antibody that binds hGCGR, comprises a heavy chain variable region (HCVR) having an amino acid sequence selected from the group consisting of SEQ ID NO: 2, 18, 34, 50, 66, 70, 86, 90, 106, 110, 126, 130 and 146, or a substantially similar sequence thereof having at least 90%, at least 95%, at least 98% or at least 99% sequence identity.

In one embodiment, the human antibody or antigen-binding fragment of a human antibody that binds hGCGR comprises a light chain variable region (LCVR) having an amino acid sequence selected from the group consisting of SEQ ID NO: 10, 26, 42, 58, 68, 78, 88, 98, 108, 118, 128, 138 and 148, or a substantially similar sequence thereof having at least 90%, at least 95%, at least 98% or at least 99% sequence identity.

In certain embodiments, the human antibody or fragment thereof that binds hGCGR comprises a HCVR/LCVR amino acid sequence pair selected from the group consisting of SEQ ID NO: 2/10, 18/26, 34/42, 50/58, 66/68, 70/78, 86/88, 90/98, 106/108, 110/118, 126/128, 130/138, and 146/148. In certain embodiments, the HCVR/LCVR amino acid sequence pair is selected from the group consisting of SEQ ID NO: 34/42, 70/78, 86/88, 110/118 and 126/128.

In certain embodiments, the isolated human antibody or an antigen-binding fragment thereof that binds specifically to hGCGR comprises a HCVR comprising the three heavy chain CDRs (HCDR1, HCDR2 and HCDR3) contained within the HCVR sequence selected from the group consisting of SEQ ID NO: 2, 18, 34, 50, 66, 70, 86, 90, 106, 110, 126, 130 and 146; and/or a LCVR comprising the three light chain CDRs (LCDR1, LCDR2 and LCDR3) contained within the LCVR sequences selected from the group consisting of SEQ ID NO: 10, 26, 42, 58, 68, 78, 88, 98, 108, 118, 128, 138 and 148.

In certain embodiments, the methods provided herein contemplate the use of an isolated human antibody or antigen-binding fragment thereof that binds hGCGR comprising a HCDR3 domain having an amino acid sequence selected from the group consisting of SEQ ID NO: 8, 24, 40, 56, 76, 96, 116 and 136, or a substantially similar sequence thereof having at least 90%, at least 95%, at least 98% or at least 99% sequence identity; and/or a LCDR3 domain having an amino acid sequence selected from the group consisting of SEQ ID NO: 16, 32, 48, 64, 84, 104, 124 and 144, or a substantially similar sequence thereof having at least 90%, at least 95%, at least 98% or at least 99% sequence identity.

In one embodiment, the methods provided herein contemplate use of an antibody or fragment thereof that further comprises a HCDR1 domain having an amino acid sequence selected from the group consisting of SEQ ID NO: 4, 20, 36, 52, 72, 92, 112 and 132, or a substantially similar sequence thereof having at least 90%, at least 95%, at least 98% or at least 99% sequence identity; a HCDR2 domain having an amino acid sequence selected from the group consisting of SEQ ID NO: 6, 22, 38, 54, 74, 94, 114 and 134, or a substantially similar sequence thereof having at least 90%, at least 95%, at least 98% or at least 99% sequence identity; a LCDR1 domain having an amino acid sequence selected from the group consisting of SEQ ID NO: 12, 28, 44, 60, 80, 100, 120 and 140, or a substantially similar sequence thereof having at least 90%, at least 95%, at least 98% or at least 99% sequence identity; and a LCDR2 domain having an amino acid sequence selected from the group consisting of SEQ ID NO: 14, 30, 46, 62, 82, 102, 122 and 142, or a substantially similar sequence thereof having at least 90%, at least 95%, at least 98% or at least 99% sequence identity.

In one embodiment, the antibody or antigen-binding fragment of an antibody comprises:
  (a) a HCDR3 domain having an amino acid sequence selected from the group consisting of SEQ ID NO: 8, 24, 40, 56, 76, 96, 116 and 136; and
  (b) a LCDR3 domain having an amino acid sequence selected from the group consisting of SEQ ID NO: 16, 32, 48, 64, 84, 104, 124 and 144.

In a related embodiment, the antibody or antigen-binding fragment of the antibody further comprises:
  (c) a HCDR1 domain having an amino acid sequence selected from the group consisting of SEQ ID NO: 4, 20, 36, 52, 72, 92, 112 and 132;
  (d) a HCDR2 domain having an amino acid sequence selected from the group consisting of SEQ ID NO: 6, 22, 38, 54, 74, 94, 114 and 134;
  (e) a LCDR1 domain having an amino acid sequence selected from the group consisting of SEQ ID NO: 12, 28, 44, 60, 80, 100, 120 and 140; and
  (f) a LCDR2 domain having an amino acid sequence selected from the group consisting of SEQ ID NO: 14, 30, 46, 62, 82, 102, 122 and 142.

In one embodiment, the antibody or antigen-binding fragment thereof comprises a HCVR comprising a HCDR1 domain having an amino acid sequence selected from one of SEQ ID NO: 4, 20, 36, 52, 72, 92, 112 and 132; a HCDR2 domain having an amino acid sequence selected from one of SEQ ID NO: 6, 22, 38, 54, 74, 94, 114 and 134; a HCDR3 domain having an amino acid sequence selected from one of SEQ ID NOs: 8, 24, 40, 56, 76, 96, 116 and 136; and a LCVR comprising a LCDR1 domain having an amino acid sequence selected from one of SEQ ID NO: 12, 28, 44, 60, 80, 100, 120 and 140; a LCDR2 domain having an amino acid sequence selected from one of SEQ ID NO: 14, 30, 46, 62, 82, 102, 122 and 142; and a LCDR3 domain having an amino acid sequence selected from one of SEQ ID NO: 16, 32, 48, 64, 84, 104, 124 and 144.

In certain embodiments, the human antibody or antigen-binding fragment of a human antibody that binds to human GCGR comprises a HCDR3/LCDR3 amino acid sequence pair selected from the group consisting of SEQ ID NO: 8/16, 24/32, 40/48, 56/64, 76/84, 86/88, 96/104, 116/124 and 136/144. Non-limiting examples of anti-GCGR antibodies having these HCDR3/LCDR3 pairs are the antibodies designated H4H1345N, H4H1617N, H4H1765N, H4H1321B and H4H1321P, H4H1327B and H4H1327P, H4H1328B and H4H1328P, H4H1331B and H4H1331P, H4H1339B and H4H1339P, respectively.

In one embodiment, the isolated antibody or antigen-binding fragment thereof useful according to the methods provided herein, that specifically binds to GCG and neutralizes at least one activity associated with GCG, comprises: (a) three heavy chain complementarity determining regions (HCDR1, HCDR2 and HCDR3) contained within a heavy chain variable region (HCVR) amino acid sequence selected from the group consisting of SEQ ID NOs: 150, 166, 182, 198, 214, 230, 246, 262, 278 and 294; and (b) three light chain CDRs (LCDR1, LCDR2 and LCDR3) contained within a light chain variable region (LCVR) amino acid sequence selected from the group consisting of SEQ ID NOs: 158, 174, 190, 206, 222, 238, 254, 270, 286 and 302.

In some embodiments, the isolated antibody or antigen-binding fragment thereof that specifically binds to GCG and neutralizes at least one activity associated with GCG, comprises a HCVR having an amino acid sequence selected from the group consisting of SEQ ID NOs: 150, 166, 182, 198, 214, 230, 246, 262, 278 and 294 and a LCVR having an amino acid sequence selected from the group consisting of SEQ ID NOs: 158, 174, 190, 206, 222, 238, 254, 270, 286 and 302.

In some embodiments, the isolated antibody or antigen-binding fragment thereof that specifically binds to GCG and neutralizes at least one activity associated with GCG, comprises a HCVR/LCVR amino acid sequence pair selected from the group consisting of SEQ ID NOs: 150/158; 166/174; 182/190; 198/206; 214/222; 230/238; 246/254; 262/270; 278/286 and 294/302.

In some embodiments, the HCVR/LCVR amino acid sequence pair comprises SEQ ID NOs: 166/174.

In some embodiments, the HCVR/LCVR amino acid sequence pair comprises SEQ ID NOs: 182/190.

In one embodiment, the isolated antibody or antigen-binding fragment thereof useful according to the methods provided herein, comprises:
  (a) a HCDR1 domain having an amino acid sequence selected from the group consisting of SEQ ID NOs: 152, 168, 184, 200, 216, 232, 248, 264, 280, and 296;
  (b) a HCDR2 domain having an amino acid sequence selected from the group consisting of SEQ ID NOs: 154, 170, 186, 202, 218, 234, 250, 266, 282, and 298;
  (c) a HCDR3 domain having an amino acid sequence selected from the group consisting of SEQ ID NOs: 156, 172, 188, 204, 220, 236, 252, 268, 284, and 300;
  (d) a LCDR1 domain having an amino acid sequence selected from the group consisting of SEQ ID NOs: 160, 176, 192, 208, 224, 240, 256, 272, 288, and 304;
  (e) a LCDR2 domain having an amino acid sequence selected from the group consisting of SEQ ID NOs: 162, 178, 194, 210, 226, 242, 258, 274, 290, and 306; and
  (f) a LCDR3 domain having an amino acid sequence selected from the group consisting of SEQ ID NOs: 164, 180, 196, 212, 228, 244, 260, 276, 292, and 308.

In one embodiment, the isolated antibody or antigen-binding fragment thereof useful according to the methods provided herein, comprises:
  (a) a HCDR1 domain comprising the amino acid sequence of SEQ ID NO: 168;
  (b) a HCDR2 domain comprising the amino acid sequence of SEQ ID NO: 170;

(c) a HCDR3 domain comprising the amino acid sequence of SEQ ID NO: 172;
(d) a LCDR1 domain comprising the amino acid sequence of SEQ ID NO: 176;
(e) a LCDR2 domain comprising the amino acid sequence of SEQ ID NO: 178; and
(f) a LCDR3 domain comprising the amino acid sequence of SEQ ID NO: 180.

In one embodiment, the isolated antibody or antigen-binding fragment thereof useful according to the methods provided herein, comprises:
(a) a HCDR1 domain comprising the amino acid sequence of SEQ ID NO: 184;
(b) a HCDR2 domain comprising the amino acid sequence of SEQ ID NO: 186;
(c) a HCDR3 domain comprising the amino acid sequence of SEQ ID NO: 188;
(d) a LCDR1 domain comprising the amino acid sequence of SEQ ID NO: 192;
(e) a LCDR2 domain comprising the amino acid sequence of SEQ ID NO: 194; and
(f) a LCDR3 domain comprising the amino acid sequence of SEQ ID NO: 196.

Also useful according to the methods provided herein are antibodies or antigen-binding fragments thereof that specifically bind GCG, comprising a heavy chain CDR1 (HCDR1) comprising an amino acid sequence selected from any of the HCDR1 amino acid sequences provided herein or a substantially similar sequence thereof having at least 90%, at least 95%, at least 98% or at least 99% sequence identity.

Also useful according to the methods provided herein are antibodies or antigen-binding fragments thereof that specifically bind GCG, comprising a heavy chain CDR2 (HCDR2) comprising an amino acid sequence selected from any of the HCDR2 amino acid sequences provided herein or a substantially similar sequence thereof having at least 90%, at least 95%, at least 98% or at least 99% sequence identity.

Also useful according to the methods provided herein are antibodies or antigen-binding fragments thereof that specifically bind GCG, comprising a heavy chain CDR3 (HCDR3) comprising an amino acid sequence selected from any of the HCDR3 amino acid sequences provided herein or a substantially similar sequence thereof having at least 90%, at least 95%, at least 98% or at least 99% sequence identity.

Also useful according to the methods provided herein are antibodies or antigen-binding fragments thereof that specifically bind GCG, comprising a light chain CDR1 (LCDR1) comprising an amino acid sequence selected from any of the LCDR1 amino acid sequences provided herein or a substantially similar sequence thereof having at least 90%, at least 95%, at least 98% or at least 99% sequence identity.

Also useful according to the methods provided herein are antibodies or antigen-binding fragments thereof that specifically bind GCG, comprising a light chain CDR2 (LCDR2) comprising an amino acid sequence selected from any of the LCDR2 amino acid sequences provided herein or a substantially similar sequence thereof having at least 90%, at least 95%, at least 98% or at least 99% sequence identity.

Also useful according to the methods provided herein are antibodies or antigen-binding fragments thereof that specifically bind GCG, comprising a light chain CDR3 (LCDR3) comprising an amino acid sequence selected from any of the LCDR3 amino acid sequences listed herein or a substantially similar sequence thereof having at least 90%, at least 95%, at least 98% or at least 99% sequence identity.

Also useful according to the methods provided herein are antibodies or antigen-binding fragments thereof that specifically bind GCG, comprising an HCDR3 and an LCDR3 amino acid sequence pair (HCDR3/LCDR3) comprising any of the HCDR3 amino acid provided herein paired with any of the LCDR3 amino acid sequences provided herein. According to certain embodiments, the antibodies, or antigen-binding fragments thereof, comprise an HCDR3/LCDR3 amino acid sequence pair contained within any of the exemplary anti-GCG antibodies provided herein. In certain embodiments, the HCDR3/LCDR3 amino acid sequence pair comprises SEQ ID NOs: 172/180.

Also useful according to the methods provided herein are antibodies or antigen-binding fragments thereof that specifically bind GCG, comprising a set of six CDRs (i.e., HCDR1-HCDR2-HCDR3-LCDR1-LCDR2-LCDR3) contained within any of the exemplary anti-GCG antibodies provided herein. In certain embodiments, the HCDR1/HCDR2/HCDR3/LCDR1/LCDR2/LCDR3 amino acid sequence set comprises SEQ ID NOs: 168/170/172/176/178/180. In certain embodiments, the HCDR1/HCDR2/HCDR3/LCDR1/LCDR2/LCDR3 amino acid sequence set comprises SEQ ID NOs: 184/186/188/192/194/196.

In a related embodiment, the antibodies, or antigen-binding fragments thereof that specifically bind GCG, comprise a set of six CDRs (i.e., HCDR1/HCDR2/HCDR3/LCDR1/LCDR2/LCDR3) contained within a HCVR/LCVR amino acid sequence pair as defined by any of the exemplary anti-GCG antibodies provided herein. For example, the antibodies or antigen-binding fragments thereof that specifically bind GCG, comprise the HCDR1/HCDR2/HCDR3/LCDR1/LCDR2/LCDR3 amino acid sequences set contained within a HCVR/LCVR amino acid sequence pair selected from the group consisting of: 166/174; 182/190; 198/206; 214/222; 230/238; 246/254; 262/270; 278/286 and 294/302.

Non-limiting examples of antibodies that specifically bind GCG and comprise the CDR sequences provided above, include H1H059P, H4H10223P, H4H10231P, H4H10232P, H4H10236P, H4H10237P, H4H10238P, H4H10250P, H4H10256P, and H4H10270P.

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, (1991) "Sequences of Proteins of Immunological Interest," National Institutes of Health, Bethesda, Md.; Al-Lazikani et al., (1997) J. Mol. Biol. 273:927-948; and Martin et al., (1989) Proc. Natl. Acad. Sci. USA 86:9268-9272. Public databases are also available for identifying CDR sequences within an antibody.

In some embodiments, a subject having hyperammonemia may suffer from one of the conditions or diseases selected from the following: a urea cycle disorder, liver disease and conditions associated with liver disease such as hepatic encephalopathy and fetor hepaticus, and a condition or disease associated with the presence of an enzyme defect associated with a urea cycle disorder or reported to cause hyperammonemia. In some embodiments, elevated ammonia levels are detected in subject sera. In some embodiments, elevated glutamine levels are detected in subject sera.

In some aspects, the enzyme defect associated with a urea cycle disorder is selected from the following: carbamyl phosphate synthetase (CPS1), N-acetylglutamate synthetase (NAGS), ornithine transcarbamylase (OTC), argininosuccinic acid synthetase (ASS), argininosuccinate lyase (ASL), and arginase (AR1). In some aspects, the urea cycle disorder is related to a transporter defect selected from the following: ornithine translocase (ORNT1; ornithine/citrulline carrier; solute carrier family 25, member 15) and citrin (aspartate/glutamate carrier; solute carrier family 25, member 13).

In some aspects, the glucagon signaling pathway antagonist is administered with amino acid formulas, such as those selected from Cyclinex (e.g., Cyclinex-1 or -2), EAA (essential amino acids), UCD I or II (Urea Cycle Disorder-1 or -II), and individual branched chain amino acids.

In some aspects, the glucagon signaling pathway antagonist is administered with antioxidants or electrolytes.

In some aspects, the glucagon signaling pathway antagonist is administered with L-citrulline or L-arginine free base.

In some aspects, the glucagon signaling pathway antagonist is administered along with hemodialysis or continuous renal replacement.

In some aspects, the composition comprising the glucagon signaling pathway antagonist is administered to a subject in combination with at least one additional therapeutic agent. The additional therapeutic agent can be any agent that alleviates or reduces the symptoms and signs associated with hyperammonemia and/or a urea cycle disorder. In some embodiments, at least one additional therapeutic agent is selected from the following: non-absorbable antibiotic (rifaximin or lactulose), sodium phenylbutyrate, sodium benzoate, sodium phenylacetate, glycerol phenylbutyrate, carbamyl glutamate (Carbaglu®), a second GCG inhibitor, and a second GCGR antagonist.

Provided herein are methods of reducing the amount and/or dosage of sodium phenylbutyrate or sodium benzoate necessary to treat a subject with hyperammonemia. In some embodiments, the method comprises administering to the subject a therapeutically effective amount of a composition comprising a glucagon signaling pathway antagonist. In some aspects, the glucagon signaling pathway antagonist is administered concomitantly with sodium phenylbutyrate or sodium benzoate.

Other objects and advantages will become apparent from a review of the ensuing detailed description.

DESCRIPTION

Figure 1:
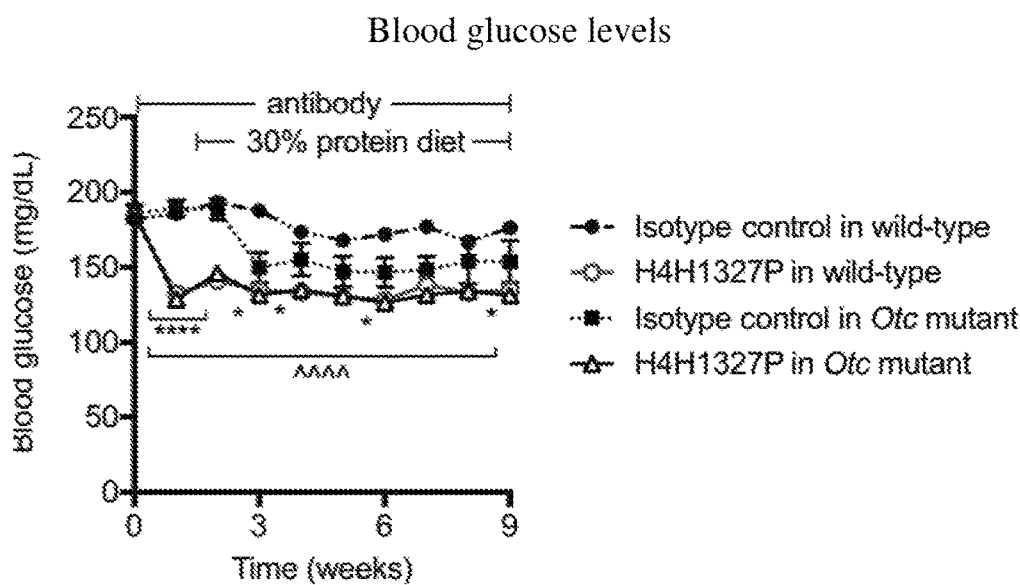
FIG. 1 is a graphical representation of Table 3, and depicts mean±SEM of non-fasting blood glucose levels for the four groups of mice.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All patents, applications and non-patent publications mentioned in this specification are incorporated herein by reference in their entireties.

General Description

Amino acid metabolism enzymes are involved in ammonia production through degradation of amino acids. The enzymes involved include cystathionase (CTH), serine dehydratase (SDS), ornithine aminotransferase (OAT), and glutaminase 2 (GLS-2). The resulting ammonia from amino acid metabolism, as well as ammonia absorbed from the gut or produced by the skeletal muscles during exercise, or produced by ammoniagenesis by the kidney, is converted to urea by the urea cycle in hepatocytes. The urea cycle is the principal mechanism for the clearance of ammonia resulting from protein turnover, as well as for the metabolism of other nitrogenous metabolic compounds such as adenosine monophosphate, by converting ammonia to urea. The urea is then excreted through urine. Glutamine synthetase activity is also required to reduce plasma ammonia levels. A glucagon signaling pathway inhibitor such as a GCGR antibody targets the amino acid transporter to reduce amino acid uptake to hepatocytes.

Urea cycle disorders result from a genetic mutation in a gene encoding one of the enzymes in the urea cycle, enzymes responsible for converting ammonia to urea. Disruption of the urea cycle, typically through dysfunction of a urea cycle enzyme or a transporter defect, or through accumulation of metabolites or by substrate deficiencies, results in accumulation of nitrogen in the form of ammonia, a condition referred to as hyperammonemia. Elevated ammonia in the blood causes irreversible brain damage, coma, and death. Seizures are common in acute hyperammonemia and may result from cerebral damage. Subclinical seizures are common in acute hyperammonemic episodes, especially in neonates, and may be seen during the rise of glutamine even before ammonia levels are maximal. Ammonia can cause brain damage through a variety of mechanisms, a major component of which is cerebral edema through increased glutamine, though the specific roles of ammonia, glutamate, and glutamine in cerebral edema have yet to be elucidated. In addition, adverse effects on the nitric oxide production system may also contribute to injury, as may arginine deficiency due to ASL deficiency.

In addition to increases in plasma ammonia levels, changes in plasma and/or urine levels of the following may be seen in one or more forms of urea cycle disorders:
Increase or decrease in plasma citrullin;
Increase in plasma and/or urine levels of argininosuccinic acid (ASA);
Increase or decrease in plasma arginine;
Increase in plasma ornithine;
Increase in plasma glutamine;
Increase in plasma alanine;
Increase in plasma asparagine;
Increase in urinary orotic acid; or
Increase in urine homocitrulline.

In some subjects, the urea cycle disorder is associated with the presence of an inborn error of urea synthesis, or urea cycle enzyme defect: Carbamyl Phosphate Synthetase (CPS1), N-Acetylglutamate Synthetase (NAGS), Ornithine Transcarbamylase (OTC Deficiency), Argininosuccinic Acid Synthetase (ASS, Citrullinemia), Argininosuccinate Lyase (AL or ASA Lyase, Argininosuccinic Aciduria), and Arginase (AR1).

Other inborn errors of metabolism may also cause hyperammonemia: Ornithine aminotransferase (OAT) deficiency (in neonates), Tyrosinemia type 1, Galactosemia, mitochondrial disorders, citrin deficiency leading to Citrullinemia type II (CTLN2), and neonatal intrahepatic cholestasis caused by citrin deficiency (NICCD). CTLN2 is a late-onset disorder, where hepatic dysfunction is absent, but the subject experiences recurrent hyperammonemia, delirium, irritability, and fatty liver infiltration. Citrin deficiency results from mutation of the gene SLC25A13. As citrin functions to transport aspartate/glutamate across the mitochondrial membrane to the cytoplasm, a deficiency in citrin results in a decrease in cytoplasmic aspartate which limits the activity of the enzyme argininosuccinic acid synthase. Dysfunction of another transporter, ornithine translocase, results in hyperornithinemia, homocitrullinuia, and hyperammonemia, as the reduction in ornithine transport into the mitochondria results in orotic aciduria and deficiency of urea synthesis.

Other congenital disorders which cause hyperammonemia include Propionic acidemia, Isolated methylmalonic acidemia, Isovaleric acidemia, Carbonic anhydrase VA deficiency, Lysinuric protein intolerance, carnitine palmitoyl transferase II deficiency, carnitine-acylcarnitine translocase, pyrroline-5-carboxylate synthetase deficiency, pyruvate carboxylase deficiency, carbonic anhydrase Va deficiency, hyperinsulinism-hyperammonemia syndrome, mitochondrial disorders, glutamine synthetase deficiency, fatty acid oxidation disorders (for example, Short-Chain Acyl-CoA Dehydrogenase Deficiency, Medium-Chain Acyl-Coenzyme A Dehydrogenase Deficiency, Multiple Acyl-Coenzyme A Dehydrogenase Deficiency, Very Long-Chain Acyl-Coenzyme A Dehydrogenase Deficiency), and Hyperinsulinism-hyperammonemia syndrome (Familial Hyperinsulinism). See Häberle, Archives of Biochemistry and Biophysics, 536: 101-108, 2013.

Depending on the degree of the enzyme or transporter dysfunction, the onset and severity of urea cycle disorders are highly variable. Severe deficiency or total absence of activity of any of the first four enzymes in the pathway (CPS1, OTC, ASS1, and ASL) or the cofactor producer (NAGS) results in the accumulation of ammonia and other precursor metabolites during the first few days of life. Newborns with severe urea cycle dysfunction become catastrophically ill within days of birth. Symptoms include irritability, poor feeding, vomiting, and lethargy, followed by seizures, hypotonia, respiratory distress, and coma.

Those with partial urea cycle dysfunction, including children and adults, present with subtle symptoms, and often diagnosis is difficult given the symptoms are not commonly recognized. Children with mild or moderate urea cycle dysfunction may have early symptoms including failure to thrive, inconsolable crying, agitation or hyperactive behavior, and aversion to foods containing high protein. Later symptoms include frequent vomiting, lethargy, delirium, and if untreated, hyperammonemic coma and death.

Late-onset in adults is identified when a hyperammonemia crisis is triggered by a metabolic stressor including viral infection, excessive exercise or dieting, post-partum stress, parenteral nutrition with high protein administration, gastrointestinal bleeding, administration of valproic acid, administration of prednisone or other corticosteroid, infection, and post-operative stress. Symptoms typically involve episodes of disorientation, confusion, slurred speech, combativeness or agitation, stroke-like symptoms, lethargy and delirium. Subjects are often treated for psychiatric symptoms prior to diagnosis. Without treatment, a subject experiencing a hyperammonemia crisis is at risk for permanent brain damage, coma, and death.

Exemplary late-onset subjects can be a bodybuilders on high protein diets. Such subjects are high risk, having an undiagnosed urea cycle disorder that when combined with a high protein diet, triggers a hyperammonemia crisis. Such subjects can be improperly diagnosed as they appear to be otherwise very healthy individuals. The delay in diagnosis results in coma and death.

Additional causes of hyperammonemia, i.e. acquired hyperammonemia, include liver disease and complications thereof, e.g., hepatic encephalopathy in subjects with advanced liver disease, fetor hepaticus (a late sign of liver failure), vascular bypass of the liver, and biliary atresia; administration of toxic levels of valproic acid (metabolites of valproic acid inhibit NAGS, also deplete carnitine), corticosteroid, or cyclophosphamide; herpes simplex infection; and gastrointestinal bacterial overgrowth. Hyperammonemia can also be caused by infection with urease-producing organisms (increased ammonia production in the intestine or urinary tract).

Furthermore, hyperammonemia can be caused by total parenteral nutrition (with relative arginine deficiency), treatment with L-asparaginase (increased ammonia production due to hydrolysis of asparagine), nutritional carnitine deficiency (impaired fatty acid oxidation leading to lack of acetyl-CoA), cystoscopy with glycine-containing solutions (increased ammonia production from nitrogen overload), post-lung/bone marrow transplantation (reduced glutamine synthetase activity), vascular malformations, or transient hyperammonemia of the newborn. See Häberle, Archives of Biochemistry and Biophysics, 536: 101-108, 2013.

Treatment options initially include hemodialysis or continuous renal replacement therapy (RRT) as soon as it's clear that the subject is experiencing a hyperammonemia crisis. Hemodialysis or RTT may be discontinued when plasma ammonia levels fall below 80 μmol/L, or below 120 μmol/L. In addition, oral or parenteral protein administration is discontinued, while administration of calories from glucose and fat helps prevent excessive catabolic state. Once a diagnosis of a UCD is made, treatment of acute manifestations can be started and treatment is tailored to the specific urea cycle disorder. Therapeutics such as intravenous or oral administration of sodium phenylacetate, sodium benzoate, sodium phenylbutyrate, or glycerol phenylbutyrate scavenge ammonia and divert nitrogen from the urea cycle to excretion through the kidneys. Sodium phenylacetate combines with glutamine, producing phenylacetylglutamine, which is excreted by the kidneys. Sodium benzoate conjugates with glycine, producing sodium hippurate, which is also excreted by the kidneys. Unfortunately, for subjects with recurrent hyperammonemia or those resistant to conventional treatment, liver transplantation is the best treatment option.

While not wishing to be held by theory, it has been determined that an antagonist of GCGR decreases the expression of amino acid metabolism enzymes in the liver of mice and monkeys. As such, blocking the glucagon signaling pathway provides a method for treating hyperammonemia and urea cycle disorders by reducing the amount of ammonia entering the urea cycle.

To date, there have been no studies examining the effects of antagonizing the glucagon signaling pathway on urea cycle disorders or conditions or diseases associated with hyperammonemia. The studies described in the Examples use an antagonist of GCGR as an exemplary inhibitor of the glucagon signaling pathway in a mouse model of urea cycle disorders to demonstrate the effects on hyperammonemia and death over several weeks of treatment.

Definitions

The "glucagon receptor", also referred to herein as "GCGR", belongs to the G protein-coupled receptor class 2 family and consists of a long amino terminal extracellular domain, seven transmembrane segments, and an intracellular C-terminal domain. Glucagon receptors are notably expressed on the surface of hepatocytes where they bind to glucagon and transduce the signal provided thereby into the cell. Accordingly, the term "glucagon receptor" also refers to one or more receptors that interact specifically with glucagon to result in a biological signal. DNA sequences encoding glucagon receptors of rat and human origin have been isolated and disclosed in the art (EP0658200B1). The murine and cynomolgus monkey homologues have also been isolated and sequenced (Burcelin, et al., (1995) Gene 164:305-310); McNally et al., (2004) Peptides 25:1171-1178). As used herein, "glucagon receptor" and "GCGR" are used interchangeably. The expressions "GCGR", "hGCGR" or fragments thereof, as used herein, refer to the human GCGR protein or fragment thereof, unless specified as being from a non-human species, e.g. "mouse GCGR", "rat GCGR", or "monkey GCGR".

The phrase "GCGR antagonist" refers to an inhibitor, antagonist, or inverse agonist of the GCGR signaling pathway. A "GCG inhibitor" may prevent the binding of glucagon to the receptor. A GCGR inhibitor may also prevent the binding of glucagon to the receptor. However, both effectively block or attenuate activation of the receptor, or may interfere with the signaling cascade downstream of the GCGR activation, and are collectively referred to as "glucagon signaling pathway antagonists".

The terms "inhibitor" or "antagonist" include a substance that retards or prevents a chemical or physiological reaction or response, for example, a glucagon signaling pathway antagonist.

A GCGR antagonist is able to bind to the glucagon receptor and thereby antagonize the activity of GCG mediated by the GCGR. Inhibiting the activity of GCG by antagonizing the binding and activity of GCG at the GCGR reduces expression of enzymes involved in amino acid metabolism. Methods by which to determine the binding of a supposed antagonist with the glucagon receptor are known in the art and means by which to determine the interference with glucagon activity at the glucagon receptor are publicly available; see, e.g., S. E. de Laszlo et al., (1999) Bioorg. Med. Chem. Lett. 9:641-646.

Contemplated as useful herein are GCGR antagonists or GCG inhibitors having as a functional component thereof a small molecule compound, or in other words a low molecular weight organic compound. A small molecule is typically less than 800 Daltons. Additionally, CRISPR technology can be used to knock-down GCG or GCGR expression. As such, in some embodiments, a glucagon signaling pathway antagonist can be selected from a small molecule inhibitor, shRNA, siRNA, peptide inhibitor, CRISPR technology (Clustered regularly interspaced short palindromic repeats; CRISPR technology can generate GCGR knock-down or deletion of regulatory sequences affecting GCGR activity), an antisense inhibitor, DARPin, Spiegelmers, aptamers, engineered Fn type-III domains, GCG or GCGR neutralizing monoclonal antibodies, and their derivatives.

An example of a glucagon signaling pathway antagonist includes, but is not limited to, an antibody (human or humanized), or an antigen binding portion thereof, to GCG or GCGR, that blocks binding or inhibits the activity of the GCGR signaling pathway. Exemplary GCGR antagonists that may be used in the methods described herein include isolated human monoclonal antibody or antigen-binding fragment thereof comprising: (a) a HCVR having an amino acid sequence selected from the group consisting of SEQ ID NO: 2, 18, 34, 50, 66, 70, 86, 90, 106, 110, 126, 130 and 146; and/or (b) a LCVR having an amino acid sequence selected from the group consisting of SEQ ID NO: 10, 26, 42, 58, 68, 78, 88, 98, 108, 118, 128, 138 and 148. Exemplary GCG inhibitors that may be used in the methods described herein include isolated human monoclonal antibody or antigen-binding fragment thereof comprising: (a) a HCVR having an amino acid sequence selected from the group consisting of SEQ ID NO: 150, 166, 182, 198, 214, 230, 246, 262, 278, and 294; and/or (b) a LCVR having an amino acid sequence selected from the group consisting of SEQ ID NO: 158, 174, 190, 206, 222, 238, 254, 270, 286, and 302.

A "therapeutically effective dose" is a dose that produces the desired effect for which it is administered. The exact dose will depend on the purpose of the treatment, and will be ascertainable by one skilled in the art using known techniques (see, for example, Lloyd (1999) The Art, Science and Technology of Pharmaceutical Compounding).

By the phrase "substantially identical" is meant a protein sequence having at least 95% identity to a HCVR having an amino acid sequence selected from the group consisting of SEQ ID NO: 2, 18, 34, 50, 66, 70, 86, 90, 106, 110, 126, 130 and 146; and/or (b) a LCVR having an amino acid sequence selected from the group consisting of SEQ ID NO: 10, 26, 42, 58, 68, 78, 88, 98, 108, 118, 128, 138 and 148, and capable of binding GCGR and inhibiting the biological activity of GCGR. The phrase "substantially identical" is also meant a protein sequence having at least 95% identify to a HCVR having an amino acid sequence selected from the group consisting of the amino acid sequences SEQ ID NO: 150, 166, 182, 198, 214, 230, 246, 262, 278, and 294; and/or (b) a LCVR having an amino acid sequence selected from the group consisting of SEQ ID NO: 158, 174, 190, 206, 222, 238, 254, 270, 286, and 302, and capable of binding GCG and inhibiting the biological activity of GCG.

The terms "identity" or "homology" are construed to mean the percentage of amino acid residues in the candidate sequence that are identical with the residue of a corresponding sequence to which it is compared, after aligning the sequences and introducing gaps, if necessary to achieve the maximum percent identity for the entire sequence, and not considering any conservative substitutions as part of the sequence identity. Neither N- or C-terminal extensions nor insertions will be construed as reducing identity or homology. Methods and computer programs for the alignment are well known in the art. Sequence identity may be measured using sequence analysis software (e.g., Sequence Analysis Software Package, Genetics Computer Group, University of Wisconsin Biotechnology Center, 1710 University Ave., Madison, Wis. 53705). This software matches similar sequences by assigning degrees of homology to various substitutions, deletions, and other modifications.

The term "treating" (or "treat" or "treatment") refers to processes involving a slowing, interrupting, inhibiting, arresting, controlling, stopping, reducing, ameliorating, or reversing the progression, duration, or severity of an existing symptom, disorder, condition, or disease, but does not necessarily involve a total elimination of all disease-related symptoms, conditions, or disorders through use of a GCG inhibitor or GCGR antagonist as described herein. Furthermore, "treating", "treatment" or "treat" refers to an approach for obtaining beneficial or desired results including clinical results, which include, but are not limited to, one or more of the following: inhibiting, delaying or preventing the progression of hyperammonemia and/or a urea cycle disorder; inhibiting, delaying or preventing the progression of a disease associated with hyperammonemia, or characterized by elevated plasma ammonia levels such as in chronic liver disease or toxic administration of valproic acid, or a condition or disease associated with the presence of a gene variant reported to cause a urea cycle disorder; or inhibiting, preventing, or ameliorating at least one symptom associated with a disease associated with hyperammonemia; or lowering blood ammonia levels, such that the condition or disease associated with hyperammonemia is mediated, or at least one symptom or complication associated with the condition or disease is alleviated or reduced in severity. "Treatment" or "treating", as used herein, also refers to increasing the quality of life of those suffering from the disease, decreasing the dose of other medications required to treat the disease and/or prolonging survival of subjects. For example, "treatment" or "treating" can include reducing the amount and/or dosage of sodium phenylbutyrate or sodium benzoate necessary to treat a subject with hyperammonemia.

The term "hyperammonemia" is a state in which plasma ammonia levels are greater than normal, e.g. above 30 µmol/L, or above 50 µmol/L, or above 80 µmol/L, or above 100 µmol/L, or above 120 µmol/L. Plasma ammonia levels in severe hyperammonemia are above 1000 µmol/L.

Glucagon Signaling Pathway Inhibitors

Provided herein are glucagon signaling pathway antagonists, e.g., GCG inhibitors and GCGR antagonists, for the treatment of conditions or diseases characterized by hyperammonemia. In some embodiments, the antagonist is an inhibitor of glucagon, for example, amylin and pramlintide. In some embodiments, the antagonist is an inhibitor of GCGR. In some embodiments, the GCGR antagonist is MK-0893, PF-06291874, LGD-6972, or LY2409021.

In some embodiments, the antagonist comprises an antibody capable of binding GCG or GCGR, or a fragment thereof. In some embodiments, the signaling pathway is inhibited by the interruption of GCG or GCGR expression, by, for example, using CRISPR technology or antisense, or by targeting a downstream enzyme such as CaMKII.

In some embodiments, the GCG inhibitor or GCGR antagonist is an antisense molecule (GR-ASO), antibody, small molecule inhibitor, shRNA, siRNA, peptide inhibitor (amylin, pramlintide), DARPin, Spiegelmer, aptamer, engineered Fn type-III domains, or a derivative thereof.

Anti-GCGR Antibodies, Anti-GCG Antibodies, and Antibody Fragments

In some embodiments, the GCGR antagonist is an antibody or antibody fragment as disclosed in U.S. Pat. No. 8,545,847, incorporated by reference herein in its entirety. Antibodies disclosed therein are provided in Table 1.

TABLE 1

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H4H1345N | 2 | 4 | 6 | 8 | 10 | 12 | 14 | 16 |
| H4H1617N | 18 | 20 | 22 | 24 | 26 | 28 | 30 | 32 |
| H4H1765N | 34 | 36 | 38 | 40 | 42 | 44 | 46 | 48 |
| H4H1321B | 50 | 52 | 54 | 56 | 58 | 60 | 62 | 64 |
| H4H1321P | 66 | 52 | 54 | 56 | 68 | 60 | 62 | 64 |
| H4H1327B | 70 | 72 | 74 | 76 | 78 | 80 | 82 | 84 |
| H4H1327P | 86 | 72 | 74 | 76 | 88 | 80 | 82 | 84 |
| H4H1328B | 90 | 92 | 94 | 96 | 98 | 100 | 102 | 104 |
| H4H1328P | 106 | 92 | 94 | 96 | 108 | 100 | 102 | 104 |
| H4H1331B | 110 | 112 | 114 | 116 | 118 | 120 | 122 | 124 |
| H4H1331P | 126 | 112 | 114 | 116 | 128 | 120 | 122 | 124 |
| H4H1339B | 130 | 132 | 134 | 136 | 138 | 140 | 142 | 144 |
| H4H1339P | 146 | 132 | 134 | 136 | 148 | 140 | 142 | 144 |

Additional GCGR antibodies or antibody fragments contemplated as useful herein include those disclosed in U.S. Pat. Nos. 5,770,445 and 7,947,809; European patent application EP2074149A2; EP patent EP0658200B1; U.S. patent publications 2009/0041784; 2009/0252727; and 2011/0223160; and PCT publication WO2008/036341. The patents and publications are incorporated by reference herein in their entirety.

In some embodiments, the GCG inhibitor is an antibody or antibody fragment thereof as disclosed in U.S. 2016/0075778, incorporated by reference herein in its entirety. Antibodies disclosed therein are provided in Table 2.

TABLE 2

| | SEQ ID NOs: | | | | | | | |
|---|---|---|---|---|---|---|---|---|
| Antibody Designation | HCVR | HCDR1 | HCDR2 | HCDR3 | LCVR | LCDR1 | LCDR2 | LCDR3 |
| H1H059P | 150 | 152 | 154 | 156 | 158 | 160 | 162 | 164 |
| H4H10223P | 166 | 168 | 170 | 172 | 174 | 176 | 178 | 180 |
| H4H10231P | 182 | 184 | 186 | 188 | 190 | 192 | 194 | 196 |
| H4H10232P | 198 | 200 | 202 | 204 | 206 | 208 | 210 | 212 |
| H4H10236P | 214 | 216 | 218 | 220 | 222 | 224 | 226 | 228 |
| H4H10237P | 230 | 232 | 234 | 236 | 238 | 240 | 242 | 244 |
| H4H10238P | 246 | 248 | 250 | 252 | 254 | 256 | 258 | 260 |
| H4H10250P | 262 | 264 | 266 | 268 | 270 | 272 | 274 | 276 |
| H4H10256P | 278 | 280 | 282 | 284 | 286 | 288 | 290 | 292 |
| H4H10270P | 294 | 296 | 298 | 300 | 302 | 304 | 306 | 308 |

Additional GCG antibodies or antibody fragments contemplated as useful herein include those disclosed in U.S. Pat. Nos. 4,206,199; 4,221,777; 4,423,034; 4,272,433; 4,407,965; 5,712,105; and PCT publications WO2007/124463 and WO2013/081993.

Antibody fragments include any fragment having the required target specificity, e.g. antibody fragments either produced by the modification of whole antibodies (e.g. enzymatic digestion), or those synthesized de novo using recombinant DNA methodologies (scFv, single domain antibodies, DVD (dual variable domain immunoglobulins), or dAbs (single variable domain antibodies)) or those identified using human phage or yeast display libraries (see, for example, McCafferty et al. (1990) Nature 348:552-554). Alternatively, antibodies can be isolated from mice producing human, human-mouse, human-rat, and human-rabbit chimeric antibodies using standard immunization and antibody isolation methods, including but not limited to making hybridomas, or using B cell screening technologies, such as SLAM. Immunoglobulin binding domains also include, but are not limited to, the variable regions of the heavy ($V_H$) or the light ($V_L$) chains of immunoglobulins. Or by immunizing people and isolating antigen positive B cells and cloning the cDNAs encoding the heavy and light chain and coexpressing them in a cell, such as CHO.

The term "antibody" as used herein refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant regions, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Within each IgG class, there are different isotypes (e.g. IgG1, IgG2, IgG3, IgG4). Typically, the antigen-binding region of an antibody will be the most critical in determining specificity and affinity of binding.

An exemplary immunoglobulin (antibody) structural unit comprises a tetramer. Each tetramer is composed of two identical pairs of polypeptide chains, each pair having one light chain (about 25 kD) and one heavy chain (about 50-70 kD). The N-terminus of each chain defines a variable region of about 100-110 or more amino acids primarily responsible for antigen recognition. The terms "variable light chain" ($V_L$) and variable heavy chain ($V_H$) refer to these light and heavy chains respectively.

Antibodies exist as intact immunoglobulins, or as a number of well-characterized fragments produced by digestion with various peptidases. For example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology.

Methods for preparing antibodies useful according to the methods herein are known to the art. See, for example, Kohler & Milstein (1975) Nature 256:495-497; Harlow & Lane (1988) Antibodies: A Laboratory Manual, Cold Spring Harbor Lab., Cold Spring Harbor, N.Y.). The genes encoding the heavy and light chains of an antibody of interest can be cloned from a cell, e.g., the genes encoding a monoclonal antibody can be cloned from a hybridoma and used to produce a recombinant monoclonal antibody. Monoclonal antibodies can be humanized using standard cloning of the CDR regions into a human scaffold. Gene libraries encoding human heavy and light chains of monoclonal antibodies can also be made from hybridoma or plasma cells. Random combinations of the heavy and light chain gene products generate a large pool of antibodies with different antigenic specificity. Techniques for the production of single chain antibodies or recombinant antibodies (U.S. Pat. Nos. 4,946,778; 4,816,567) can be adapted to produce antibodies used in the methods disclosed herein. Also, transgenic mice, or other organisms such as other mammals, may be used to express human, human-mouse chimeric, human-rat chimeric, human-rabbit chimeric, or humanized antibodies. Alternatively, phage display or yeast display technology can be used to identify human antibodies and heteromeric Fab fragments that specifically bind to selected antigens.

Immunoconjugates

The disclosure encompasses treatment of hyperammonemia with a human anti-GCGR monoclonal antibody (or human anti-GCG monoclonal antibody) conjugated to a therapeutic moiety ("immunoconjugate"), such as an agent that is capable of reducing blood ammonia levels or addressing another symptom of hyperammonemia. The type of therapeutic moiety that may be conjugated to the anti-GCGR antibody will take into account the condition to be treated and the desired therapeutic effect to be achieved. For example, in an effort to lower blood ammonia levels, and/or to maintain normal blood ammonia levels, an agent such as a glucagon receptor pathway antagonist, or a second GCGR inhibitor or GCG inhibitor may be conjugated to the GCGR antibody. Alternatively, if the desired therapeutic effect is to reduce glutamine or any other symptoms or conditions associated with a urea cycle disorder, it may be advantageous to conjugate an appropriate agent to the anti-GCGR antibody. Examples of suitable agents for forming immunoconjugates are known in the art.

Multi-Specific Antibodies

The antibodies useful according to the methods provided herein may be mono-specific, bi-specific, or multi-specific. Multi-specific antibodies may be specific for different epitopes of one target polypeptide or may contain antigen-binding domains specific for more than one target polypeptide. See, e.g., Tutt et al., (1991) J. Immunol. 147:60-69; Kufer et al., (2004) Trends Biotechnol. 22:238-244. The anti-GCGR antibodies can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multi-specific antibody with a second binding specificity. For example, bi-specific antibodies are contemplated where one arm of an immunoglobulin is specific for human GCGR or a fragment thereof, and the other arm of the immunoglobulin is specific for a second therapeutic target or is conjugated to a therapeutic moiety. In certain embodiments, one arm of an immunoglobulin is specific for an epitope on the N-terminal domain of hGCGR or a fragment thereof, and the other arm of the immunoglobulin is specific for an epitope on one of the EC loops of hGCGR, or a fragment thereof. In certain embodiments, one arm of an immunoglobulin is specific for one EC loop, or a fragment thereof, and the second arm is specific for a second EC loop, or a fragment thereof. In certain embodiments, one arm of an immunoglobulin is specific for one epitope on one EC loop of hGCGR and the other arm is specific for a second epitope on the same EC loop of hGCGR.

An exemplary bi-specific antibody format that can be used according to the methods described herein involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present disclosure.

Antibody Screening and Selection

Screening and selection of preferred antibodies, useful according to the methods provided herein, can be conducted by a variety of methods known to the art. Initial screening for the presence of monoclonal antibodies specific to a target antigen may be conducted through the use of ELISA-based methods, for example. A secondary screen is preferably conducted to identify and select a desired monoclonal antibody for use in construction of antibody-drug conjugates. Secondary screening may be conducted with any suitable method known to the art. One preferred method, termed "Biosensor Modification-Assisted Profiling" ("BiaMAP") is described in U.S. Publication 2004/0101920, herein specifically incorporated by reference in its entirety. BiaMAP allows rapid identification of hybridoma clones producing monoclonal antibodies with desired characteristics. More specifically, monoclonal antibodies are sorted into distinct epitope-related groups based on evaluation of antibody:antigen interactions. Antibodies capable of blocking either a ligand or a receptor may be identified by a cell based assay, such as a luciferase assay utilizing a luciferase gene under the control of an NFκB driven promoter or cAMP response driven promoter. Stimulation of the GCGR by glucagon leads to a signal through NFκB/cAMP/CREB thus increasing luciferase levels in the cell. Blocking antibodies are identified as those antibodies that blocked glucagon induction of luciferase activity.

Treatment Population

The therapeutic methods provided herein are useful for treating individuals with a urea cycle disorder or a condition or disease associated with hyperammonemia. In some embodiments, the subject suffers from congenital hyperammonemia, e.g. a defect in a urea cycle enzyme selected from the group consisting of carbamyl phosphate synthetase (CPS1), N-acetylglutamate synthetase (NAGS), ornithine transcarbamylase (OTC), argininosuccinic acid synthetase (ASS), argininosuccinate lyase (ASL), and arginase (AR1); or a defect in a urea cycle transporter selected from ornithine translocase (ORNT1) and citrin. Other congenital disorders which cause hyperammonemia include Propionic acidemia, Isolated methylmalonic acidemia, Isovaleric acidemia, Carbonic anhydrase VA deficiency, Lysinuric protein intolerance, carnitine palmitoyl transferase II deficiency, carnitine-acylcarnitine translocase, pyrroline-5-carboxylate synthetase deficiency, pyruvate carboxylase deficiency, ornithine aminotransferase deficiency, carbonic anhydrase Va deficiency, hyperinsulinism-hyperammonemia syndrome, mitochondrial disorders, glutamine synthetase deficiency, fatty acid oxidation disorders (for example, Short-Chain Acyl-CoA Dehydrogenase Deficiency, Medium-Chain Acyl-Coenzyme A Dehydrogenase Deficiency, Multiple Acyl-Coenzyme A Dehydrogenase Deficiency, Very Long-Chain Acyl-Coenzyme A Dehydrogenase Deficiency), and Hyperinsulinism-hyperammonemia syndrome (Familial Hyperinsulinism).

In some embodiments, the hyperammonemia is acquired, e.g. is caused by liver disease and complications thereof; is caused by treatment with a therapeutic agent (L-asparaginase or pegaspargase), 5-pentanoic acid, valproic acid, a corticosteroid, or a cyclophosphamide; or is caused by herpes simplex infection or hepatitis B infection. Additional causes of hyperammonemia, i.e. acquired hyperammonemia, include liver disease and complications thereof, e.g., hepatic encephalopathy in subjects with advanced liver disease, fetor hepaticus (a late sign of liver failure), vascular bypass of the liver, and biliary atresia; administration of toxic levels of valproic acid, corticosteroid, or cyclophosphamide; herpes simplex infection; and gastrointestinal bacterial overgrowth. Hyperammonemia can also be caused by infection with urease-producing organisms.

Furthermore, hyperammonemia can be caused by total parenteral nutrition (with relative arginine deficiency), nutritional carnitine deficiency, cystoscopy with glycine-containing solutions, post-lung/bone marrow transplantation, vascular malformations, or transient hyperammonemia of the newborn.

In some embodiments, elevated levels of ammonia is detected in the subject sera. In some embodiments, excess glutamine is detected in the subject sera.

Therapeutic Administration and Formulations

Useful according to the methods provided herein are therapeutic compositions comprising a glucagon/GCGR antagonist, such as, for example, an anti-GCGR antibody. The administration of therapeutic compositions in accordance with the methods described herein will be administered via a suitable route including, but not limited to, intravenously, subcutaneously, intramuscularly, intrathecally, intracerebrally, intraventricularly, intranasally, or orally, with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. When the antibody is used for treating hyperammonemia or lowering blood ammonia levels associated with a urea cycle disorder, in a subject, it is advantageous to intravenously administer the antibody normally at a dose of about 0.01 to about 30 mg/kg body weight, more preferably about 0.02 to about 7, about 0.03 to about 5, or about 0.05 to about 3 mg/kg body weight. Depending on the severity of the condition and response to treatment, the frequency and the duration of the treatment can be adjusted. In certain embodiments, the antibody or antigen-binding fragment thereof can be administered as an initial dose of at least about 0.1 mg to about 800 mg, about 1 to about 500 mg, about 5 to about 300 mg, or about 10 to about 200 mg, to about 100 mg, or to about 50 mg.

In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks; or until the hyperammonemia is resolved.

Various delivery systems are known and can be used to administer the pharmaceutical composition comprising the antibody, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, depot formulations, aerosol, intradermal, transdermal, intramuscular, intraperitoneal, intravenous, subcutaneous, intranasal, epidural, intrathecal, intraventricular, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can be also delivered in a vesicle, in particular a liposome (see, for example, Langer (1990) Science 249:1527-1533).

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition useful herein can be delivered subcutaneously or intravenously with a standard needle and syringe. In addition, with respect to subcutaneous delivery, a pen delivery device readily has applications in delivering a pharmaceutical composition useful in the methods described herein. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition useful according to the methods described herein. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70130™ pen (Eli Lilly and Co., Indianapolis, Inn.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition useful according to the methods described herein include, but certainly are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.) and the HUMIRA™ Pen (Abbott Labs, Abbott Park, Ill.), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 750 mg per dosage form in a unit dose; especially in the form of injection, it is preferred that the aforesaid antibody is contained in about 5 to about 100 mg and in about 10 to about 250 mg for the other dosage forms.

Combination Therapies

In numerous embodiments, the GCG inhibitors or GCGR antagonists useful herein may be administered in combination with one or more additional compounds, therapeutic agents, or therapies. Combination therapy may be simultaneous (or concomitant) or sequential. In some aspects, the additional compound (or therapeutic agent) is formulated into the same pharmaceutical composition as the GCG inhibitor or GCGR antagonist. In some aspects, the additional compound is administered separately, before, after, or concomitantly with administration of the GCG inhibitor or the GCGR antagonist.

In some embodiments, the glucagon signaling pathway antagonist is administered with at least one additional therapeutic agent selected from the following: insulin, a nonabsorbable antibiotic (rifaximin or lactulose), sodium phenylbutyrate, sodium benzoate, sodium phenylacetate, glycerol phenylbutyrate, carbamyl glutamate (Carbaglu®), a second GCG inhibitor, and a second GCGR antagonist. In some embodiments, the glucagon signaling pathway antagonist is administered with hemodialysis or continuous renal replacement. In some embodiments, the glucagon signaling pathway antagonist is administered with L-citrulline or L-arginine free base. In some embodiments, the glucagon signaling pathway antagonist is administered with antioxidants or electrolytes. In some embodiments, the glucagon signaling pathway antagonist is administered with amino acid formulas selected from Cyclinex, EAA, UCD I&II, and individual branched chain amino acids.

The additional therapeutically active component(s) may be administered prior to, concurrent with, or after the administration of the glucagon signaling pathway antagonist, e.g. the GCG inhibitor or the GCGR antagonist. For purposes of the present disclosure, such administration regimens are considered the administration of a glucagon signaling pathway antagonist "in combination with" a second therapeutically active component.

Administration Regimens

According to certain embodiments described herein, multiple doses of the glucagon/GCGR signaling pathway antagonist may be administered to a subject over a defined time course. The methods comprise sequentially administering to a subject multiple doses of a glucagon/GCGR signaling pathway antagonist. As used herein, "sequentially administering" means that each dose of the antagonist is administered to the subject at a different point in time, e.g., on different days separated by a predetermined interval (e.g., hours, days, weeks or months). The methods described herein comprise sequentially administering to the subject a single initial dose of the glucagon/GCGR signaling pathway antagonist, followed by one or more secondary doses of the glucagon/GCGR signaling pathway antagonist, and optionally followed by one or more tertiary doses of the glucagon/GCGR signaling pathway antagonist.

The terms "initial dose," "secondary doses," and "tertiary doses," refer to the temporal sequence of administration of an glucagon/GCGR signaling pathway antagonist useful herein. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the glucagon/GCGR signaling pathway antagonist, but generally may differ from one another in terms of frequency of administration. In certain embodiments, however, the amount of the glucagon/GCGR signaling pathway antagonists contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

Pharmaceutical Compositions

The methods disclosed herein contemplate the use of pharmaceutical compositions comprising at least a therapeutically effective amount of an active agent useful in treating hyperammonemia or a urea cycle disorder, such as a glucagon signaling pathway antagonist, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

In one embodiment, the composition is formulated in accordance with routine procedures as a pharmaceutical composition adapted for intravenous administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The active agents useful according to the methods described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the active agent which will be effective in the treatment of hyperammonemia can be determined by standard clinical techniques based on the present description. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. However, suitable dosage ranges for intravenous administration are generally about 20 micrograms to 2 grams of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds that are sufficient to maintain therapeutic effect. In cases of local administration or selective uptake, the effective local concentration of the compounds may not be related to plasma concentration. One having skill in the art will be able to optimize therapeutically effective local dosages without undue experimentation.

The amount of compound administered will, of course, be dependent on the subject being treated, on the subject's weight, the severity of the affliction, the manner of administration, and the judgment of the prescribing physician. The therapy may be repeated intermittently while symptoms are detectable or even when they are not detectable. The therapy may be provided alone or in combination with other drugs.

Kits

Also provided herein is an article of manufacturing comprising packaging material and a pharmaceutical agent contained within the packaging material, wherein the pharmaceutical agent comprises at least one glucagon signaling pathway antagonist useful according to the methods disclosed herein, and wherein the packaging material comprises a label or package insert which indicates that the glucagon signaling pathway antagonist can be used for treating a urea cycle disorder or a condition or disease characterized by hyperammonemia.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

EXAMPLES

The following examples are provided such that those of ordinary skill in the art have a complete disclosure and description of how to implement the methods disclosed herein. Efforts have been made to ensure accuracy with respect to numbers used (e.g., amounts, temperature, etc.) but some experimental errors and deviations should be accounted for. Unless indicated otherwise, parts are by weight, molecular weight is average molecular weight, temperature is in degrees Centigrade, and pressure is at or near atmospheric.

Example 1: Evaluation of a GCGR Antagonist (H4H1327P) in a Mouse Model of Urea Cycle Disorder The effects of mAb1, a GCGR monoclonal antibody having a HCVR/LCVR amino acid sequence pair of SEQ ID NOs: 86/88 (H4H1327P), on body weight, survival rate, plasma ammonia levels and blood glucose levels were determined in ornithine transcarbamylase mutant ($Otc^{spf-ash}$) mice, a mouse model of urea cycle disorder. $Otc^{spf-ash}$ mutation is a G to A missense transition of the last nucleotide of exon 4 in mouse Otc gene. The mutation changes an arginine to histidine (R129H) and results in inefficient mRNA splicing at this site and a site located 48 bases into the adjacent intron. The allele is hypomorphic and leads to 5-10% retention of wild-type hepatic ornithine transcarbamylase enzyme activity. The Otc mutant mice are viable, fertile, and do not show overt sickness, but are smaller than wild-type mice. It has been shown that high protein (40% as opposed to 21% in regular chow) diet in Otc mutant mice causes hyperammonemia and 30% lethality in one week (Yang et al., A dual AAV system enables the Cas9-mediated correction of a metabolic liver disease in newborn mice. *Nat Biotechnol.* 2016 34: 334-8). In this experiment, Otc mutant mice were placed on 30% protein to induce mild hyperammonemia and 60% lethality in 9 weeks.

Figure 2:
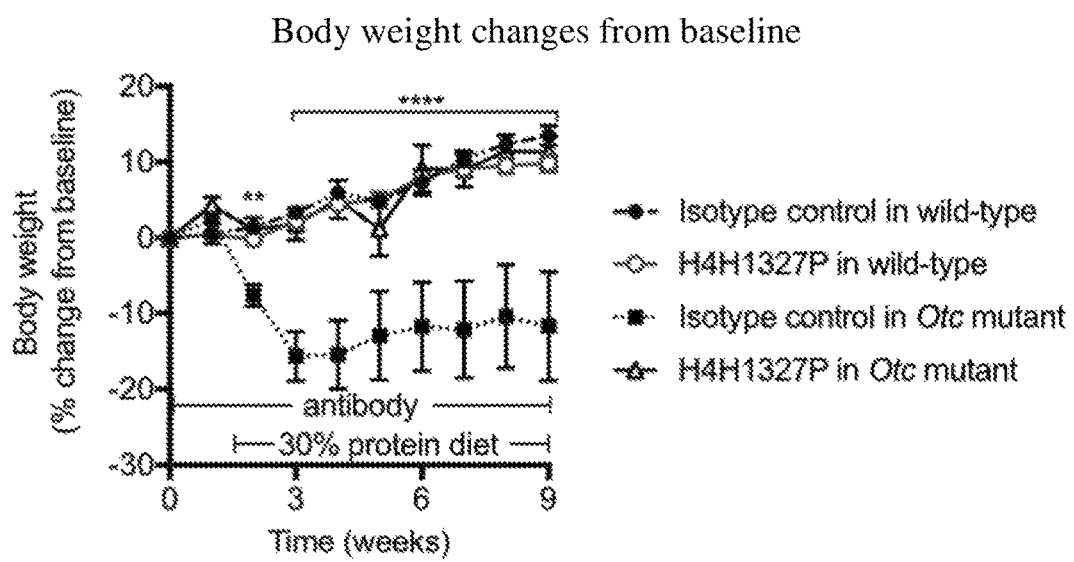
FIG. 2 is a graphical representation of Table 4, and depicts mean±SEM of body weight changes from baseline for the four groups of mice.
Figure 3:
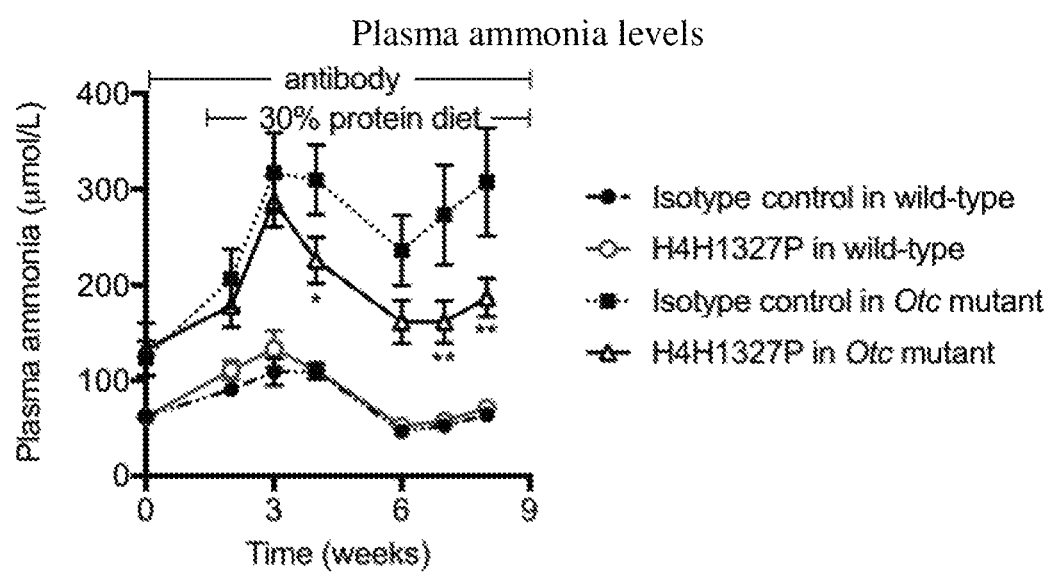
FIG. 3 is a graphical representation of Table 5, and depicts mean±SEM plasma ammonia levels for the four groups of mice at baseline and weeks 2, 3, 4, 6, 7, and 8.
Figure 4:
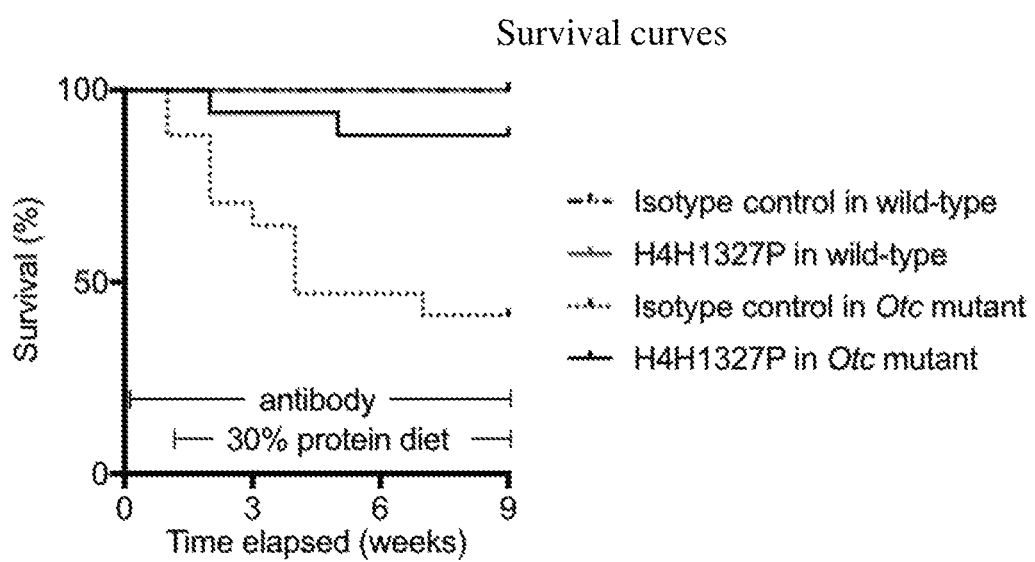
FIG. 4 depicts survival curves for the four groups of mice.

Forty-one wild-type mice and thirty-four Otc mutant mice were used in this study. To establish a baseline for blood glucose measurements, non-fasted blood glucose was tested in blood collected from the tail of each mouse using an ACCU-CHEK® Compact Plus (Roche) at 9:00 AM on day 0. The wild-type and Otc mutant were each sorted into 2 treatment groups based on their blood glucose level so that the mean glucose level across treatment groups was approximately equal. From day 0 to the end of the study, half of the wild-type (n=21) and Otc mutant (n=17) mice received weekly subcutaneous injections of mAb1 at 10 mg/kg, whereas the other half of wild-type (n=20) and Otc mutant (n=17) mice received weekly subcutaneous injections of hIgG4 isotype control at 10 mg/kg. All mice were placed on high protein diet (30% protein by weight) from day 10 for the duration of study. Non-fasting blood glucose and body weights were measured weekly. Mean±SEM of blood glucose levels at each time point was calculated for each group and shown in Table 3 and FIG. 1. Mean±SEM of body weight changes from baseline (day 0) at each time point was calculated for each group shown in Table 4 and FIG. 2. Plasma was collected at baseline and weeks 2, 3, 4, 6, 7, and 8 to determine ammonia levels. Mean±SEM of plasma ammonia levels at each time point was calculated for each group and shown in Table 5 and FIG. 3. Deaths of animals were recorded daily. Survival curve of each group is shown in FIG. 4. For blood glucose, body weight, and plasma ammonia, statistical analyses were performed by two-way ANOVA comparing each treatment group within each genotype, followed by Bonferroni post-tests.

Results and Conclusions:

mAb1-treated wild-type mice and Otc mutant mice showed reductions in blood glucose compared to isotype control-administered animals post mAb1 administration (between weeks 1 and 9), confirming glucose lowering efficacy of mAb1 (Table 3 and FIG. 1). High protein diet induced about 15% body weight loss in isotype-control administered Otc mutant mice, whereas mAb1-administered Otc mutant mice were protected from the diet induced weight loss (Table 4 and FIG. 2). High protein diet-induced elevations in plasma ammonia levels were smaller in mAb1-treated Otc mutant mice compared to isotype-control administered Otc mutant mice (Table 5 and FIG. 3). None of the wild-type mice, regardless of the treatment, died during the study. At the end of study, 88% (15 out 17) of mAb1-treated Otc mutant mice were alive, whereas 47% (8 out of 17) of isotype-control administered Otc mutant mice were alive (FIG. 4).

These data suggest that mAb1 confers protection against hyperammonemia, excessive weight loss, and deaths in Otc mutant mice on high protein diet, in a mouse model of urea cycle disorders.

TABLE 3

Blood glucose levels

| | Time (weeks) | Isotype control in wild-type mice | mAb1 in wild-type mice | Isotype control in Otc mutant mice | mAb1 in Otc mutant mice |
|---|---|---|---|---|---|
| Blood glucose (mg/dL) | 0 | 182 ± 3 | 184 ± 2 | 186 ± 6 | 187 ± 4 |
| | 1 | 186 ± 4 | 133 ± 2 | 189 ± 5 | 129 ± 2 |
| | 2 | 193 ± 4 | 141 ± 2 | 189 ± 7 | 146 ± 2 |
| | 3 | 188 ± 3 | 135 ± 2 | 150 ± 10 | 132 ± 4 |
| | 4 | 174 ± 3 | 133 ± 3 | 155 ± 11 | 135 ± 3 |
| | 5 | 168 ± 3 | 131 ± 3 | 147 ± 10 | 131 ± 3 |
| | 6 | 172 ± 3 | 129 ± 3 | 147 ± 10 | 127 ± 4 |
| | 7 | 177 ± 4 | 138 ± 3 | 148 ± 9 | 132 ± 4 |
| | 8 | 167 ± 3 | 133 ± 3 | 154 ± 15 | 134 ± 4 |
| | 9 | 176 ± 2 | 135 ± 3 | 154 ± 14 | 132 ± 3 |

TABLE 4

Body weight changes from baseline

| | Time (weeks) | Isotype control in wild-type mice | mAb1 in wild-type mice | Isotype control in Otc mutant mice | mAb1 in Otc mutant mice |
|---|---|---|---|---|---|
| Body weight (% change from baseline) | 0 | 0.0 ± 0.0 | 0.0 ± 0.0 | 0.0 ± 0.0 | 0.0 ± 0.0 |
| | 1 | 0.6 ± 1.4 | 0.4 ± 0.4 | 2.5 ± 0.6 | 4.4 ± 1.1 |
| | 2 | 1.4 ± 0.7 | −0.1 ± 0.6 | −7.6 ± 1.4 | 1.1 ± 1.6 |
| | 3 | 3.4 ± 0.7 | 2.3 ± 0.6 | −15.6 ± 3.2 | 1.9 ± 2.1 |
| | 4 | 6.0 ± 0.7 | 4.6 ± 0.6 | −15.4 ± 4.5 | 5.1 ± 2.5 |
| | 5 | 4.8 ± 0.9 | 5.1 ± 1.0 | −12.9 ± 5.8 | 1.2 ± 3.7 |
| | 6 | 7.3 ± 1.7 | 8.1 ± 1.0 | −11.7 ± 5.8 | 9.2 ± 3.1 |
| | 7 | 10.5 ± 1.0 | 9.1 ± 1.1 | −12.1 ± 6.4 | 9.0 ± 2.2 |
| | 8 | 12.4 ± 1.1 | 9.6 ± 1.0 | −10.4 ± 6.8 | 11.5 ± 2.2 |
| | 9 | 13.5 ± 1.3 | 9.9 ± 1.1 | −11.7 ± 7.2 | 11.3 ± 2.1 |

TABLE 5

Plasma ammonia levels

| | Time (weeks) | Isotype control in wild-type mice | mAb1 in wild-type mice | Isotype control in Otc mutant mice | mAb1 in Otc mutant mice |
|---|---|---|---|---|---|
| Plasma ammonia (μmol/L) | 0 | 63 ± 5 | 62 ± 5 | 123 ± 18 | 132 ± 28 |
| | 2 | 90 ± 8 | 110 ± 10 | 207 ± 31 | 178 ± 23 |
| | 3 | 109 ± 14 | 133 ± 19 | 317 ± 41 | 288 ± 27 |
| | 4 | 110 ± 8 | 111 ± 7 | 310 ± 36 | 226 ± 24 |
| | 6 | 47 ± 2 | 52 ± 4 | 236 ± 37 | 161 ± 23 |
| | 7 | 52 ± 3 | 57 ± 3 | 273 ± 52 | 161 ± 22 |
| | 8 | 64 ± 3 | 71 ± 3 | 308 ± 56 | 187 ± 20 |

A second, differently designed study was performed, as follows, to determine the effect of H4H1327P on mice with a urea cycle disorder.

The effects of H4H1327P on plasma ammonia levels, survival rate, body weight, and blood glucose levels were determined in ornitine transcarbamylase mutant ($Otc^{spf\text{-}ash}$) mice, a mouse model of urea cycle disorder. Ornitine transcarbamylase mutant ($Otc^{sPf\text{-}ash}$) mice were placed on high protein diet (30% as opposed to 21% in regular chow) first. Two days post the diet initiation, development of mild hyperammonemia was confirmed in the Otc mutant mice, before antibody administrations initiated.

Figure 5:
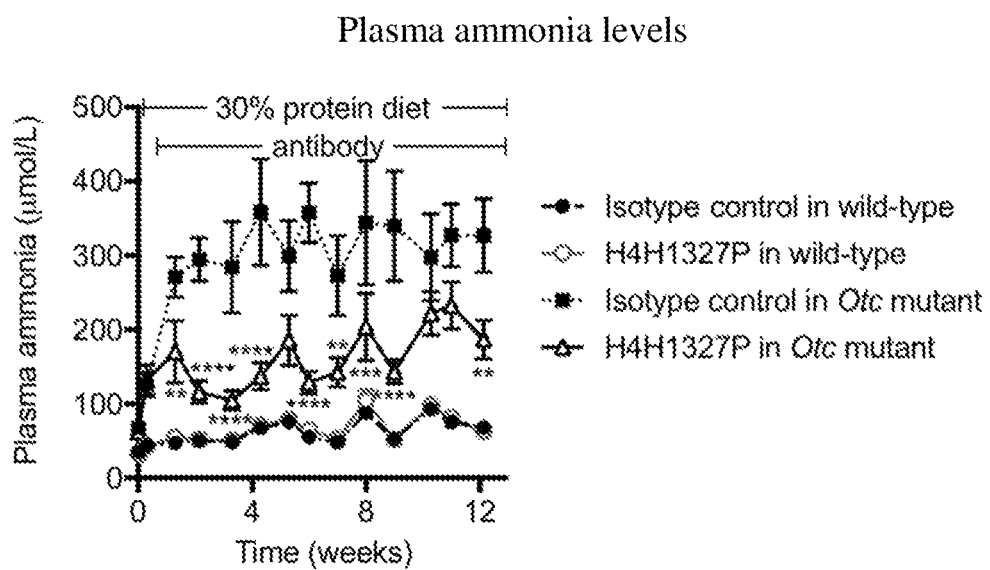
FIG. 5 shows the plasma ammonia levels over time of wild-type and Otc mutant mice on a 30% protein diet treated with isotype control or H4H1327P antibody. : $p<0.01$ between the two treatments in Otc mutant mice, *: $p<0.001$ between the two treatments in Otc mutant mice, ****: $p<0.0001$ between the two treatments in Otc mutant mice.
Figure 6:
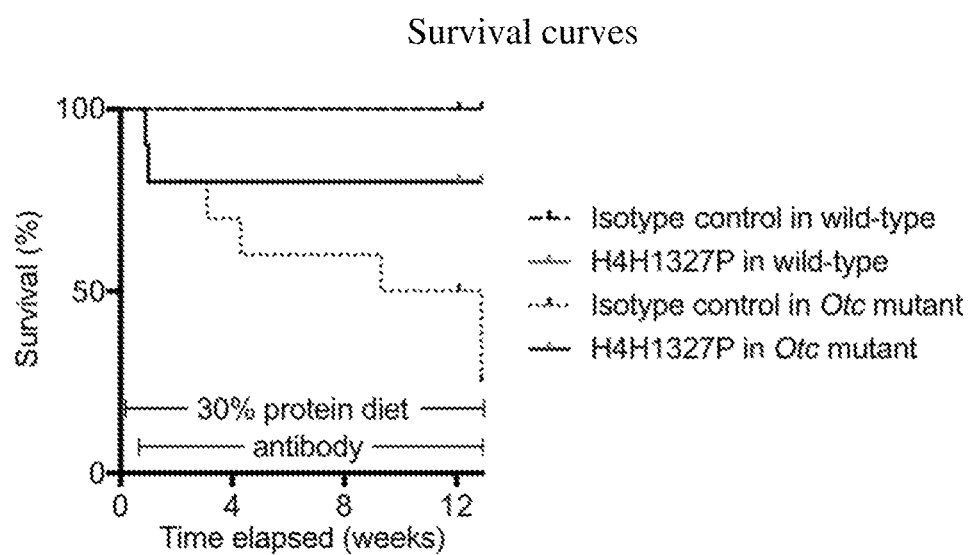
FIG. 6 depicts survival curves for wild-type and Otc mutant mice on a 30% protein diet treated with isotype control or H4H1327P antibody.
Figure 8:
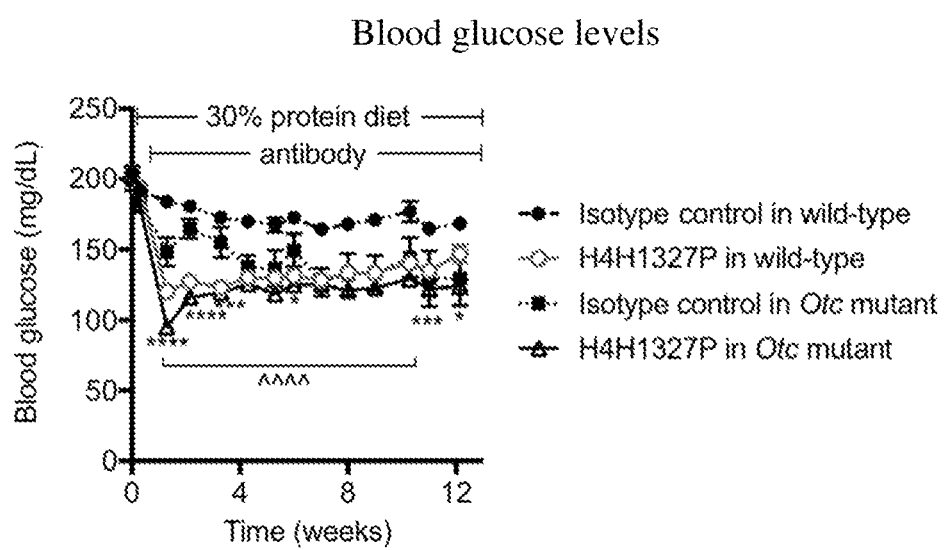
FIG. 8 shows blood glucose levels (mg/dL) over time of wild-type and Otc mutant mice on a 30% protein diet treated with isotype control or H4H1327P antibody. *: $p<0.05$ between the two treatments in Otc mutant mice, *: $p<0.001$ between the two treatments in Otc mutant mice, **: $p<0.0001$ between the two treatments in Otc mutant mice, ^^^^: $p<0.0001$ between the two treatments in wild-type mice.

Twenty wild-type mice and twenty Otc mutant mice were used in this study. To establish a baseline for plasma ammonia measurements, non-fasted ammonia level was tested in plasma collected from the submandibular gland of each mouse using ADVIA® 1800 blood chemistry analyzer (Bayer, Leverkusen, Germany) at 9:00 AM on day 0. All mice were placed on high protein diet (30% protein by weight) from day 0 for the duration of study. The wild-type and Otc mutants were each sorted into 2 treatment groups based on their plasma ammonia level on day 2 so that the mean ammonia level of each treatment group in each genotype was approximately equal. From day 2 to the end of the study, a half of wild-type (n=10) and Otc mutant (n=10) mice received weekly subcutaneous injections of H4H1327P at 10 mg/kg, whereas the other half of wild-type (n=10) and Otc mutant (n=10) mice received weekly subcutaneous injections of hIgG4 isotype control at 10 mg/kg. Plasma was collected at baseline, day 2 and thereafter every 5 to 12 days to determine ammonia levels. Mean±SEM of plasma ammonia levels at each time point was calculated for each group and shown in Table 6 and FIG. 5. Deaths of animals were recorded daily. Survival curves of each group are shown in FIG. 6. Body weights and non-fasting blood glucose were measured weekly. Mean±SEM of body weight changes from baseline (day 0) at each time point was calculated for each group and shown in Table 7 and FIG. 8. Mean±SEM of blood glucose levels at each time point was calculated for each group and shown in Table 8 and FIG. 8. For blood glucose, body weight, and plasma ammonia, statistical analyses were performed by two-way ANOVA comparing each treatment groups within each genotype, followed by Bonferroni post-tests.

Figure 7:
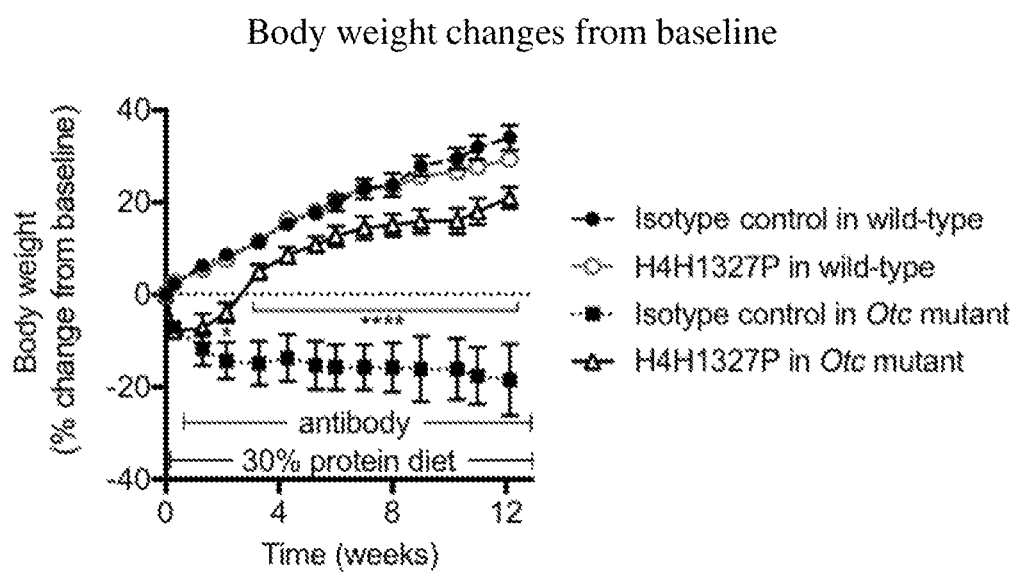
FIG. 7 shows body weight changes over time from baseline of wild-type and Otc mutant mice on a 30% protein diet treated with isotype control or H4H1327P antibody. *: $p<0.05$ between the two treatments in Otc mutant mice, ****: $p<0.0001$ between the two treatments in Otc mutant mice.

High protein diet increased plasma ammonia levels in Otc mutant mice from 65.2 to 129.4 µmol/L in two days. Otc mutant mice administered with isotype-control showed further elevated mean plasma ammonia levels of 271-359 mol/L, whereas mean plasma ammonia levels in H4H1327P-adminisited Otc mutant mice remained within 105-232 µmol/L for the duration of the study (Table 6 and FIG. 5). At the end of the study, 80% (8 out 10) of H4H1327P-treated Otc mutant mice were alive, whereas 40% (4 out of 10) of isotype-control administered Otc mutant mice were alive (FIG. 6). None of the wild-type mice, regardless of the treatment, died during the study. High protein diet induced 18.5% body weight loss in isotype-control administered Otc mutant mice, whereas H4H1327P-administered Otc mutant mice showed 20.9% increases in body weight at the end of the study (Table 7 and FIG. 7). H4H1327P-treated wild-type mice and Otc mutant mice showed reductions in blood glucose compared to isotype control-administered animals post H4H1327P administration, confirming glucose lowering efficacy of H4H1327P (Table 8 and FIG. 8).

In summary, H4H1327P was able to ameliorate hyperammonemia, excessive weight loss, and deaths, triggered by high protein diet in Otc mutant mice. These data indicate that H4H1327P is a useful option for patients with urea cycle disorders.

TABLE 6

Plasma ammonia levels

| | Time (weeks) | Isotype control in wild-type mice | H4H1327P in wild-type mice | Isotype control in Otc mutant mice | H4H1327P in Otc mutant mice |
|---|---|---|---|---|---|
| Plasma ammonia (µmol/L) | 0 | 35 ± 2 | 32 ± 1 | 68 ± 8 | 63 ± 7 |
| | 0.3 | 44 ± 3 | 44 ± 3 | 126 ± 16 | 133 ± 20 |
| | 1.3 | 47 ± 3 | 55 ± 3 | 271 ± 27 | 170 ± 42 |
| | 2.1 | 50 ± 1 | 52 ± 3 | 295 ± 29 | 116 ± 15 |
| | 3.3 | 49 ± 2 | 50 ± 5 | 284 ± 61 | 105 ± 13 |
| | 4.3 | 68 ± 5 | 71 ± 5 | 359 ± 72 | 137 ± 18 |
| | 5.3 | 76 ± 4 | 79 ± 7 | 299 ± 48 | 186 ± 33 |
| | 6.0 | 55 ± 5 | 64 ± 9 | 358 ± 40 | 129 ± 15 |
| | 7.0 | 49 ± 2 | 53 ± 3 | 273 ± 54 | 143 ± 19 |
| | 8.0 | 88 ± 8 | 105 ± 14 | 344 ± 84 | 204 ± 45 |
| | 9.0 | 53 ± 3 | 52 ± 2 | 340 ± 74 | 144 ± 16 |
| | 10.3 | 93 ± 8 | 98 ± 8 | 298 ± 58 | 222 ± 29 |
| | 11.0 | 76 ± 7 | 81 ± 6 | 327 ± 42 | 233 ± 32 |
| | 12.1 | 68 ± 9 | 63 ± 3 | 327 ± 50 | 187 ± 26 |

TABLE 7

Body weight changes from baseline

| | Time (weeks) | Isotype control in wild-type mice | H4H1327P in wild-type mice | Isotype control in Otc mutant mice | H4H1327P in Otc mutant mice |
|---|---|---|---|---|---|
| Body weight (% change from baseline) | 0 | 0.0 ± 0.0 | 0.0 ± 0.0 | 0.0 ± 0.0 | 0.0 ± 0.0 |
| | 0.3 | 2.2 ± 0.4 | 2.7 ± 0.5 | −7.0 ± 1.2 | −7.8 ± 1.0 |
| | 1.3 | 6.3 ± 0.5 | 5.4 ± 0.3 | −11.8 ± 3.6 | −7.3 ± 3.2 |
| | 2.1 | 8.6 ± 0.8 | 7.6 ± 0.7 | −14.3 ± 4.0 | −3.9 ± 2.2 |
| | 3.3 | 11.4 ± 1.0 | 11.5 ± 0.8 | −14.8 ± 4.8 | 4.9 ± 1.6 |
| | 4.3 | 15.3 ± 1.4 | 16.1 ± 1.2 | −13.7 ± 5.0 | 8.5 ± 1.8 |
| | 5.3 | 17.6 ± 1.3 | 17.9 ± 0.9 | −15.3 ± 5.2 | 10.9 ± 1.8 |
| | 6.0 | 19.8 ± 1.7 | 20.6 ± 1.0 | −15.7 ± 4.9 | 12.6 ± 2.1 |
| | 7.0 | 22.9 ± 2.2 | 23.2 ± 0.9 | −15.7 ± 4.9 | 14.5 ± 2.5 |
| | 8.0 | 23.7 ± 2.5 | 23.2 ± 1.3 | −15.8 ± 5.3 | 15.1 ± 2.4 |
| | 9.0 | 27.8 ± 2.2 | 25.6 ± 1.1 | −16.1 ± 7.1 | 15.8 ± 2.6 |

TABLE 7-continued

Body weight changes from baseline

| Time (weeks) | Isotype control in wild-type mice | H4H1327P in wild-type mice | Isotype control in Otc mutant mice | H4H1327P in Otc mutant mice |
|---|---|---|---|---|
| 10.3 | 29.4 ± 2.3 | 26.6 ± 0.7 | −16.1 ± 6.6 | 15.9 ± 2.7 |
| 11.0 | 31.9 ± 2.6 | 27.7 ± 1.3 | −17.6 ± 6.1 | 18.0 ± 2.9 |
| 12.1 | 34.0 ± 2.7 | 29.3 ± 1.2 | −18.5 ± 7.7 | 20.9 ± 2.3 |

TABLE 8

Blood glucose levels

| | Time (weeks) | Isotype control in wild-type mice | H4H1327P in wild-type mice | Isotype control in Otc mutant mice | H4H1327P in Otc mutant mice |
|---|---|---|---|---|---|
| Blood glucose (mg/dL) | 0 | 204 ± 6 | 204 ± 4 | 199 ± 7 | 204 ± 5 |
| | 0.3 | 192 ± 4 | 194 ± 4 | 184 ± 6 | 182 ± 6 |
| | 1.3 | 184 ± 4 | 120 ± 2 | 148 ± 10 | 95 ± 5 |
| | 2.1 | 181 ± 4 | 127 ± 2 | 165 ± 7 | 116 ± 4 |
| | 3.3 | 173 ± 5 | 123 ± 2 | 155 ± 11 | 119 ± 5 |
| | 4.3 | 170 ± 3 | 130 ± 3 | 138 ± 8 | 126 ± 5 |
| | 5.3 | 167 ± 5 | 130 ± 2 | 137 ± 12 | 118 ± 4 |
| | 6.0 | 172 ± 4 | 131 ± 2 | 150 ± 12 | 125 ± 4 |
| | 7.0 | 164 ± 3 | 128 ± 3 | 127 ± 10 | 125 ± 3 |
| | 8.0 | 168 ± 3 | 134 ± 2 | 132 ± 15 | 121 ± 3 |
| | 9.0 | 171 ± 4 | 133 ± 2 | 133 ± 13 | 123 ± 4 |
| | 10.3 | 177 ± 7 | 140 ± 2 | 144 ± 14 | 129 ± 4 |
| | 11.0 | 165 ± 3 | 135 ± 3 | 129 ± 20 | 122 ± 5 |
| | 12.1 | 168 ± 4 | 147 ± 6 | 130 ± 19 | 124 ± 5 |

What is claimed is:

1. A method for treating hyperammonemia in a subject in need thereof, the method comprising administering, to the subject, a therapeutically effective amount of a composition comprising a glucagon signaling pathway antagonist such that,
   plasma ammonia levels in the subject are decreased by at least about 9% to about 64% for at least about 7 days after the administration relative to an untreated subject, hyperammonemia is mediated, and
   at least one symptom or complication associated with hyperammonemia is alleviated or reduced in severity, wherein the hyperammonemia is associated with a defect in one or more urea cycle enzymes selected from the group consisting of carbamyl phosphate synthetase (CPS1), N-acetylglutamate synthetase (NAGS), ornithine transcarbamylase (OTC), argininosuccinic acid synthetase (ASS), argininosuccinate lyase (ASL), and arginase (AR1), or associated with glutamine synthetase deficiency.

2. The method of claim 1, wherein the hyperammonemia is acquired.

3. The method of claim 1, wherein the hyperammonemia is congenital hyperammonemia.

4. The method of claim 1, wherein the glucagon signaling pathway antagonist is an isolated human monoclonal antibody or antigen-binding fragment thereof that specifically binds glucagon receptor, and wherein the isolated human monoclonal antibody or antigen-binding fragment thereof comprises a heavy chain complementarity determining region (HCDR) 1, HCDR2, and HCDR3 within a heavy chain variable region (HCVR) amino acid sequence as set forth in SEQ ID NO: 86; and a light chain complementarity determining region (LCDR) 1, LCDR2, and LCDR3 within a light chain variable region (LCVR) amino acid sequence as set forth in SEQ ID NO: 88.

5. The method of claim 1, wherein the composition is administered to the subject in combination with at least one additional therapeutic agent or supplement.

6. The method of claim 1, wherein the glucagon signaling pathway antagonist is administered concomitantly with:
   (i) one or more amino acid formulas selected from Cyclinex, EAA, UCD-I, UCD-II, and individual branched chain amino acids;
   (ii) antioxidants and/or electrolytes;
   (iii) L-citrulline and/or L-arginine free base;
   (iv) hemodialysis and/or continuous renal replacement; and/or
   (v) a non-absorbable antibiotic, rifaximin, lactulose, sodium phenylbutyrate, sodium benzoate, sodium phenylacetate, glycerol phenylbutyrate, carbamyl glutamate, a second GCG inhibitor, and/or a second GCGR antagonist.

7. A method of treating a subject with a urea cycle disorder, wherein the subject exhibits elevated levels of ammonia, the method comprising administering to the subject a therapeutically effective amount of a composition comprising a glucagon signaling pathway antagonist, and wherein plasma ammonia levels in the subject are decreased by at least about 9% to about 64% for at least about 7 days after the administration relative to an untreated subject.

8. The method of claim 7, wherein the subject having a urea cycle disorder suffers from:
   (i) one or more defects in a urea cycle enzyme selected from the group consisting of carbamyl phosphate synthetase (CPS1), N-acetylglutamate synthetase (NAGS), ornithine transcarbamylase (OTC), argininosuccinic acid synthetase (ASS), argininosuccinate lyase (ASL), and arginase (AR1); and/or
   (ii) one or more defects in a urea cycle transporter selected from ornithine translocase (ORNT1) and citrin.

9. The method of claim 7, wherein the glucagon signaling pathway antagonist is an isolated human monoclonal antibody or antigen-binding fragment thereof that specifically binds glucagon receptor, wherein the antibody or antigen-binding fragment thereof comprises a heavy chain complementarity determining region (HCDR) 1, HCDR2, and HCDR3 within a heavy chain variable region (HCVR) amino acid sequence as set forth in SEQ ID NO: 86; and a light chain complementarity determining region (LCDR) 1, LCDR2, and LCDR3 within a light chain variable region (LCVR) amino acid sequence as set forth in SEQ ID NO: 88.

10. The method of claim 7, wherein the composition is administered to the subject in combination with at least one additional therapeutic agent or supplement.

11. The method of claim 7, wherein the glucagon signaling pathway antagonist is administered concomitantly with:
   (i) one or more amino acid formulas selected from Cyclinex, EAA, UCD-I, UCD-II, and individual branched chain amino acids;
   (ii) antioxidants and/or electrolytes;
   (iii) L-citrulline and/or L-arginine free base;
   (iv) hemodialysis and/or continuous renal replacement; and/or
   (v) a non-absorbable antibiotic, rifaximin, lactulose, sodium phenylbutyrate, sodium benzoate, sodium phenylacetate, glycerol phenylbutyrate, carbamyl glutamate, a second GCG inhibitor, and/or a second GCGR antagonist.

12. A method of treating hyperammonemia in a subject in need thereof, comprising administering to the subject a therapeutically effective amount of a glucagon signaling pathway antagonist in combination with sodium phenylbutyrate or sodium benzoate, wherein the amount and/or dosage of sodium phenyl butyrate or sodium benzoate is reduced relative to the amount and/or dosage of sodium phenyl butyrate or sodium benzoate administered to a subject in the absence of a glucagon signaling pathway antagonist;

wherein plasma ammonia levels in the subject are decreased by at least about 9% to about 64% for at least about 7 days after the administration relative to an untreated subject, and wherein the hyperammonemia is associated with a defect in one or more urea cycle enzymes selected from the group consisting of carbamyl phosphate synthetase (CPS1), N-acetylglutamate synthetase (NAGS), ornithine transcarbamylase (OTC), argininosuccinic acid synthetase (ASS), argininosuccinate lyase (ASL), and arginase (AR1), or associated with glutamine synthetase deficiency.

13. The method of claim 12, wherein the glucagon signaling pathway antagonist is administered concomitantly with sodium phenylbutyrate and/or sodium benzoate.

14. The method of claim 12, wherein the glucagon signaling pathway antagonist is an isolated human monoclonal antibody or antigen-binding fragment thereof that specifically binds glucagon receptor, wherein the isolated human monoclonal antibody or antigen-binding fragment thereof comprises a heavy chain complementarity determining region (HCDR) 1, HCDR2, and HCDR3 within a heavy chain variable region (HCVR) amino acid sequence as set forth in SEQ ID NO: 86; and a light chain complementarity determining region (LCDR) 1, LCDR2, and LCDR3 within a light chain variable region (LCVR) amino acid sequence as set forth in SEQ ID NO: 88.

15. A method for lowering blood ammonia levels in a subject having hyperammonemia, the method comprising administering, to the subject, a therapeutically effective amount of a composition comprising a glucagon signaling pathway antagonist, such that plasma ammonia levels in the subject are decreased by at least about 9% to about 64% for at least about 7 days after the administration relative to an untreated subject;

wherein the hyperammonemia is associated with a defect in one or more urea cycle enzymes selected from the group consisting of carbamyl phosphate synthetase (CPS1), N-acetylglutamate synthetase (NAGS), ornithine transcarbamylase (OTC), argininosuccinic acid synthetase (ASS), argininosuccinate lyase (ASL), and arginase (AR1), or associated with glutamine synthetase deficiency.

16. The method of claim 15, wherein the glucagon signaling pathway antagonist is an isolated human monoclonal antibody or antigen-binding fragment thereof that specifically binds glucagon receptor, wherein the antibody or antigen-binding fragment thereof comprises a heavy chain complementarity determining region (HCDR) 1, HCDR2, and HCDR3 within a heavy chain variable region (HCVR) amino acid sequence as set forth in SEQ ID NO: 86; and a light chain complementarity determining region (LCDR) 1, LCDR2, and LCDR3 within a light chain variable region (LCVR) amino acid sequence as set forth in SEQ ID NO: 88.

17. A method for reducing excessive weight loss and/or lowering blood glucose in a subject with a urea cycle disorder comprising administering, to the subject, a therapeutically effective amount of a composition comprising an isolated human monoclonal antibody or antigen-binding fragment thereof that specifically binds glucagon receptor, wherein the antibody or antigen-binding fragment thereof comprises a heavy chain complementarity determining region (HCDR) 1, HCDR2, and HCDR3 within a heavy chain variable region (HCVR) amino acid sequence as set forth in SEQ ID NO: 86; and a light chain complementarity determining region (LCDR) 1, LCDR2, and LCDR3 within a light chain variable region (LCVR) amino acid sequence as set forth in SEQ ID NO: 88, wherein plasma ammonia levels in the subject are decreased by at least about 9% to about 64% for at least about 7 days after administration relative to an untreated subject.

18. The method of claim 17 wherein the subject is on a high protein diet.

* * * * *

SEQUENCE LISTING

```
<160> NUMBER OF SEQ ID NOS: 308

<210> SEQ ID NO 1
<211> LENGTH: 375
<212> TYPE: DNA
<213> ORGANISM: Artificial Sequence
<220> FEATURE:
<223> OTHER INFORMATION: Synthetic

<400> SEQUENCE: 1
caggtccagt tggtacagtc tggggctgac gtgaagaagc ctggggcctc agtgaaggtc      60
tcctgcaagg tttccggaca tatcctcact gatttatcca tgcactgggt gcgacagcct     120
cctgaaaaag gacttgagtg gatggcaggt tttgatcctg aagaaggtaa aataatctac     180
gcacagaagt tccagggcag agtcaccatg accgaggaca catctacaga cacagcctac     240
atggagctga gcagcctgag atctggggac acggccgttt attactgtgc aacaagcgat     300
attttgactg gtattatag agactactac ggtttggacg tctgggccca agggaccacg     360
ctcaccgtct cctca                                                     375

<210> SEQ ID NO 2
<211> LENGTH: 125
<212> TYPE: PRT
<213> ORGANISM: Artificial Sequence
<220> FEATURE:
<223> OTHER INFORMATION: Synthetic

<400> SEQUENCE: 2
```

```
Gln Val Gln Leu Val Gln Ser Gly Ala Asp Val Lys Pro Gly Ala
1               5                   10                  15

Ser Val Lys Val Ser Cys Lys Val Ser Gly His Ile Leu Thr Asp Leu
            20                  25                  30

Ser Met His Trp Val Arg Gln Pro Pro Gly Lys Gly Leu Glu Trp Met
        35                  40                  45

Ala Gly Phe Asp Pro Glu Glu Gly Lys Ile Ile Tyr Ala Gln Lys Phe
    50                  55                  60

Gln Gly Arg Val Thr Met Thr Glu Asp Thr Ser Asp Thr Ala Tyr
65                  70                  75                  80

Met Glu Leu Ser Ser Leu Arg Ser Gly Asp Thr Ala Val Tyr Tyr Cys
                85                  90                  95

Ala Thr Ser Asp Ile Leu Thr Gly Tyr Tyr Arg Asp Tyr Tyr Gly Leu
            100                 105                 110

Asp Val Trp Gly Gln Gly Thr Thr Leu Thr Val Ser Ser
        115                 120                 125

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ggacatatcc tcactgattt atcc                                          24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly His Ile Leu Thr Asp Leu Ser
1               5

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
tttgatcctg aagaaggtaa aata                                          24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Phe Asp Pro Glu Glu Gly Lys Ile
1               5

<210> SEQ ID NO 7
<211> LENGTH: 54
<212> TYPE: DNA
```

<213> ORGANISM: Artificial Sequence
<220> FEATURE:
<223> OTHER INFORMATION: Synthetic

<400> SEQUENCE: 7
gcaacaagcg atattttgac tgggtattat agagactact acggtttgga cgtc     54

<210> SEQ ID NO 8
<211> LENGTH: 18
<212> TYPE: PRT
<213> ORGANISM: Artificial Sequence
<220> FEATURE:
<223> OTHER INFORMATION: Synthetic

<400> SEQUENCE: 8

Ala Thr Ser Asp Ile Leu Thr Gly Tyr Tyr Arg Asp Tyr Tyr Gly Leu
1               5                   10                  15

Asp Val

<210> SEQ ID NO 9
<211> LENGTH: 336
<212> TYPE: DNA
<213> ORGANISM: Artificial Sequence
<220> FEATURE:
<223> OTHER INFORMATION: Synthetic

<400> SEQUENCE: 9
gatattgtga tgactcagtc tccactcttc ctgcccgtca cccctggaga gccggcctcc     60
atctcctgca ggtctagtca gagcctcctg catagtaaag atacaacta tttggattgg    120 tacctgcaga agccagggca gtctccacaa ctcctgatct atttgggttc taatcgggcc    180 tccgggggtcc ctgacaggtt cagtggcagt ggatcaggca cagattttac actgaaaatc    240
agcagagtgg aggctgaaga tgttggggtt tattactgca tgcaaactct acaaactcct    300
cggacgttcg gccaagggac caaggtggaa atcaaa                              336

<210> SEQ ID NO 10
<211> LENGTH: 112
<212> TYPE: PRT
<213> ORGANISM: Artificial Sequence
<220> FEATURE:
<223> OTHER INFORMATION: Synthetic

<400> SEQUENCE: 10

Asp Ile Val Met Thr Gln Ser Pro Leu Phe Leu Pro Val Thr Pro Gly
1               5                   10                  15

Glu Pro Ala Ser Ile Ser Cys Arg Ser Ser Gln Ser Leu Leu His Ser
            20                  25                  30

Lys Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Arg Thr Phe Gly Gln Gly Thr Lys Val Glu Ile Lys
            100                 105                 110

<210> SEQ ID NO 11
<211> LENGTH: 33

```
<212> TYPE: DNA
<213> ORGANISM: Artificial Sequence
<220> FEATURE:
<223> OTHER INFORMATION: Synthetic

<400> SEQUENCE: 11
cagagcctcc tgcatagtaa aggatacaac tat                                      33

<210> SEQ ID NO 12
<211> LENGTH: 11
<212> TYPE: PRT
<213> ORGANISM: Artificial Sequence
<220> FEATURE:
<223> OTHER INFORMATION: Synthetic

<400> SEQUENCE: 12

Gln Ser Leu Leu His Ser Lys Gly Tyr Asn Tyr
1               5                   10

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 ttgggttct                                                                  9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Leu Gly Ser
1

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
atgcaaactc tacaaactcc tcggacg                                             27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Met Gln Thr Leu Gln Thr Pro Arg Thr
1               5

<210> SEQ ID NO 17
<211> LENGTH: 375
<212> TYPE: DNA
<213> ORGANISM: Artificial Sequence
<220> FEATURE:
<223> OTHER INFORMATION: Synthetic
```

-continued

<400> SEQUENCE: 17

```
caggtccagt tggtacagtc tggggctgac gtgaagaagc tggggcctc agtgaaggtc    60
tcctgcaagg tttccggaca tatcctcact gatttatcca tgcactgggt gcgacaggct   120
cctggaaaag gcttgagtg gatgggaggt tttgatcctg aagaaggtga ataatctac    180
gcacagaagt tccagggcag agtcaccatg accgaggaca catctacaga cacagcctac   240
atggagctga gcagcctgag atctggggac acggccgttt attactgtgc aacaagcgat   300
attttgactg gttattatag agactactac ggtttggacg tctggggcca agggaccacg   360
ctcaccgtct cctca                                                   375
```

<210> SEQ ID NO 18
<211> LENGTH: 125
<212> TYPE: PRT
<213> ORGANISM: Artificial Sequence
<220> FEATURE:
<223> OTHER INFORMATION: Synthetic

<400> SEQUENCE: 18

```
Gln Val Gln Leu Val Gln Ser Gly Ala Asp Val Lys Lys Pro Gly Ala
1               5                   10                  15

Ser Val Lys Val Ser Cys Lys Val Ser Gly His Ile Leu Thr Asp Leu
            20                  25                  30

Ser Met His Trp Val Arg Gln Ala Pro Gly Lys Gly Leu Glu Trp Met
        35                  40                  45

Gly Gly Phe Asp Pro Glu Glu Gly Glu Ile Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Gly Asp Thr Ala Val Tyr Tyr Cys
                85                  90                  95

Ala Thr Ser Asp Ile Leu Thr Gly Tyr Tyr Arg Asp Tyr Tyr Gly Leu
            100                 105                 110

Asp Val Trp Gly Gln Gly Thr Thr Leu Thr Val Ser Ser
        115                 120                 125
```

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19

```
ggacatatcc tcactgattt atcc                                          24
```

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

```
Gly His Ile Leu Thr Asp Leu Ser
1               5
```

<210> SEQ ID NO 21
<211> LENGTH: 24

<212> TYPE: DNA
<213> ORGANISM: Artificial Sequence
<220> FEATURE:
<223> OTHER INFORMATION: Synthetic

<400> SEQUENCE: 21
tttgatcctg aagaaggtga aata                                    24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Phe Asp Pro Glu Glu Gly Glu Ile
1               5

<210> SEQ ID NO 23
<211> LENGTH: 54
<212> TYPE: DNA
<213> ORGANISM: Artificial Sequence
<220> FEATURE:
<223> OTHER INFORMATION: Synthetic

<400> SEQUENCE: 23
gcaacaagcg atattttgac tggttattat agagactact acggtttgga cgtc     54

<210> SEQ ID NO 24
<211> LENGTH: 18
<212> TYPE: PRT
<213> ORGANISM: Artificial Sequence
<220> FEATURE:
<223> OTHER INFORMATION: Synthetic

<400> SEQUENCE: 24

Ala Thr Ser Asp Ile Leu Thr Gly Tyr Tyr Arg Asp Tyr Tyr Gly Leu
1               5                   10                  15

Asp Val

<210> SEQ ID NO 25
<211> LENGTH: 336
<212> TYPE: DNA
<213> ORGANISM: Artificial Sequence
<220> FEATURE:
<223> OTHER INFORMATION: Synthetic

<400> SEQUENCE: 25
gatattgtga tgactcagtc tccactcttc ctgcccgtca cccctggaga gccggcctcc     60
atctcctgca ggtctagtca gagcctcctg catagtaaag gatacaacta tttggattgg    120
tacctgcaga agccagggca gtctccacaa ctcctgatct atttgggttc taatcgggcc    180
tccggggtcc ctgacaggtt cagtggcagt ggatcaggca cagattttac actgaaaatc    240
agcagagtgg aggctgaaga tgttggggtt tattactgca tgcaaactct acaaactcct    300
cggacgttcg gccaagggac caaggtggaa atcaaa                              336

<210> SEQ ID NO 26
<211> LENGTH: 112
<212> TYPE: PRT
<213> ORGANISM: Artificial Sequence
<220> FEATURE:
<223> OTHER INFORMATION: Synthetic -continued

<400> SEQUENCE: 26

Asp Ile Val Met Thr Gln Ser Pro Leu Phe Leu Pro Val Thr Pro Gly
1               5                   10                  15

Glu Pro Ala Ser Ile Ser Cys Arg Ser Gln Ser Leu Leu His Ser
            20                  25                  30

Lys Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Arg Thr Phe Gly Gln Gly Thr Lys Val Glu Ile Lys
            100                 105                 110

<210> SEQ ID NO 27
<211> LENGTH: 33
<212> TYPE: DNA
<213> ORGANISM: Artificial Sequence
<220> FEATURE:
<223> OTHER INFORMATION: Synthetic

<400> SEQUENCE: 27
cagagcctcc tgcatagtaa aggatacaac tat                           33

<210> SEQ ID NO 28
<211> LENGTH: 11
<212> TYPE: PRT
<213> ORGANISM: Artificial Sequence
<220> FEATURE:
<223> OTHER INFORMATION: Synthetic

<400> SEQUENCE: 28

Gln Ser Leu Leu His Ser Lys Gly Tyr Asn Tyr
1               5                   10

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29 ttgggttct                                                      9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Leu Gly Ser
1

<210> SEQ ID NO 31
<211> LENGTH: 27
<212> TYPE: DNA
<213> ORGANISM: Artificial Sequence
<220> FEATURE:

<223> OTHER INFORMATION: Synthetic

<400> SEQUENCE: 31
atgcaaactc tacaaactcc tcggacg                                                27

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Met Gln Thr Leu Gln Thr Pro Arg Thr
1               5

<210> SEQ ID NO 33
<211> LENGTH: 372
<212> TYPE: DNA
<213> ORGANISM: Artificial Sequence
<220> FEATURE:
<223> OTHER INFORMATION: Synthetic

<400> SEQUENCE: 33
gaggagcaac tggtggagtc tgggggagac ttggtacagc ctggagggtc cctaagactc      60
tcctgtgcag cctctggatt cactctcagt agttatgaaa tgaactgggt ccgccaggct     120
ccagggaagg ggctggagtg ggtttcatac attagtagag gtggtagtct gatacactac     180
acagactctg tgaagggccg attcaccatc tccagagaca acgccaagaa ttcactgtat     240
ctgcaaatga acagcctgag agccgaggac acggctgttt attactgtgt gagagaccca     300
gcagctcgtt atcattatta ttatcacggt atggacgtct ggggccaagg gaccacggtc     360
accgtctcct ca                                                        372

<210> SEQ ID NO 34
<211> LENGTH: 124
<212> TYPE: PRT
<213> ORGANISM: Artificial Sequence
<220> FEATURE:
<223> OTHER INFORMATION: Synthetic

<400> SEQUENCE: 34

Glu Glu Gln Leu Val Glu Ser Gly Gly Asp Leu Val Gln Pro Gly Gly
1               5                   10                  15

Ser Leu Arg Leu Ser Cys Ala Ala Ser Gly Phe Thr Leu Ser Ser Tyr
            20                  25                  30

Glu Met Asn Trp Val Arg Gln Ala Pro Gly Lys Gly Leu Glu Trp Val
        35                  40                  45

Ser Tyr Ile Ser Arg Gly Gly Ser Leu Ile His Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Asp Pro Ala Ala Arg Tyr His Tyr Tyr Tyr His Gly Met Asp
            100                 105                 110

Val Trp Gly Gln Gly Thr Thr Val Thr Val Ser Ser
        115                 120

<210> SEQ ID NO 35

```
<211> LENGTH: 24
<212> TYPE: DNA
<213> ORGANISM: Artificial Sequence
<220> FEATURE:
<223> OTHER INFORMATION: Synthetic

<400> SEQUENCE: 35
ggattcactc tcagtagtta tgaa                                              24

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Gly Phe Thr Leu Ser Ser Tyr Glu
1               5

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
attagtagag gtggtagtct gata                                              24

<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38

Ile Ser Arg Gly Gly Ser Leu Ile
1               5

<210> SEQ ID NO 39
<211> LENGTH: 51
<212> TYPE: DNA
<213> ORGANISM: Artificial Sequence
<220> FEATURE:
<223> OTHER INFORMATION: Synthetic

<400> SEQUENCE: 39
gtgagagacc cagcagctcg ttatcattat tattatcacg gtatggacgt c                51

<210> SEQ ID NO 40
<211> LENGTH: 17
<212> TYPE: PRT
<213> ORGANISM: Artificial Sequence
<220> FEATURE:
<223> OTHER INFORMATION: Synthetic

<400> SEQUENCE: 40

Val Arg Asp Pro Ala Ala Arg Tyr His Tyr Tyr Tyr His Gly Met Asp
1               5                   10                  15

Val

<210> SEQ ID NO 41
<211> LENGTH: 336
<212> TYPE: DNA
```

<213> ORGANISM: Artificial Sequence
<220> FEATURE:
<223> OTHER INFORMATION: Synthetic

<400> SEQUENCE: 41

```
gatattgtga tgactcagtc tccactctcc ctgcccgtca ccctggaga gccggcctcc      60 atctcctgca ggtctagtca gagcctcctg cacaataatg gatataacta tttggattgg    120
tatctgcaga agccagggca gtctccacag ctcctgatct atttgggttc tagtcgggcc    180
tccggggtcc ctgacaggtt cagtggcagt ggatcaggca cagatttat actgaaaatc     240 agcagagtgg aggctgaaga tgttggggtt tattactgca tgcaagctct acaaactccg    300
tggacgttcg gccgagggac caaggtggaa atcaaa                              336
```

<210> SEQ ID NO 42
<211> LENGTH: 112
<212> TYPE: PRT
<213> ORGANISM: Artificial Sequence
<220> FEATURE:
<223> OTHER INFORMATION: Synthetic

<400> SEQUENCE: 42

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Asn
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Ser Arg Ala Ser Gly Val Pro
    50                  55                  60

Asp Arg Phe Ser Gly Ser Gly Ser Gly Thr Asp Phe Ile Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Arg Gly Thr Lys Val Glu Ile Lys
            100                 105                 110
```

<210> SEQ ID NO 43
<211> LENGTH: 33
<212> TYPE: DNA
<213> ORGANISM: Artificial Sequence
<220> FEATURE:
<223> OTHER INFORMATION: Synthetic

<400> SEQUENCE: 43

```
cagagcctcc tgcacaataa tggatataac tat                                  33
```

<210> SEQ ID NO 44
<211> LENGTH: 11
<212> TYPE: PRT
<213> ORGANISM: Artificial Sequence
<220> FEATURE:
<223> OTHER INFORMATION: Synthetic

<400> SEQUENCE: 44

```
Gln Ser Leu Leu His Asn Asn Gly Tyr Asn Tyr
1               5                   10
```

<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45 ttgggttct                                                                 9

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Leu Gly Ser
1

<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
atgcaagctc tacaaactcc gtggacg                                            27

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Met Gln Ala Leu Gln Thr Pro Trp Thr
1               5

<210> SEQ ID NO 49
<211> LENGTH: 384
<212> TYPE: DNA
<213> ORGANISM: Artificial Sequence
<220> FEATURE:
<223> OTHER INFORMATION: Synthetic

<400> SEQUENCE: 49
gaggtgcagc tggtggagtc tgggggaggc gtggtccagc ctggggaggtc cctgagactc        60
tcctgtgcag cctctggatt caccttcagt agttatgaca tgcactgggt ccgccaggct       120
ccaggcaagg ggctggagtg ggtggcagtt atatcatctg atggacgtga taaatactat       180
gtagactccg tgaagggccg attcaccatc tccagagaca actccaagaa cacgctttat       240
ctgcaaatga acagcctgag agctgaggac acggctgttt attactgtgc gaaagagatg       300
gtgtattacg atattttgac tggttatcat aactactacg gtatggacgt ctggggccaa       360
gggaccacgg tcaccgtctc ctca                                              384

<210> SEQ ID NO 50
<211> LENGTH: 128
<212> TYPE: PRT
<213> ORGANISM: Artificial Sequence
<220> FEATURE:
<223> OTHER INFORMATION: Synthetic

<400> SEQUENCE: 50

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Ile Ser Ser Asp Gly Arg Asp Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Met Val Tyr Tyr Asp Ile Leu Thr Gly Tyr His Asn Tyr
            100                 105                 110

Tyr Gly Met Asp Val Trp Gly Gln Gly Thr Thr Val Thr Val Ser Ser
        115                 120                 125

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51
ggattcacct tcagtagtta tgac                                        24

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

Gly Phe Thr Phe Ser Ser Tyr Asp
1               5

<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53
atatcatctg atggacgtga taaa                                        24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Ile Ser Ser Asp Gly Arg Asp Lys
1               5

<210> SEQ ID NO 55
<211> LENGTH: 63
<212> TYPE: DNA
<213> ORGANISM: Artificial Sequence

```
<220> FEATURE:
<223> OTHER INFORMATION: Synthetic

<400> SEQUENCE: 55
gcgaaagaga tggtgtatta cgatattttg actggttatc ataactacta cggtatggac    60
gtc                                                                  63

<210> SEQ ID NO 56
<211> LENGTH: 21
<212> TYPE: PRT
<213> ORGANISM: Artificial Sequence
<220> FEATURE:
<223> OTHER INFORMATION: Synthetic

<400> SEQUENCE: 56

Ala Lys Glu Met Val Tyr Tyr Asp Ile Leu Thr Gly Tyr His Asn Tyr
1               5                   10                  15

Tyr Gly Met Asp Val
            20

<210> SEQ ID NO 57
<211> LENGTH: 324
<212> TYPE: DNA
<213> ORGANISM: Artificial Sequence
<220> FEATURE:
<223> OTHER INFORMATION: Synthetic

<400> SEQUENCE: 57
gacatcgtga tgacccagtc tccatcctca ctgtctgcat ctgtaggaga cagagtcacc    60
atcacttgtc gggcgagtca gggcattaac aattatttag cctggtttca gcagaaacca   120
gggaaagccc ctaagtccct gatccatact gcatccagtt tgcaaagtgg ggtcccatca   180
aagttcagcg gcagtggatc tgggacagat ttcactctca ccatcagcag cctgcagcct   240
gaagattttg caacttatta ctgccaacag tataatactt accctctcac tttcggcgga   300
gggaccaaag tggagatcaa acga                                          324

<210> SEQ ID NO 58
<211> LENGTH: 108
<212> TYPE: PRT
<213> ORGANISM: Artificial Sequence
<220> FEATURE:
<223> OTHER INFORMATION: Synthetic

<400> SEQUENCE: 58

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Ala Trp Phe Gln Gln Lys Pro Gly Lys Ala Pro Lys Ser Leu Ile
        35                  40                  45

His Thr Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Thr Tyr Pro Leu
                85                  90                  95

Thr Phe Gly Gly Gly Thr Lys Val Glu Ile Lys Arg
            100                 105
```

```
<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59
cagggcatta acaattat                                                18

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

Gln Gly Ile Asn Asn Tyr
1               5

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 actgcatcc                                                           9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Thr Ala Ser
1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
caacagtata atacttaccc tctcact                                       27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Gln Gln Tyr Asn Thr Tyr Pro Leu Thr
1               5

<210> SEQ ID NO 65
<211> LENGTH: 381
<212> TYPE: DNA
<213> ORGANISM: Artificial Sequence
```

```
<220> FEATURE:
<223> OTHER INFORMATION: Synthetic

<400> SEQUENCE: 65
caggtgcagc tggtggagtc tgggggaggc gtggtccagc ctgggaggtc cctgagactc      60
tcctgtgcag cctctggatt caccttcagt agttatgaca tgcactgggt ccgccaggct     120
ccaggcaagg ggctggagtg ggtggcagtt atatcatctg atggacgtga taaatactat     180
gtagactccg tgaagggccg attcaccatc tccagagaca actccaagaa cacgctttat     240
ctgcaaatga acagcctgag agctgaggac acggctgttt attactgtgc aaagagatg      300
gtgtattacg atattttgac tggttatcat aactactacg gtatggacgt ctggggccaa     360
gggaccacgg tcaccgtctc c                                                381

<210> SEQ ID NO 66
<211> LENGTH: 127
<212> TYPE: PRT
<213> ORGANISM: Artificial Sequence
<220> FEATURE:
<223> OTHER INFORMATION: Synthetic

<400> SEQUENCE: 66

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Ile Ser Ser Asp Gly Arg Asp Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Met Val Tyr Tyr Asp Ile Leu Thr Gly Tyr His Asn Tyr
            100                 105                 110

Tyr Gly Met Asp Val Trp Gly Gln Gly Thr Thr Val Thr Val Ser
        115                 120                 125

<210> SEQ ID NO 67
<211> LENGTH: 321
<212> TYPE: DNA
<213> ORGANISM: Artificial Sequence
<220> FEATURE:
<223> OTHER INFORMATION: Synthetic

<400> SEQUENCE: 67
gacatccaga tgacccagtc tccatcctca ctgtctgcat ctgtaggaga cagagtcacc      60
atcacttgtc gggcgagtca gggcattaac aattatttag cctggtttca gcagaaacca     120
gggaaagccc ctaagtccct gatccatact gcatccagtt tgcaaagtgg ggtcccatca     180
aagttcagcg gcagtggatc tgggacagat ttcactctca ccatcagcag cctgcagcct     240
gaagattttg caacttatta ctgccaacag tataatactt accctctcac tttcggcgga     300
gggaccaagg tggagatcaa a                                                321

<210> SEQ ID NO 68
<211> LENGTH: 107
<212> TYPE: PRT
```

<213> ORGANISM: Artificial Sequence
<220> FEATURE:
<223> OTHER INFORMATION: Synthetic

<400> SEQUENCE: 68

Asp Ile Gln Met Thr Gln Ser Pro Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Ala Trp Phe Gln Gln Lys Pro Gly Lys Ala Pro Lys Ser Leu Ile
        35                  40                  45

His Thr Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Thr Tyr Pro Leu
                85                  90                  95

Thr Phe Gly Gly Gly Thr Lys Val Glu Ile Lys
            100                 105

<210> SEQ ID NO 69
<211> LENGTH: 384
<212> TYPE: DNA
<213> ORGANISM: Artificial Sequence
<220> FEATURE:
<223> OTHER INFORMATION: Synthetic

<400> SEQUENCE: 69
caggtgcagc tggtgcagtc tgggggaggc ttggtccagc ctggggggtc cctgagactc     60
tcctgtgcag cctccggatt cacctttagt aactatttga tgaactgggt ccgccaggct    120
ccagggaagg ggctggagtg gctggccaac atacaggaag atggaattga aaaatactat    180
gtggactctg tgaagggccg attcaccatc tccagagaca acgccaagaa ctcactgtat    240
ctgcaaatga acagcctgag agccgaggac acggctgtgt attactgtgc gagagagccc    300
tcccattacg atattttgac tggttatgac tactattacg gtatggacgt ctggggccaa    360
gggaccacgg tcaccgtctc ctca                                          384

<210> SEQ ID NO 70
<211> LENGTH: 128
<212> TYPE: PRT
<213> ORGANISM: Artificial Sequence
<220> FEATURE:
<223> OTHER INFORMATION: Synthetic

<400> SEQUENCE: 70

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Leu Met Asn Trp Val Arg Gln Ala Pro Gly Lys Gly Leu Glu Trp Leu
        35                  40                  45

Ala Asn Ile Gln Glu Asp Gly Ile Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Ser His Tyr Asp Ile Leu Thr Gly Tyr Asp Tyr Tyr
            100                 105                 110

Tyr Gly Met Asp Val Trp Gly Gln Gly Thr Thr Val Thr Val Ser Ser
        115                 120                 125

<210> SEQ ID NO 71
<211> LENGTH: 24
<212> TYPE: DNA
<213> ORGANISM: Artificial Sequence
<220> FEATURE:
<223> OTHER INFORMATION: Synthetic

<400> SEQUENCE: 71
ggattcacct ttagtaacta tttg                                         24

<210> SEQ ID NO 72
<211> LENGTH: 8
<212> TYPE: PRT
<213> ORGANISM: Artificial Sequence
<220> FEATURE:
<223> OTHER INFORMATION: Synthetic

<400> SEQUENCE: 72

Gly Phe Thr Phe Ser Asn Tyr Leu
1               5

<210> SEQ ID NO 73
<211> LENGTH: 24
<212> TYPE: DNA
<213> ORGANISM: Artificial Sequence
<220> FEATURE:
<223> OTHER INFORMATION: Synthetic

<400> SEQUENCE: 73
atacaggaag atggaattga gaaa                                         24

<210> SEQ ID NO 74
<211> LENGTH: 8
<212> TYPE: PRT
<213> ORGANISM: Artificial Sequence
<220> FEATURE:
<223> OTHER INFORMATION: Synthetic

<400> SEQUENCE: 74

Ile Gln Glu Asp Gly Ile Glu Lys
1               5

<210> SEQ ID NO 75
<211> LENGTH: 63
<212> TYPE: DNA
<213> ORGANISM: Artificial Sequence
<220> FEATURE:
<223> OTHER INFORMATION: Synthetic

<400> SEQUENCE: 75
gcgagagagc cctcccatta cgatattttg actggttatg actactatta cggtatggac   60
gtc                                                                63

<210> SEQ ID NO 76
<211> LENGTH: 21
<212> TYPE: PRT
<213> ORGANISM: Artificial Sequence
<220> FEATURE:
<223> OTHER INFORMATION: Synthetic

<400> SEQUENCE: 76

Ala Arg Glu Pro Ser His Tyr Asp Ile Leu Thr Gly Tyr Asp Tyr Tyr
1               5                   10                  15

Tyr Gly Met Asp Val
            20

<210> SEQ ID NO 77
<211> LENGTH: 324
<212> TYPE: DNA
<213> ORGANISM: Artificial Sequence
<220> FEATURE:
<223> OTHER INFORMATION: Synthetic

<400> SEQUENCE: 77
gacatccagt tgacccagtc tccatcctcc ctgtctgcat ctgtaggaga cagagtcacc      60
atcacttgcc gggcaagtca gggcattaga aatgatttag gctggtatca gcagaaacca    120
gggaaagccc ctaagcgcct gatctatgct gcatccagtt tgcaaagtgg ggtcccatca    180
aggttcagcg gcagtggatc tgggacagaa ttcattctca cagtcagcag cctgcagcct    240
gaagactttg caacttatta ctgtctacag tataatagta acccattcac tttcggccct    300
gggaccaagg tggagatcaa acga                                          324

<210> SEQ ID NO 78
<211> LENGTH: 108
<212> TYPE: PRT
<213> ORGANISM: Artificial Sequence
<220> FEATURE:
<223> OTHER INFORMATION: Synthetic

<400> SEQUENCE: 78

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Ile Leu Thr Val Ser Ser Leu Gln Pro
65                  70                  75                  80

Glu Asp Phe Ala Thr Tyr Tyr Cys Leu Gln Tyr Asn Ser Asn Pro Phe
                85                  90                  95

Thr Phe Gly Pro Gly Thr Lys Val Glu Ile Lys Arg
            100                 105

<210> SEQ ID NO 79
<211> LENGTH: 18
<212> TYPE: DNA
<213> ORGANISM: Artificial Sequence
<220> FEATURE:
<223> OTHER INFORMATION: Synthetic

<400> SEQUENCE: 79
cagggcatta gaaatgat                                                  18

<210> SEQ ID NO 80
<211> LENGTH: 6
<212> TYPE: PRT
<213> ORGANISM: Artificial Sequence
<220> FEATURE:
<223> OTHER INFORMATION: Synthetic
<210> SEQ ID NO 81
<211> LENGTH: 9
<212> TYPE: DNA
<213> ORGANISM: Artificial Sequence
<220> FEATURE:
<223> OTHER INFORMATION: Synthetic

<400> SEQUENCE: 81 gctgcatcc                                                                  9

<210> SEQ ID NO 82
<211> LENGTH: 3
<212> TYPE: PRT
<213> ORGANISM: Artificial Sequence
<220> FEATURE:
<223> OTHER INFORMATION: Synthetic

<400> SEQUENCE: 82

Ala Ala Ser
1

<210> SEQ ID NO 83
<211> LENGTH: 27
<212> TYPE: DNA
<213> ORGANISM: Artificial Sequence
<220> FEATURE:
<223> OTHER INFORMATION: Synthetic

<400> SEQUENCE: 83
ctacagtata atagtaaccc attcact                                             27

<210> SEQ ID NO 84
<211> LENGTH: 9
<212> TYPE: PRT
<213> ORGANISM: Artificial Sequence
<220> FEATURE:
<223> OTHER INFORMATION: Synthetic

<400> SEQUENCE: 84

Leu Gln Tyr Asn Ser Asn Pro Phe Thr
1               5

<210> SEQ ID NO 85
<211> LENGTH: 381
<212> TYPE: DNA
<213> ORGANISM: Artificial Sequence
<220> FEATURE:
<223> OTHER INFORMATION: Synthetic

<400> SEQUENCE: 85
gaggtgcagc tggtggagtc tgggggaggc ttggtccagc ctgggggtc cctgagactc          60 tcctgtgcag cctccggatt caccttagt aactatttga tgaactgggt ccgccaggct         120
ccagggaagg ggctggagtg gctggccaac atacaggaag atggaattga aaatactat         180 gtggactctg tgaagggccg attcaccatc tccagagaca cgccaagaa ctcactgtat         240 ctgcaaatga acagcctgag agccgaggac acggctgtgt attactgtgc gagagagccc        300
tcccattacg atatttgac tggttatgac tactattacg gtatggacgt ctggggccaa         360
gggaccacgg tcaccgtctc c                                                 381

<400> SEQUENCE: 80

Gln Gly Ile Arg Asn Asp
1               5

<210> SEQ ID NO 86
<211> LENGTH: 127
<212> TYPE: PRT
<213> ORGANISM: Artificial Sequence
<220> FEATURE:
<223> OTHER INFORMATION: Synthetic

<400> SEQUENCE: 86

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Leu Met Asn Trp Val Arg Gln Ala Pro Gly Lys Gly Leu Glu Trp Leu
        35                  40                  45

Ala Asn Ile Gln Glu Asp Gly Ile Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Ser His Tyr Asp Ile Leu Thr Gly Tyr Asp Tyr Tyr
            100                 105                 110

Tyr Gly Met Asp Val Trp Gly Gln Gly Thr Thr Val Thr Val Ser
        115                 120                 125
```

<210> SEQ ID NO 87
<211> LENGTH: 321
<212> TYPE: DNA
<213> ORGANISM: Artificial Sequence
<220> FEATURE:
<223> OTHER INFORMATION: Synthetic

<400> SEQUENCE: 87

```
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcattctca cagtcagcag cctgcagcct   240
gaagactttg caacttatta ctgtctacag tataatagta acccattcac tttcggccct   300
gggaccaaag tggatatcaa a                                              321
```

<210> SEQ ID NO 88
<211> LENGTH: 107
<212> TYPE: PRT
<213> ORGANISM: Artificial Sequence
<220> FEATURE:
<223> OTHER INFORMATION: Synthetic

<400> SEQUENCE: 88

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60
```

```
Ser Gly Ser Gly Thr Glu Phe Ile Leu Thr Val Ser Ser Leu Gln Pro
 65                  70                  75                  80

Glu Asp Phe Ala Thr Tyr Tyr Cys Leu Gln Tyr Asn Ser Asn Pro Phe
                 85                  90                  95

Thr Phe Gly Pro Gly Thr Lys Val Asp Ile Lys
            100                 105
```

<210> SEQ ID NO 89
<211> LENGTH: 381
<212> TYPE: DNA
<213> ORGANISM: Artificial Sequence
<220> FEATURE:
<223> OTHER INFORMATION: Synthetic

<400> SEQUENCE: 89

```
gaggtgcagc tggtgcagtc tgggggagcc ttggtacagc ctgggggtc cctgagactc      60
tcctgtacag cctctggttt caccttcagt aactacgaca tgcactgggt ccgccaaact    120
acaggaaaag gtctggagtg gatctcagct attgatactg ctggtgacac atactatcca    180
ggctccgtga agggccgatt caccgtctcc agagaaaatg ccaagaactc ctttatctt    240
caaatgaaca gcctgagagc cggggacacg gctgtgtatt actgtgcaag ggaggggaag    300
tattacgata ttttgactgg tgactaccac tactacggta tggacgtctg gggccaaggg    360
accacggtca ccgtctcctc a                                              381
```

<210> SEQ ID NO 90
<211> LENGTH: 127
<212> TYPE: PRT
<213> ORGANISM: Artificial Sequence
<220> FEATURE:
<223> OTHER INFORMATION: Synthetic

<400> SEQUENCE: 90

```
Glu Val Gln Leu Val Gln Ser Gly Gly Ala Leu Val Gln Pro Gly Gly
  1               5                  10                  15

Ser Leu Arg Leu Ser Cys Thr Ala Ser Gly Phe Thr Phe Ser Asn Tyr
                 20                  25                  30

Asp Met His Trp Val Arg Gln Thr Thr Gly Lys Gly Leu Glu Trp Ile
             35                  40                  45

Ser Ala Ile Asp Thr Ala Gly Asp Thr Tyr Tyr Pro Gly Ser Val Lys
         50                  55                  60

Gly Arg Phe Thr Val Ser Arg Glu Asn Ala Lys Asn Ser Phe Tyr Leu
 65                  70                  75                  80

Gln Met Asn Ser Leu Arg Ala Gly Asp Thr Ala Val Tyr Tyr Cys Ala
                 85                  90                  95

Arg Glu Gly Lys Tyr Tyr Asp Ile Leu Thr Gly Asp Tyr His Tyr Tyr
                100                 105                 110

Gly Met Asp Val Trp Gly Gln Gly Thr Thr Val Thr Val Ser Ser
            115                 120                 125
```

<210> SEQ ID NO 91
<211> LENGTH: 24
<212> TYPE: DNA
<213> ORGANISM: Artificial Sequence
<220> FEATURE:
<223> OTHER INFORMATION: Synthetic

<400> SEQUENCE: 91

```
ggtttcacct tcagtaacta cgac                                            24
```

<210> SEQ ID NO 92
<211> LENGTH: 8
<212> TYPE: PRT
<213> ORGANISM: Artificial Sequence
<220> FEATURE:
<223> OTHER INFORMATION: Synthetic

<400> SEQUENCE: 92

Gly Phe Thr Phe Ser Asn Tyr Asp
1               5

<210> SEQ ID NO 93
<211> LENGTH: 21
<212> TYPE: DNA
<213> ORGANISM: Artificial Sequence
<220> FEATURE:
<223> OTHER INFORMATION: Synthetic

<400> SEQUENCE: 93
attgatactg ctggtgacac a                                              21

<210> SEQ ID NO 94
<211> LENGTH: 7
<212> TYPE: PRT
<213> ORGANISM: Artificial Sequence
<220> FEATURE:
<223> OTHER INFORMATION: Synthetic

<400> SEQUENCE: 94

Ile Asp Thr Ala Gly Asp Thr
1               5

<210> SEQ ID NO 95
<211> LENGTH: 63
<212> TYPE: DNA
<213> ORGANISM: Artificial Sequence
<220> FEATURE:
<223> OTHER INFORMATION: Synthetic

<400> SEQUENCE: 95
gcaagggagg ggaagtatta cgatattttg actggtgact accactacta cggtatggac    60
gtc                                                                  63

<210> SEQ ID NO 96
<211> LENGTH: 21
<212> TYPE: PRT
<213> ORGANISM: Artificial Sequence
<220> FEATURE:
<223> OTHER INFORMATION: Synthetic

<400> SEQUENCE: 96

Ala Arg Glu Gly Lys Tyr Tyr Asp Ile Leu Thr Gly Asp Tyr His Tyr
1               5                  10                  15

Tyr Gly Met Asp Val
            20

<210> SEQ ID NO 97
<211> LENGTH: 324
<212> TYPE: DNA
<213> ORGANISM: Artificial Sequence
<220> FEATURE:
<223> OTHER INFORMATION: Synthetic

<400> SEQUENCE: 97
gccatccgga tgacccagtc tccatcctcc ctgtctgcat ctgtaggaga cagagtcacc    60

```
atcacttgtc gggcaagtca gggcattaga aatgatttag gctggtatca gcagaaacca    120
gggaaagccc ctaagcgact gatctatgct acatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt acccgctcac tttcggcgga    300
gggaccaagg tggaaatcaa acga                                           324
```

<210> SEQ ID NO 98
<211> LENGTH: 108
<212> TYPE: PRT
<213> ORGANISM: Artificial Sequence
<220> FEATURE:
<223> OTHER INFORMATION: Synthetic

<400> SEQUENCE: 98

```
Ala Ile Arg Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Thr Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Leu
                 85                  90                  95

Thr Phe Gly Gly Gly Thr Lys Val Glu Ile Lys Arg
            100                 105
```

<210> SEQ ID NO 99
<211> LENGTH: 18
<212> TYPE: DNA
<213> ORGANISM: Artificial Sequence
<220> FEATURE:
<223> OTHER INFORMATION: Synthetic

<400> SEQUENCE: 99

```
cagggcatta gaaatgat                                                   18
```

<210> SEQ ID NO 100
<211> LENGTH: 6
<212> TYPE: PRT
<213> ORGANISM: Artificial Sequence
<220> FEATURE:
<223> OTHER INFORMATION: Synthetic

<400> SEQUENCE: 100

```
Gln Gly Ile Arg Asn Asp
 1               5
```

<210> SEQ ID NO 101
<211> LENGTH: 9
<212> TYPE: DNA
<213> ORGANISM: Artificial Sequence
<220> FEATURE:
<223> OTHER INFORMATION: Synthetic

<400> SEQUENCE: 101

```
gctacatcc                                                              9
```

<210> SEQ ID NO 102
<211> LENGTH: 3
<212> TYPE: PRT
<213> ORGANISM: Artificial Sequence
<220> FEATURE:
<223> OTHER INFORMATION: Synthetic

<400> SEQUENCE: 102

Ala Thr Ser
1

<210> SEQ ID NO 103
<211> LENGTH: 27
<212> TYPE: DNA
<213> ORGANISM: Artificial Sequence
<220> FEATURE:
<223> OTHER INFORMATION: Synthetic

<400> SEQUENCE: 103
ctacagcata atagttaccc gctcact                                          27

<210> SEQ ID NO 104
<211> LENGTH: 9
<212> TYPE: PRT
<213> ORGANISM: Artificial Sequence
<220> FEATURE:
<223> OTHER INFORMATION: Synthetic

<400> SEQUENCE: 104

Leu Gln His Asn Ser Tyr Pro Leu Thr
1               5

<210> SEQ ID NO 105
<211> LENGTH: 378
<212> TYPE: DNA
<213> ORGANISM: Artificial Sequence
<220> FEATURE:
<223> OTHER INFORMATION: Synthetic

<400> SEQUENCE: 105
gaggtgcagc tggtggagtc tgggggagcc ttggtacagc ctgggggtc cctgagactc       60 tcctgtacag cctctggttt caccttcagt aactacgaca tgcactgggt ccgccaaact     120
acaggaaaag gtctggagtg gatctcagct attgatactg ctggtgacac atactatcca    180
ggctccgtga agggccgatt caccgtctcc agagaaaatg ccaagaactc cttttatctt    240
caaatgaaca gcctgagagc cggggacacg gctgtgtatt actgtgcaag ggagggggaag  300 tattacgata ttttgactgg tgactaccac tactacggta tggacgtctg gggccaaggg   360
accacggtca ccgtctcc                                                 378

<210> SEQ ID NO 106
<211> LENGTH: 126
<212> TYPE: PRT
<213> ORGANISM: Artificial Sequence
<220> FEATURE:
<223> OTHER INFORMATION: Synthetic

<400> SEQUENCE: 106

Glu Val Gln Leu Val Glu Ser Gly Gly Ala Leu Val Gln Pro Gly Gly
1               5                   10                  15

Ser Leu Arg Leu Ser Cys Thr Ala Ser Gly Phe Thr Phe Ser Asn Tyr
            20                  25                  30

Asp Met His Trp Val Arg Gln Thr Thr Gly Lys Gly Leu Glu Trp Ile

```
                    35                  40                  45

Ser Ala Ile Asp Thr Ala Gly Asp Thr Tyr Tyr Pro Gly Ser Val Lys
 50                  55                  60

Gly Arg Phe Thr Val Ser Arg Glu Asn Ala Lys Asn Ser Phe Tyr Leu
 65                  70                  75                  80

Gln Met Asn Ser Leu Arg Ala Gly Asp Thr Ala Val Tyr Tyr Cys Ala
                 85                  90                  95

Arg Glu Gly Lys Tyr Tyr Asp Ile Leu Thr Gly Asp Tyr His Tyr Tyr
             100                 105                 110

Gly Met Asp Val Trp Gly Gln Gly Thr Thr Val Thr Val Ser
         115                 120                 125

<210> SEQ ID NO 107
<211> LENGTH: 321
<212> TYPE: DNA
<213> ORGANISM: Artificial Sequence
<220> FEATURE:
<223> OTHER INFORMATION: Synthetic

<400> SEQUENCE: 107
gacatccaga tgacccagtc tccatcctcc ctgtctgcat ctgtaggaga cagagtcacc        60
atcacttgtc gggcaagtca gggcattaga aatgatttag gctggtatca gcagaaacca       120
gggaaagccc ctaagcgact gatctatgct acatccagtt tgcaaagtgg ggtcccatca       180
aggttcagcg gcagtggatc tgggacagaa ttcactctca caatcagcag cctgcagcct       240
gaagattttg caacttatta ctgtctacag cataatagtt acccgctcac tttcggcgga       300
gggaccaagc tggagatcaa a                                                 321

<210> SEQ ID NO 108
<211> LENGTH: 107
<212> TYPE: PRT
<213> ORGANISM: Artificial Sequence
<220> FEATURE:
<223> OTHER INFORMATION: Synthetic

<400> SEQUENCE: 108

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
                 20                  25                  30

Leu Gly Trp Tyr Gln Gln Lys Pro Gly Lys Ala Pro Lys Arg Leu Ile
             35                  40                  45

Tyr Ala Thr Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Leu
                 85                  90                  95

Thr Phe Gly Gly Gly Thr Lys Leu Glu Ile Lys
             100                 105

<210> SEQ ID NO 109
<211> LENGTH: 372
<212> TYPE: DNA
<213> ORGANISM: Artificial Sequence
<220> FEATURE:
<223> OTHER INFORMATION: Synthetic

<400> SEQUENCE: 109
```

```
caggtgcagc tggtgcagtc tgggggaggc gtggtccagc ctgggaggtc cctgagactc    60
tcctgtgcag cgtctggggtt cacctttagt aactttggca tgcactgggt ccgccaggct   120
ccaggcaagg ggctggagtg ggtggcagtt atatggtttg atgaaattga taaatactat   180
gcagactccg tgaagggccg attcaccatc tccagagaca attccaagaa cacgctgtat   240
ccgcaaatga acagcctgag agccgaagac acggctgtgt attactgtgc gcgagaagat   300
tacgatattt tgactggtta ctattacgct atggacgtct ggggccaagg gaccacggtc   360
accgtctcct ca                                                       372
```

<210> SEQ ID NO 110
<211> LENGTH: 124
<212> TYPE: PRT
<213> ORGANISM: Artificial Sequence
<220> FEATURE:
<223> OTHER INFORMATION: Synthetic

<400> SEQUENCE: 110

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Asn Phe
            20                  25                  30

Gly Met His Trp Val Arg Gln Ala Pro Gly Lys Gly Leu Glu Trp Val
        35                  40                  45

Ala Val Ile Trp Phe Asp Glu Ile Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Pro Gln Met Asn Ser Leu Arg Ala Glu Asp Thr Ala Val Tyr Tyr Cys
                85                  90                  95

Ala Arg Glu Asp Tyr Asp Ile Leu Thr Gly Tyr Tyr Tyr Ala Met Asp
            100                 105                 110

Val Trp Gly Gln Gly Thr Thr Val Thr Val Ser Ser
        115                 120
```

<210> SEQ ID NO 111
<211> LENGTH: 24
<212> TYPE: DNA
<213> ORGANISM: Artificial Sequence
<220> FEATURE:
<223> OTHER INFORMATION: Synthetic

<400> SEQUENCE: 111

```
gggttcacct ttagtaactt tggc                                           24
```

<210> SEQ ID NO 112
<211> LENGTH: 8
<212> TYPE: PRT
<213> ORGANISM: Artificial Sequence
<220> FEATURE:
<223> OTHER INFORMATION: Synthetic

<400> SEQUENCE: 112

```
Gly Phe Thr Phe Ser Asn Phe Gly
1               5
```

<210> SEQ ID NO 113
<211> LENGTH: 24
<212> TYPE: DNA
<213> ORGANISM: Artificial Sequence

```
<220> FEATURE:
<223> OTHER INFORMATION: Synthetic

<400> SEQUENCE: 113
atatggtttg atgaaattga taaa                                              24

<210> SEQ ID NO 114
<211> LENGTH: 8
<212> TYPE: PRT
<213> ORGANISM: Artificial Sequence
<220> FEATURE:
<223> OTHER INFORMATION: Synthetic

<400> SEQUENCE: 114

Ile Trp Phe Asp Glu Ile Asp Lys
1               5

<210> SEQ ID NO 115
<211> LENGTH: 51
<212> TYPE: DNA
<213> ORGANISM: Artificial Sequence
<220> FEATURE:
<223> OTHER INFORMATION: Synthetic

<400> SEQUENCE: 115
gcgcgagaag attacgatat tttgactggt tactattacg ctatggacgt c                51

<210> SEQ ID NO 116
<211> LENGTH: 17
<212> TYPE: PRT
<213> ORGANISM: Artificial Sequence
<220> FEATURE:
<223> OTHER INFORMATION: Synthetic

<400> SEQUENCE: 116

Ala Arg Glu Asp Tyr Asp Ile Leu Thr Gly Tyr Tyr Tyr Ala Met Asp
1               5                   10                  15

Val

<210> SEQ ID NO 117
<211> LENGTH: 321
<212> TYPE: DNA
<213> ORGANISM: Artificial Sequence
<220> FEATURE:
<223> OTHER INFORMATION: Synthetic

<400> SEQUENCE: 117
gacatccaga tgacccagtc tccatcctcc ctgtctgcat ctgtaggaga cagagtcacc        60
atcacttgcc gggcaagtca gggcattaga aatgatttag ctggtatca gcagaaacca       120 gggaaagccc ctaagcgcct aatctatgct gcatcccgtt tgcaaagtgg ggtcccatcg       180
aggttcagcg gcagtggatc tgggacagaa ttcactctca caatcagcag cctgcagcct       240
gaagattttg aacttatta ctgtctacag cataatagtc accccacctt cggccaaggg       300
accaaggtgg agatcaaacg a                                                 321

<210> SEQ ID NO 118
<211> LENGTH: 107
<212> TYPE: PRT
<213> ORGANISM: Artificial Sequence
<220> FEATURE:
<223> OTHER INFORMATION: Synthetic

<400> SEQUENCE: 118
```

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Arg Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Gly Thr Tyr Tyr Cys Leu Gln His Asn Ser His Pro Thr
                85                  90                  95

Phe Gly Gln Gly Thr Lys Val Glu Ile Lys Arg
            100                 105
```

<210> SEQ ID NO 119
<211> LENGTH: 18
<212> TYPE: DNA
<213> ORGANISM: Artificial Sequence
<220> FEATURE:
<223> OTHER INFORMATION: Synthetic

<400> SEQUENCE: 119
cagggcatta gaaatgat                                                    18

<210> SEQ ID NO 120
<211> LENGTH: 6
<212> TYPE: PRT
<213> ORGANISM: Artificial Sequence
<220> FEATURE:
<223> OTHER INFORMATION: Synthetic

<400> SEQUENCE: 120

```
Gln Gly Ile Arg Asn Asp
 1               5
```

<210> SEQ ID NO 121
<211> LENGTH: 9
<212> TYPE: DNA
<213> ORGANISM: Artificial Sequence
<220> FEATURE:
<223> OTHER INFORMATION: Synthetic

<400> SEQUENCE: 121 gctgcatcc                                                               9

<210> SEQ ID NO 122
<211> LENGTH: 3
<212> TYPE: PRT
<213> ORGANISM: Artificial Sequence
<220> FEATURE:
<223> OTHER INFORMATION: Synthetic

<400> SEQUENCE: 122

```
Ala Ala Ser
 1
```

<210> SEQ ID NO 123
<211> LENGTH: 24
<212> TYPE: DNA
<213> ORGANISM: Artificial Sequence
<220> FEATURE:
<223> OTHER INFORMATION: Synthetic

<400> SEQUENCE: 123
ctacagcata atagtcaccc cacc                                                              24

<210> SEQ ID NO 124
<211> LENGTH: 8
<212> TYPE: PRT
<213> ORGANISM: Artificial Sequence
<220> FEATURE:
<223> OTHER INFORMATION: Synthetic

<400> SEQUENCE: 124

Leu Gln His Asn Ser His Pro Thr
1               5

<210> SEQ ID NO 125
<211> LENGTH: 369
<212> TYPE: DNA
<213> ORGANISM: Artificial Sequence
<220> FEATURE:
<223> OTHER INFORMATION: Synthetic

<400> SEQUENCE: 125
caggtgcagc tggtggagtc tgggggaggc gtggtccagc ctggggaggtc cctgagactc      60 tcctgtgcag cgtctgggtt cacctttagt aactttggca tgcactgggt ccgccaggct     120
ccaggcaagg ggctggagtg ggtggcagtt atatggtttg atgaaattga taaatactat     180
gcagactccg tgaagggccg attcaccatc tccagagaca attccaagaa cacgctgtat     240
ccgcaaatga acagcctgag agccgaagac acggctgtgt attactgtgc gcgagaagat     300
tacgatattt tgactggtta ctattacgct atggacgtct ggggccaagg gaccacggtc     360
accgtctcc                                                              369

<210> SEQ ID NO 126
<211> LENGTH: 123
<212> TYPE: PRT
<213> ORGANISM: Artificial Sequence
<220> FEATURE:
<223> OTHER INFORMATION: Synthetic

<400> SEQUENCE: 126

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Phe
            20                  25                  30

Gly Met His Trp Val Arg Gln Ala Pro Gly Lys Gly Leu Glu Trp Val
        35                  40                  45

Ala Val Ile Trp Phe Asp Glu Ile Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Pro Gln Met Asn Ser Leu Arg Ala Glu Asp Thr Ala Val Tyr Tyr Cys
                85                  90                  95

Ala Arg Glu Asp Tyr Asp Ile Leu Thr Gly Tyr Tyr Tyr Ala Met Asp
            100                 105                 110

Val Trp Gly Gln Gly Thr Thr Val Thr Val Ser
        115                 120

<210> SEQ ID NO 127
<211> LENGTH: 318
<212> TYPE: DNA

<213> ORGANISM: Artificial Sequence
<220> FEATURE:
<223> OTHER INFORMATION: Synthetic

<400> SEQUENCE: 127

```
gacatccaga tgacccagtc tccatcctcc ctgtctgcat ctgtaggaga cagagtcacc        60
atcacttgcc gggcaagtca gggcattaga aatgatttag gctggtatca gcagaaacca       120
gggaaagccc ctaagcgcct aatctatgct gcatcccgtt tgcaaagtgg ggtcccatcg       180
aggttcagcg gcagtggatc tgggacagaa ttcactctca caatcagcag cctgcagcct       240
gaagattttg gaacttatta ctgtctacag cataatagtc accccacctt cggccaaggg       300
accaaggtgg agatcaaa                                                     318
```

<210> SEQ ID NO 128
<211> LENGTH: 106
<212> TYPE: PRT
<213> ORGANISM: Artificial Sequence
<220> FEATURE:
<223> OTHER INFORMATION: Synthetic

<400> SEQUENCE: 128

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Lys Asn Asp
            20                  25                  30
Leu Gly Trp Tyr Gln Gln Lys Pro Gly Lys Ala Pro Lys Arg Leu Ile
        35                  40                  45
Tyr Ala Ala Ser Arg Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Gly Thr Tyr Tyr Cys Leu Gln His Asn Ser His Pro Thr
                85                  90                  95
Phe Gly Gln Gly Thr Lys Val Glu Ile Lys
            100                 105
```

<210> SEQ ID NO 129
<211> LENGTH: 381
<212> TYPE: DNA
<213> ORGANISM: Artificial Sequence
<220> FEATURE:
<223> OTHER INFORMATION: Synthetic

<400> SEQUENCE: 129

```
gaggtgcagc tggtggagtc ggggggaggc atggtacagc ctggggggtc cctgagactc        60
tcctgtgcag cctctggatt cacctccagt aactacgaca tgcactgggt ccgccaagct       120
acaggaaaag gtctggagtg gtctcaagt attgatactg ctggggacac ttactatcca       180
gactccgtga agggccgctt tatcatctcc agagaaaatg ccaaaaactc cctgtatctt       240
caaatgaata gcctgagagc cggggacacg gctgtgtatt actgtacaag ggagccccga       300
aattacgaaa tttttgactgg tcactaccac taccacggta tggacatctg gggccaaggg       360
accacggtca ccgtctcctc a                                                 381
```

<210> SEQ ID NO 130
<211> LENGTH: 127
<212> TYPE: PRT
<213> ORGANISM: Artificial Sequence
<220> FEATURE:

<223> OTHER INFORMATION: Synthetic

<400> SEQUENCE: 130

Glu Val Gln Leu Val Glu Ser Gly Gly Gly Met Val Gln Pro Gly Gly
1               5                   10                  15

Ser Leu Arg Leu Ser Cys Ala Ala Ser Gly Phe Thr Ser Ser Asn Tyr
            20                  25                  30

Asp Met His Trp Val Arg Gln Ala Thr Gly Lys Gly Leu Glu Trp Val
        35                  40                  45

Ser Ser Ile Asp Thr Ala Gly Asp Thr Tyr Tyr Pro Asp Ser Val Lys
    50                  55                  60

Gly Arg Phe Ile Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Thr
                85                  90                  95

Arg Glu Pro Arg Asn Tyr Glu Ile Leu Thr Gly His Tyr His Tyr His
            100                 105                 110

Gly Met Asp Ile Trp Gly Gln Gly Thr Thr Val Thr Val Ser Ser
        115                 120                 125

<210> SEQ ID NO 131
<211> LENGTH: 24
<212> TYPE: DNA
<213> ORGANISM: Artificial Sequence
<220> FEATURE:
<223> OTHER INFORMATION: Synthetic

<400> SEQUENCE: 131
ggattcacct ccagtaacta cgac                                          24

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

Gly Phe Thr Ser Ser Asn Tyr Asp
1               5

<210> SEQ ID NO 133
<211> LENGTH: 21
<212> TYPE: DNA
<213> ORGANISM: Artificial Sequence
<220> FEATURE:
<223> OTHER INFORMATION: Synthetic

<400> SEQUENCE: 133
attgatactg ctggggacac t                                             21

<210> SEQ ID NO 134
<211> LENGTH: 7
<212> TYPE: PRT
<213> ORGANISM: Artificial Sequence
<220> FEATURE:
<223> OTHER INFORMATION: Synthetic

<400> SEQUENCE: 134

Ile Asp Thr Ala Gly Asp Thr
1               5

<210> SEQ ID NO 135
<211> LENGTH: 63
<212> TYPE: DNA
<213> ORGANISM: Artificial Sequence
<220> FEATURE:
<223> OTHER INFORMATION: Synthetic

<400> SEQUENCE: 135

```
acaagggagc cccgaaatta cgaaattttg actggtcact accactacca cggtatggac    60
atc                                                                  63
```

<210> SEQ ID NO 136
<211> LENGTH: 21
<212> TYPE: PRT
<213> ORGANISM: Artificial Sequence
<220> FEATURE:
<223> OTHER INFORMATION: Synthetic

<400> SEQUENCE: 136

Thr Arg Glu Pro Arg Asn Tyr Glu Ile Leu Thr Gly His Tyr His Tyr
1               5                   10                  15

His Gly Met Asp Ile
            20

<210> SEQ ID NO 137
<211> LENGTH: 324
<212> TYPE: DNA
<213> ORGANISM: Artificial Sequence
<220> FEATURE:
<223> OTHER INFORMATION: Synthetic

<400> SEQUENCE: 137

```
gacatccaga tgacccagtc gccatcctcc ctgtctgcat ctgtaggaga cagagtcacc    60
atcacttgcc gggcaagtca ggccattaga aatgatttag ctggtatca gcagaaacca   120 gggaaagccc ctaaactcct gatctatact gcattcagtt tacagagtgg gtcccatca   180 aggttcagcg gcagtaaatc tggcacagac ttcactctca ccatcagcag cctgcagcct   240
gaagattttg cgacttatta ctgtctgcag gattacacta atcctcggac gttcggccaa   300
gggaccaagg tggagatcaa acga                                          324
```

<210> SEQ ID NO 138
<211> LENGTH: 108
<212> TYPE: PRT
<213> ORGANISM: Artificial Sequence
<220> FEATURE:
<223> OTHER INFORMATION: Synthetic

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Arg Asn Asp
            20                  25                  30

Leu Gly Trp Tyr Gln Gln Lys Pro Gly Lys Ala Pro Lys Leu Leu Ile
        35                  40                  45

Tyr Thr Ala Phe Ser Leu Gln Ser Gly Val Pro Ser Arg Phe Ser Gly
    50                  55                  60

Ser Lys Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Thr Asn Pro Arg
                85                  90                  95

Thr Phe Gly Gln Gly Thr Lys Val Glu Ile Lys Arg
            100                 105

<210> SEQ ID NO 139
<211> LENGTH: 18
<212> TYPE: DNA
<213> ORGANISM: Artificial Sequence
<220> FEATURE:
<223> OTHER INFORMATION: Synthetic

<400> SEQUENCE: 139
caggccatta gaaatgat                                                   18

<210> SEQ ID NO 140
<211> LENGTH: 6
<212> TYPE: PRT
<213> ORGANISM: Artificial Sequence
<220> FEATURE:
<223> OTHER INFORMATION: Synthetic

<400> SEQUENCE: 140

Gln Ala Ile Arg Asn Asp
1               5

<210> SEQ ID NO 141
<211> LENGTH: 9
<212> TYPE: DNA
<213> ORGANISM: Artificial Sequence
<220> FEATURE:
<223> OTHER INFORMATION: Synthetic

<400> SEQUENCE: 141 actgcattc                                                              9

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

Thr Ala Phe
1

<210> SEQ ID NO 143
<211> LENGTH: 27
<212> TYPE: DNA
<213> ORGANISM: Artificial Sequence
<220> FEATURE:
<223> OTHER INFORMATION: Synthetic

<400> SEQUENCE: 143
ctgcaggatt acactaatcc tcggacg                                         27

<210> SEQ ID NO 144
<211> LENGTH: 9
<212> TYPE: PRT
<213> ORGANISM: Artificial Sequence
<220> FEATURE:
<223> OTHER INFORMATION: Synthetic

<400> SEQUENCE: 144

Leu Gln Asp Tyr Thr Asn Pro Arg Thr
1               5

```
<210> SEQ ID NO 145
<211> LENGTH: 378
<212> TYPE: DNA
<213> ORGANISM: Artificial Sequence
<220> FEATURE:
<223> OTHER INFORMATION: Synthetic

<400> SEQUENCE: 145
gaggtgcagc tggtggagtc ggggggaggc atggtacagc ctggggggtc cctgagactc        60
tcctgtgcag cctctggatt cacctccagt aactacgaca tgcactgggt ccgccaagct       120
acaggaaaag gtctggagtg gtctcaagt attgatactg ctggggacac ttactatcca       180
gactccgtga agggccgctt tatcatctcc agagaaaatg ccaaaaactc cctgtatctt       240
caaatgaata gcctgagagc cggggacacg gctgtgtatt actgtacaag ggagccccga       300
aattacgaaa ttttgactgg tcactaccac taccacggta tggacatctg gggccaaggg       360
accacggtca ccgtctcc                                                    378

<210> SEQ ID NO 146
<211> LENGTH: 126
<212> TYPE: PRT
<213> ORGANISM: Artificial Sequence
<220> FEATURE:
<223> OTHER INFORMATION: Synthetic

<400> SEQUENCE: 146

Glu Val Gln Leu Val Glu Ser Gly Gly Gly Met Val Gln Pro Gly Gly
1               5                   10                  15

Ser Leu Arg Leu Ser Cys Ala Ala Ser Gly Phe Thr Ser Ser Asn Tyr
            20                  25                  30

Asp Met His Trp Val Arg Gln Ala Thr Gly Lys Gly Leu Glu Trp Val
        35                  40                  45

Ser Ser Ile Asp Thr Ala Gly Asp Thr Tyr Tyr Pro Asp Ser Val Lys
    50                  55                  60

Gly Arg Phe Ile Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Thr
                85                  90                  95

Arg Glu Pro Arg Asn Tyr Glu Ile Leu Thr Gly His Tyr His Tyr His
            100                 105                 110

Gly Met Asp Ile Trp Gly Gln Gly Thr Thr Val Thr Val Ser
        115                 120                 125

<210> SEQ ID NO 147
<211> LENGTH: 321
<212> TYPE: DNA
<213> ORGANISM: Artificial Sequence
<220> FEATURE:
<223> OTHER INFORMATION: Synthetic

<400> SEQUENCE: 147
gccatccaga tgacccagtc gccatcctcc ctgtctgcat ctgtaggaga cagagtcacc        60
atcacttgcc gggcaagtca ggccattaga aatgatttag ctggtatca gcagaaacca       120 gggaaagccc ctaaactcct gatctatact gcattcagtt tacagagtgg ggtcccatca       180
aggttcagcg gcagtaaatc tggcacagac ttcactctca ccatcagcag cctgcagcct       240
gaagattttg cgacttatta ctgtctgcag gattacacta tcctcggac gttcggccaa       300 gggaccaagg tggaaatcaa a                                                321
```

<210> SEQ ID NO 148
<211> LENGTH: 107
<212> TYPE: PRT
<213> ORGANISM: Artificial Sequence
<220> FEATURE:
<223> OTHER INFORMATION: Synthetic

<400> SEQUENCE: 148

```
Ala Ile Gln Met Thr Gln Ser Pro Ser Leu Ser Ala Ser Val Gly
1               5                   10                  15

Asp Arg Val Thr Ile Thr Cys Arg Ala Ser Gln Ala Ile Arg Asn Asp
            20                  25                  30

Leu Gly Trp Tyr Gln Gln Lys Pro Gly Lys Ala Pro Lys Leu Leu Ile
        35                  40                  45

Tyr Thr Ala Phe Ser Leu Gln Ser Gly Val Pro Ser Arg Phe Ser Gly
50                  55                  60

Ser Lys Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Pro Arg
                85                  90                  95

Thr Phe Gly Gln Gly Thr Lys Val Glu Ile Lys
            100                 105
```

<210> SEQ ID NO 149
<211> LENGTH: 357
<212> TYPE: DNA
<213> ORGANISM: Artificial Sequence
<220> FEATURE:
<223> OTHER INFORMATION: synthetic

<400> SEQUENCE: 149

```
caggtgcagc tggtggagtc tgggggaggc gtggtccagc ctggaggtc cctgagactc      60
tcctgtgcag cctctggatt cgccttcagt aactatggca tgcactgggt ccgccaggct    120
ccaggcaagg ggctggaatg ggtgacattt atatcatatg atggaagtaa taatactat     180
gcagactccg tgaagggccg attcaccatc tccagagaca attccaagaa cacgctgtat    240
ctgcaagtga acagcctgag agctgaggac acggctgtgt attactgtgc gaaagaagca    300
gtattagctg ccctctttga ctactggggc cagggaaccc tggtcaccgt ctcctca       357
```

<210> SEQ ID NO 150
<211> LENGTH: 119
<212> TYPE: PRT
<213> ORGANISM: Artificial Sequence
<220> FEATURE:
<223> OTHER INFORMATION: synthetic

<400> SEQUENCE: 150

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Asn Tyr
            20                  25                  30

Gly Met His Trp Val Arg Gln Ala Pro Gly Lys Gly Leu Glu Trp Val
        35                  40                  45

Thr Phe Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Val Asn Ser Leu Arg Ala Glu Asp Thr Ala Val Tyr Tyr Cys
```

```
                85                  90                  95
Ala Lys Glu Ala Val Leu Ala Ala Leu Phe Asp Tyr Trp Gly Gln Gly
            100                 105                 110

Thr Leu Val Thr Val Ser Ser
        115

<210> SEQ ID NO 151
<211> LENGTH: 24
<212> TYPE: DNA
<213> ORGANISM: Artificial Sequence
<220> FEATURE:
<223> OTHER INFORMATION: synthetic

<400> SEQUENCE: 151
ggattcgcct tcagtaacta tggc                                          24

<210> SEQ ID NO 152
<211> LENGTH: 8
<212> TYPE: PRT
<213> ORGANISM: Artificial Sequence
<220> FEATURE:
<223> OTHER INFORMATION: synthetic

<400> SEQUENCE: 152

Gly Phe Ala Phe Ser Asn Tyr Gly
1               5

<210> SEQ ID NO 153
<211> LENGTH: 24
<212> TYPE: DNA
<213> ORGANISM: Artificial Sequence
<220> FEATURE:
<223> OTHER INFORMATION: synthetic

<400> SEQUENCE: 153
atatcatatg atggaagtaa taaa                                          24

<210> SEQ ID NO 154
<211> LENGTH: 8
<212> TYPE: PRT
<213> ORGANISM: Artificial Sequence
<220> FEATURE:
<223> OTHER INFORMATION: synthetic

<400> SEQUENCE: 154

Ile Ser Tyr Asp Gly Ser Asn Lys
1               5

<210> SEQ ID NO 155
<211> LENGTH: 36
<212> TYPE: DNA
<213> ORGANISM: Artificial Sequence
<220> FEATURE:
<223> OTHER INFORMATION: synthetic

<400> SEQUENCE: 155
gcgaaagaag cagtattagc tgccctcttt gactac                             36

<210> SEQ ID NO 156
<211> LENGTH: 12
<212> TYPE: PRT
<213> ORGANISM: Artificial Sequence
<220> FEATURE:
<223> OTHER INFORMATION: synthetic

<400> SEQUENCE: 156
```

Ala Lys Glu Ala Val Leu Ala Ala Leu Phe Asp Tyr
1               5                   10

<210> SEQ ID NO 157
<211> LENGTH: 336
<212> TYPE: DNA
<213> ORGANISM: Artificial Sequence
<220> FEATURE:
<223> OTHER INFORMATION: synthetic

<400> SEQUENCE: 157
gacatcgtga tgacccagtc tccagactcc ctggctgtgt ctctgggcga gagggccacc    60
atcaactgca agtccagcca gagtgtttta tacagctcca acaatcagaa ctacttagct   120
tggtaccagc agaaaccagg acagcctcct aagctgctca tttactgggc atctacccgg   180
gaatccgggg tccctgaccg attcagtggc agcgggtctg ggacagattt cactctcacc   240
atcaacagcc tgcaggctga agatgtggca gtttattact gtcagcaata ttatagtact   300
cctacgttcg gccaagggac caaggtggaa atcaaa                             336

<210> SEQ ID NO 158
<211> LENGTH: 112
<212> TYPE: PRT
<213> ORGANISM: Artificial Sequence
<220> FEATURE:
<223> OTHER INFORMATION: synthetic

<400> SEQUENCE: 158

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Gln Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Val Tyr Tyr Cys Gln Gln
                85                  90                  95

Tyr Tyr Ser Thr Pro Thr Phe Gly Gln Gly Thr Lys Val Glu Ile Lys
            100                 105                 110

<210> SEQ ID NO 159
<211> LENGTH: 36
<212> TYPE: DNA
<213> ORGANISM: Artificial Sequence
<220> FEATURE:
<223> OTHER INFORMATION: synthetic

<400> SEQUENCE: 159
cagagtgttt tatacagctc caacaatcag aactac                              36

<210> SEQ ID NO 160
<211> LENGTH: 12
<212> TYPE: PRT
<213> ORGANISM: Artificial Sequence
<220> FEATURE:
<223> OTHER INFORMATION: synthetic

<400> SEQUENCE: 160

```
Gln Ser Val Leu Tyr Ser Ser Asn Asn Gln Asn Tyr
1               5                   10
```

<210> SEQ ID NO 161
<211> LENGTH: 9
<212> TYPE: DNA
<213> ORGANISM: Artificial Sequence
<220> FEATURE:
<223> OTHER INFORMATION: synthetic

<400> SEQUENCE: 161 tgggcatct                                                                 9

<210> SEQ ID NO 162
<211> LENGTH: 3
<212> TYPE: PRT
<213> ORGANISM: Artificial Sequence
<220> FEATURE:
<223> OTHER INFORMATION: synthetic

<400> SEQUENCE: 162

Trp Ala Ser
1

<210> SEQ ID NO 163
<211> LENGTH: 24
<212> TYPE: DNA
<213> ORGANISM: Artificial Sequence
<220> FEATURE:
<223> OTHER INFORMATION: synthetic

<400> SEQUENCE: 163
cagcaatatt atagtactcc tacg                                               24

<210> SEQ ID NO 164
<211> LENGTH: 8
<212> TYPE: PRT
<213> ORGANISM: Artificial Sequence
<220> FEATURE:
<223> OTHER INFORMATION: synthetic

<400> SEQUENCE: 164

Gln Gln Tyr Tyr Ser Thr Pro Thr
1               5

<210> SEQ ID NO 165
<211> LENGTH: 357
<212> TYPE: DNA
<213> ORGANISM: Artificial Sequence
<220> FEATURE:
<223> OTHER INFORMATION: synthetic

<400> SEQUENCE: 165
caggtgcagc tggtggagtc tgggggaggc gtggtccagc ctggggaggtc cctgagactc        60 tcctgtgcag cctctggatt cacgttcaat acctatggca tgcactgggt ccgccaggct       120
ccagtcaagg ggctggagtg ggtggcattt atatcaaatg ataagagtaa tacattctat       180
gcagactccg tgaagggccg attcaccatc tccagagaca attccaagaa cacgctgttt       240
ctggaaatga acagcctgac agctgaggac acggctgttt attactgtgc gaaagagtcc       300
attttagcag ccctctttga ctactggggc cagggaaccc tggtcactgt ctcctca          357

<210> SEQ ID NO 166
<211> LENGTH: 119
<212> TYPE: PRT

<213> ORGANISM: Artificial Sequence
<220> FEATURE:
<223> OTHER INFORMATION: synthetic

<400> SEQUENCE: 166

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Asn Thr Tyr
            20                  25                  30

Gly Met His Trp Val Arg Gln Ala Pro Val Lys Gly Leu Glu Trp Val
        35                  40                  45

Ala Phe Ile Ser Asn Asp Lys Ser Asn Thr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Glu Met Asn Ser Leu Thr Ala Glu Asp Thr Ala Val Tyr Tyr Cys
                85                  90                  95

Ala Lys Glu Ser Ile Leu Ala Ala Leu Phe Asp Tyr Trp Gly Gln Gly
            100                 105                 110

Thr Leu Val Thr Val Ser Ser
        115
```

<210> SEQ ID NO 167
<211> LENGTH: 24
<212> TYPE: DNA
<213> ORGANISM: Artificial Sequence
<220> FEATURE:
<223> OTHER INFORMATION: synthetic

<400> SEQUENCE: 167
ggattcacgt tcaataccta tggc    24

<210> SEQ ID NO 168
<211> LENGTH: 8
<212> TYPE: PRT
<213> ORGANISM: Artificial Sequence
<220> FEATURE:
<223> OTHER INFORMATION: synthetic

<400> SEQUENCE: 168

```
Gly Phe Thr Phe Asn Thr Tyr Gly
1               5
```

<210> SEQ ID NO 169
<211> LENGTH: 24
<212> TYPE: DNA
<213> ORGANISM: Artificial Sequence
<220> FEATURE:
<223> OTHER INFORMATION: synthetic

<400> SEQUENCE: 169
atatcaaatg ataagagtaa taca    24

<210> SEQ ID NO 170
<211> LENGTH: 8
<212> TYPE: PRT
<213> ORGANISM: Artificial Sequence
<220> FEATURE:
<223> OTHER INFORMATION: synthetic

<400> SEQUENCE: 170

```
Ile Ser Asn Asp Lys Ser Asn Thr
1               5
```

<210> SEQ ID NO 171
<211> LENGTH: 36
<212> TYPE: DNA
<213> ORGANISM: Artificial Sequence
<220> FEATURE:
<223> OTHER INFORMATION: synthetic

<400> SEQUENCE: 171
gcgaaagagt ccattttagc agccctcttt gactac                                36

<210> SEQ ID NO 172
<211> LENGTH: 12
<212> TYPE: PRT
<213> ORGANISM: Artificial Sequence
<220> FEATURE:
<223> OTHER INFORMATION: synthetic

<400> SEQUENCE: 172

Ala Lys Glu Ser Ile Leu Ala Ala Leu Phe Asp Tyr
1               5                   10

<210> SEQ ID NO 173
<211> LENGTH: 336
<212> TYPE: DNA
<213> ORGANISM: Artificial Sequence
<220> FEATURE:
<223> OTHER INFORMATION: synthetic

<400> SEQUENCE: 173
gacatcgtga tgacccagtc tccagactcc ctggctgtgt ctctgggcga gagggccacc        60
atcaactgca gtccagcca gagtgtttta tacagctcca acaataagaa ttacttagct       120
tggtaccaac agaaaccaag acagcctctt aaactactca tttactgggc atctattcgg      180
gaatccgggg tccctgaccg attcagtggc agcgggtctg ggacagattt cactctcacc      240
atcagcagcc tgcaggctga agatgtggca gtttattact gtcagcaatt ttatagtgtt      300
cccacttttg gccaggggac caagctggag atcaaa                                336

<210> SEQ ID NO 174
<211> LENGTH: 112
<212> TYPE: PRT
<213> ORGANISM: Artificial Sequence
<220> FEATURE:
<223> OTHER INFORMATION: synthetic

<400> SEQUENCE: 174

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Arg Gln
        35                  40                  45

Pro Leu Lys Leu Leu Ile Tyr Trp Ala Ser Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Tyr Ser Val Pro Thr Phe Gly Gln Gly Thr Lys Leu Glu Ile Lys
            100                 105                 110

<210> SEQ ID NO 175
<211> LENGTH: 36
<212> TYPE: DNA
<213> ORGANISM: Artificial Sequence
<220> FEATURE:
<223> OTHER INFORMATION: synthetic

<400> SEQUENCE: 175
cagagtgttt tatacagctc caacaataag aattac                              36

<210> SEQ ID NO 176
<211> LENGTH: 12
<212> TYPE: PRT
<213> ORGANISM: Artificial Sequence
<220> FEATURE:
<223> OTHER INFORMATION: synthetic

<400> SEQUENCE: 176

Gln Ser Val Leu Tyr Ser Ser Asn Asn Lys Asn Tyr
1               5                   10

<210> SEQ ID NO 177
<211> LENGTH: 9
<212> TYPE: DNA
<213> ORGANISM: Artificial Sequence
<220> FEATURE:
<223> OTHER INFORMATION: synthetic

<400> SEQUENCE: 177 tgggcatct                                                             9

<210> SEQ ID NO 178
<211> LENGTH: 3
<212> TYPE: PRT
<213> ORGANISM: Artificial Sequence
<220> FEATURE:
<223> OTHER INFORMATION: synthetic

<400> SEQUENCE: 178

Trp Ala Ser
1

<210> SEQ ID NO 179
<211> LENGTH: 24
<212> TYPE: DNA
<213> ORGANISM: Artificial Sequence
<220> FEATURE:
<223> OTHER INFORMATION: synthetic

<400> SEQUENCE: 179
cagcaatttt atagtgttcc cact                                            24

<210> SEQ ID NO 180
<211> LENGTH: 8
<212> TYPE: PRT
<213> ORGANISM: Artificial Sequence
<220> FEATURE:
<223> OTHER INFORMATION: synthetic

<400> SEQUENCE: 180

Gln Gln Phe Tyr Ser Val Pro Thr
1               5

<210> SEQ ID NO 181
<211> LENGTH: 357
<212> TYPE: DNA

<210> SEQ ID NO 181
<211> LENGTH: 357
<212> TYPE: DNA
<213> ORGANISM: Artificial Sequence
<220> FEATURE:
<223> OTHER INFORMATION: synthetic

<400> SEQUENCE: 181
caggtgcagc tggtggagtc tgggggaggc gtggtccagc ctggagggtc cctgagactc    60
tcctgtgcag cctctggatt cacgtttagt acctttggca tgcactgggt ccgccaggct   120
ccagtcaagg ggctggagtg gtggcttttt atatcaaatg ataagaataa taaattctat   180
gcagactccg tgaagggccg attcaccatc tccagagaca attccaggga cacgctatat   240
ctgcaaatga acagcctgac acctgaggac acggctgttt attactgtgc gaaagagtcc   300
attttagcag ccctctttga ctactggggc cagggaaccc tggtcaccgt ctcctca      357

<210> SEQ ID NO 182
<211> LENGTH: 119
<212> TYPE: PRT
<213> ORGANISM: Artificial Sequence
<220> FEATURE:
<223> OTHER INFORMATION: synthetic

<400> SEQUENCE: 182

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Phe
            20                  25                  30

Gly Met His Trp Val Arg Gln Ala Pro Val Lys Gly Leu Glu Trp Val
        35                  40                  45

Ala Phe Ile Ser Asn Asp Lys Asn Asn Lys Phe Tyr Ala Asp Ser Val
    50                  55                  60

Lys Gly Arg Phe Thr Ile Ser Arg Asp Asn Ser Arg Asp Thr Leu Tyr
65                  70                  75                  80

Leu Gln Met Asn Ser Leu Thr Pro Glu Asp Thr Ala Val Tyr Tyr Cys
                85                  90                  95

Ala Lys Glu Ser Ile Leu Ala Ala Leu Phe Asp Tyr Trp Gly Gln Gly
            100                 105                 110

Thr Leu Val Thr Val Ser Ser
        115

<210> SEQ ID NO 183
<211> LENGTH: 24
<212> TYPE: DNA
<213> ORGANISM: Artificial Sequence
<220> FEATURE:
<223> OTHER INFORMATION: synthetic

<400> SEQUENCE: 183
ggattcacgt ttagtaccttt tggc                                          24

<210> SEQ ID NO 184
<211> LENGTH: 8
<212> TYPE: PRT
<213> ORGANISM: Artificial Sequence
<220> FEATURE:
<223> OTHER INFORMATION: synthetic

<400> SEQUENCE: 184

Gly Phe Thr Phe Ser Thr Phe Gly
1               5

<210> SEQ ID NO 185

```
<211> LENGTH: 24
<212> TYPE: DNA
<213> ORGANISM: Artificial Sequence
<220> FEATURE:
<223> OTHER INFORMATION: synthetic

<400> SEQUENCE: 185
atatcaaatg ataagaataa taaa                                              24

<210> SEQ ID NO 186
<211> LENGTH: 8
<212> TYPE: PRT
<213> ORGANISM: Artificial Sequence
<220> FEATURE:
<223> OTHER INFORMATION: synthetic

<400> SEQUENCE: 186

Ile Ser Asn Asp Lys Asn Asn Lys
1               5

<210> SEQ ID NO 187
<211> LENGTH: 36
<212> TYPE: DNA
<213> ORGANISM: Artificial Sequence
<220> FEATURE:
<223> OTHER INFORMATION: synthetic

<400> SEQUENCE: 187
gcgaaagagt ccattttagc agccctcttt gactac                                 36

<210> SEQ ID NO 188
<211> LENGTH: 12
<212> TYPE: PRT
<213> ORGANISM: Artificial Sequence
<220> FEATURE:
<223> OTHER INFORMATION: synthetic

<400> SEQUENCE: 188

Ala Lys Glu Ser Ile Leu Ala Ala Leu Phe Asp Tyr
1               5                   10

<210> SEQ ID NO 189
<211> LENGTH: 336
<212> TYPE: DNA
<213> ORGANISM: Artificial Sequence
<220> FEATURE:
<223> OTHER INFORMATION: synthetic

<400> SEQUENCE: 189
gacatcgtga tgacccagtc tccagactcc ctggctgtgt ctctgggcga gagggccacc       60
atcaactgca gtccagcca gagtgtttta tacagctcca acaataaaaa ttacttagct       120
tggtaccagc agaaaccagg acagcctctt aaacttctca tttactgggc atctattcgg      180
gaatccgggg tccctgaccg attcagtggc agcgggtctg ggacagattt cactctcacc      240
atcagcagcc tgcaggctga agatgtggca gtttattact gtcagcaatt ttatactgtt      300
cccacttttg gcctggggac caagctggag atcaaa                                336

<210> SEQ ID NO 190
<211> LENGTH: 112
<212> TYPE: PRT
<213> ORGANISM: Artificial Sequence
<220> FEATURE:
<223> OTHER INFORMATION: synthetic

<400> SEQUENCE: 190
```

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Leu Lys Leu Leu Ile Tyr Trp Ala Ser Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Tyr Thr Val Pro Thr Phe Gly Leu Gly Thr Lys Leu Glu Ile Lys
            100                 105                 110

<210> SEQ ID NO 191
<211> LENGTH: 36
<212> TYPE: DNA
<213> ORGANISM: Artificial Sequence
<220> FEATURE:
<223> OTHER INFORMATION: synthetic

<400> SEQUENCE: 191
cagagtgttt tatacagctc caacaataaa aattac                              36

<210> SEQ ID NO 192
<211> LENGTH: 12
<212> TYPE: PRT
<213> ORGANISM: Artificial Sequence
<220> FEATURE:
<223> OTHER INFORMATION: synthetic

<400> SEQUENCE: 192

Gln Ser Val Leu Tyr Ser Ser Asn Asn Lys Asn Tyr
1               5                   10

<210> SEQ ID NO 193
<211> LENGTH: 9
<212> TYPE: DNA
<213> ORGANISM: Artificial Sequence
<220> FEATURE:
<223> OTHER INFORMATION: synthetic

<400> SEQUENCE: 193 tgggcatct                                                             9

<210> SEQ ID NO 194
<211> LENGTH: 3
<212> TYPE: PRT
<213> ORGANISM: Artificial Sequence
<220> FEATURE:
<223> OTHER INFORMATION: synthetic

<400> SEQUENCE: 194

Trp Ala Ser
1

<210> SEQ ID NO 195
<211> LENGTH: 24
<212> TYPE: DNA
<213> ORGANISM: Artificial Sequence
<220> FEATURE:
<223> OTHER INFORMATION: synthetic
```

<400> SEQUENCE: 195 cagcaattttt atactgttcc cact                                              24

<210> SEQ ID NO 196
<211> LENGTH: 8
<212> TYPE: PRT
<213> ORGANISM: Artificial Sequence
<220> FEATURE:
<223> OTHER INFORMATION: synthetic

<400> SEQUENCE: 196

Gln Gln Phe Tyr Thr Val Pro Thr
1               5

<210> SEQ ID NO 197
<211> LENGTH: 357
<212> TYPE: DNA
<213> ORGANISM: Artificial Sequence
<220> FEATURE:
<223> OTHER INFORMATION: synthetic

<400> SEQUENCE: 197
caggtgcagc tggtggagtc tgggggaggc gtggtccagc ctggggaggtc cctgagactc        60 tcctgtgtag cctctggatt caccttcagg aactatgaca tgcactgggt ccgccaggct       120
cctggcaagg ggctggaatg ggtggcagtt acatcatctg atggacttaa taaattctat       180
tcagactccg tgaagggccg attcaccatc tccagagaca attccaagaa cacgctgtct       240
ctgcaaatta ccggcctgag agctgaggac acggctgtgt attactgtgc gaaagagtcc       300
attttagcag ccctctttga ctactggggc caggaaccc tggtcaccgt ctcctca          357

<210> SEQ ID NO 198
<211> LENGTH: 119
<212> TYPE: PRT
<213> ORGANISM: Artificial Sequence
<220> FEATURE:
<223> OTHER INFORMATION: synthetic

<400> SEQUENCE: 198

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Arg Asn Tyr
            20                  25                  30

Asp Met His Trp Val Arg Gln Ala Pro Gly Lys Gly Leu Glu Trp Val
        35                  40                  45

Ala Val Thr Ser Ser Asp Gly Leu Asn Lys Phe Tyr Ser Asp Ser Val
    50                  55                  60

Lys Gly Arg Phe Thr Ile Ser Arg Asp Asn Lys Asn Thr Leu Ser
65                  70                  75                  80

Leu Gln Ile Thr Gly Leu Arg Ala Glu Asp Thr Ala Val Tyr Tyr Cys
                85                  90                  95

Ala Lys Glu Ser Ile Leu Ala Ala Leu Phe Asp Tyr Trp Gly Gln Gly
            100                 105                 110

Thr Leu Val Thr Val Ser Ser
        115

<210> SEQ ID NO 199
<211> LENGTH: 24
<212> TYPE: DNA
<213> ORGANISM: Artificial Sequence

```
<220> FEATURE:
<223> OTHER INFORMATION: synthetic

<400> SEQUENCE: 199
ggattcacct tcaggaacta tgac                                              24

<210> SEQ ID NO 200
<211> LENGTH: 8
<212> TYPE: PRT
<213> ORGANISM: Artificial Sequence
<220> FEATURE:
<223> OTHER INFORMATION: synthetic

<400> SEQUENCE: 200

Gly Phe Thr Phe Arg Asn Tyr Asp
1               5

<210> SEQ ID NO 201
<211> LENGTH: 24
<212> TYPE: DNA
<213> ORGANISM: Artificial Sequence
<220> FEATURE:
<223> OTHER INFORMATION: synthetic

<400> SEQUENCE: 201
acatcatctg atggacttaa taaa                                              24

<210> SEQ ID NO 202
<211> LENGTH: 8
<212> TYPE: PRT
<213> ORGANISM: Artificial Sequence
<220> FEATURE:
<223> OTHER INFORMATION: synthetic

<400> SEQUENCE: 202

Thr Ser Ser Asp Gly Leu Asn Lys
1               5

<210> SEQ ID NO 203
<211> LENGTH: 36
<212> TYPE: DNA
<213> ORGANISM: Artificial Sequence
<220> FEATURE:
<223> OTHER INFORMATION: synthetic

<400> SEQUENCE: 203
gcgaaagagt ccattttagc agccctcttt gactac                                 36

<210> SEQ ID NO 204
<211> LENGTH: 12
<212> TYPE: PRT
<213> ORGANISM: Artificial Sequence
<220> FEATURE:
<223> OTHER INFORMATION: synthetic

<400> SEQUENCE: 204

Ala Lys Glu Ser Ile Leu Ala Ala Leu Phe Asp Tyr
1               5                   10

<210> SEQ ID NO 205
<211> LENGTH: 336
<212> TYPE: DNA
<213> ORGANISM: Artificial Sequence
<220> FEATURE:
<223> OTHER INFORMATION: synthetic

<400> SEQUENCE: 205
```

```
gacatcgtga tgacccagtc tccagactcc ctggctgtgt ctctgggcga gagggccacc      60
atcaactgca agtccagcca gagtgtttta tacagctcca acaataagaa ctacttggct     120
tggtaccagc agaaaccagg acagcctcct aagctgctct tttactgggc atctacccgg     180
gaatccgggg tccctgaccg attcagtggc agcgggtctg ggacagattt cactctcacc     240
atcagcagcc tgcaggctga agatgtggca gtttattact gtcagcaaca ttatactact     300 cccactttg gccaggggac caagctggag atcaaa                                336
```

<210> SEQ ID NO 206
<211> LENGTH: 112
<212> TYPE: PRT
<213> ORGANISM: Artificial Sequence
<220> FEATURE:
<223> OTHER INFORMATION: synthetic

<400> SEQUENCE: 206

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Phe Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Thr Thr Pro Thr Phe Gly Gln Gly Thr Lys Leu Glu Ile Lys
            100                 105                 110
```

<210> SEQ ID NO 207
<211> LENGTH: 36
<212> TYPE: DNA
<213> ORGANISM: Artificial Sequence
<220> FEATURE:
<223> OTHER INFORMATION: synthetic

<400> SEQUENCE: 207

```
cagagtgttt tatacagctc caacaataag aactac                                36
```

<210> SEQ ID NO 208
<211> LENGTH: 12
<212> TYPE: PRT
<213> ORGANISM: Artificial Sequence
<220> FEATURE:
<223> OTHER INFORMATION: synthetic

<400> SEQUENCE: 208

```
Gln Ser Val Leu Tyr Ser Ser Asn Asn Lys Asn Tyr
1               5                   10
```

<210> SEQ ID NO 209
<211> LENGTH: 9
<212> TYPE: DNA
<213> ORGANISM: Artificial Sequence
<220> FEATURE:
<223> OTHER INFORMATION: synthetic

<400> SEQUENCE: 209 tgggcatct                                                              9

<210> SEQ ID NO 210
<211> LENGTH: 3
<212> TYPE: PRT
<213> ORGANISM: Artificial Sequence
<220> FEATURE:
<223> OTHER INFORMATION: synthetic

<400> SEQUENCE: 210

Trp Ala Ser
1

<210> SEQ ID NO 211
<211> LENGTH: 24
<212> TYPE: DNA
<213> ORGANISM: Artificial Sequence
<220> FEATURE:
<223> OTHER INFORMATION: synthetic

<400> SEQUENCE: 211
cagcaacatt atactactcc cact                                             24

<210> SEQ ID NO 212
<211> LENGTH: 8
<212> TYPE: PRT
<213> ORGANISM: Artificial Sequence
<220> FEATURE:
<223> OTHER INFORMATION: synthetic

<400> SEQUENCE: 212

Gln Gln His Tyr Thr Thr Pro Thr
1               5

<210> SEQ ID NO 213
<211> LENGTH: 357
<212> TYPE: DNA
<213> ORGANISM: Artificial Sequence
<220> FEATURE:
<223> OTHER INFORMATION: synthetic

<400> SEQUENCE: 213
caggtgcagc tggtggagtc tgggggaggc gtggtccagc ctgggaggtc cctgagactc      60
tcctgtgcag cctctggatt caccttcagt agctatggca tgcactgggt ccgccagact     120
ccgggcaagg ggctggagtg ggtggcattt atatcatatg atggaaataa taatactat      180 gcagactccg tgaagggccg attcaccatc tccagagaca attccaagaa cacgctgttt     240
ctgcaaatga acagcctgag agctgaggac acggctgtgt attactgtgc gaaagagtcc     300
attttagcag ccctctttga ctactggggc cagggaaccc tggtcaccgt ctcctca        357

<210> SEQ ID NO 214
<211> LENGTH: 119
<212> TYPE: PRT
<213> ORGANISM: Artificial Sequence
<220> FEATURE:
<223> OTHER INFORMATION: synthetic

<400> SEQUENCE: 214

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Thr Pro Gly Lys Gly Leu Glu Trp Val 35                  40                  45
Ala Phe Ile Ser Tyr Asp Gly Asn Asn Lys Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Lys Glu Ser Ile Leu Ala Ala Leu Phe Asp Tyr Trp Gly Gln Gly
            100                 105                 110

Thr Leu Val Thr Val Ser Ser
        115

<210> SEQ ID NO 215
<211> LENGTH: 24
<212> TYPE: DNA
<213> ORGANISM: Artificial Sequence
<220> FEATURE:
<223> OTHER INFORMATION: synthetic

<400> SEQUENCE: 215
ggattcacct tcagtagcta tggc                                         24

<210> SEQ ID NO 216
<211> LENGTH: 8
<212> TYPE: PRT
<213> ORGANISM: Artificial Sequence
<220> FEATURE:
<223> OTHER INFORMATION: synthetic

<400> SEQUENCE: 216

Gly Phe Thr Phe Ser Ser Tyr Gly
1               5

<210> SEQ ID NO 217
<211> LENGTH: 24
<212> TYPE: DNA
<213> ORGANISM: Artificial Sequence
<220> FEATURE:
<223> OTHER INFORMATION: synthetic

<400> SEQUENCE: 217
atatcatatg atggaaataa taaa                                         24

<210> SEQ ID NO 218
<211> LENGTH: 8
<212> TYPE: PRT
<213> ORGANISM: Artificial Sequence
<220> FEATURE:
<223> OTHER INFORMATION: synthetic

<400> SEQUENCE: 218

Ile Ser Tyr Asp Gly Asn Asn Lys
1               5

<210> SEQ ID NO 219
<211> LENGTH: 36
<212> TYPE: DNA
<213> ORGANISM: Artificial Sequence
<220> FEATURE:
<223> OTHER INFORMATION: synthetic

<400> SEQUENCE: 219
gcgaaagagt ccattttagc agccctcttt gactac                            36

```
<210> SEQ ID NO 220
<211> LENGTH: 12
<212> TYPE: PRT
<213> ORGANISM: Artificial Sequence
<220> FEATURE:
<223> OTHER INFORMATION: synthetic

<400> SEQUENCE: 220

Ala Lys Glu Ser Ile Leu Ala Ala Leu Phe Asp Tyr
1               5                   10

<210> SEQ ID NO 221
<211> LENGTH: 336
<212> TYPE: DNA
<213> ORGANISM: Artificial Sequence
<220> FEATURE:
<223> OTHER INFORMATION: synthetic

<400> SEQUENCE: 221
gacatcgtga tgacccagtc tccagactcc ctggctgtgt ctctgggcga gagggccacc    60
atcaactgca agtccagcca gagtgtttta tacagctcca acaataagaa ctacttagct   120
tggtaccagc agaaacctgg acagcctcct aagctgctca tttactgggc atctacccgg   180
gaatccgggg tccctgaccg attcagtggc agcgggtctg ggacagattt cactctcacc   240
atcagcagcc tgcaggctga agatgtggca ctttattact gtcaacaata ttataatact   300 cccactttg gccaggggac caagctggag atcaaa                              336

<210> SEQ ID NO 222
<211> LENGTH: 112
<212> TYPE: PRT
<213> ORGANISM: Artificial Sequence
<220> FEATURE:
<223> OTHER INFORMATION: synthetic

<400> SEQUENCE: 222

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Leu Tyr Tyr Cys Gln Gln
                85                  90                  95

Tyr Tyr Asn Thr Pro Thr Phe Gly Gln Gly Thr Lys Leu Glu Ile Lys
            100                 105                 110

<210> SEQ ID NO 223
<211> LENGTH: 36
<212> TYPE: DNA
<213> ORGANISM: Artificial Sequence
<220> FEATURE:
<223> OTHER INFORMATION: synthetic

<400> SEQUENCE: 223
cagagtgttt tatacagctc caacaataag aactac                              36
```

<210> SEQ ID NO 224
<211> LENGTH: 12
<212> TYPE: PRT
<213> ORGANISM: Artificial Sequence
<220> FEATURE:
<223> OTHER INFORMATION: synthetic

<400> SEQUENCE: 224

Gln Ser Val Leu Tyr Ser Ser Asn Asn Lys Asn Tyr
1               5                   10

<210> SEQ ID NO 225
<211> LENGTH: 9
<212> TYPE: DNA
<213> ORGANISM: Artificial Sequence
<220> FEATURE:
<223> OTHER INFORMATION: synthetic

<400> SEQUENCE: 225 tgggcatct                                                                9

<210> SEQ ID NO 226
<211> LENGTH: 3
<212> TYPE: PRT
<213> ORGANISM: Artificial Sequence
<220> FEATURE:
<223> OTHER INFORMATION: synthetic

<400> SEQUENCE: 226

Trp Ala Ser
1

<210> SEQ ID NO 227
<211> LENGTH: 24
<212> TYPE: DNA
<213> ORGANISM: Artificial Sequence
<220> FEATURE:
<223> OTHER INFORMATION: synthetic

<400> SEQUENCE: 227
caacaatatt ataatactcc cact                                              24

<210> SEQ ID NO 228
<211> LENGTH: 8
<212> TYPE: PRT
<213> ORGANISM: Artificial Sequence
<220> FEATURE:
<223> OTHER INFORMATION: synthetic

<400> SEQUENCE: 228

Gln Gln Tyr Tyr Asn Thr Pro Thr
1               5

<210> SEQ ID NO 229
<211> LENGTH: 357
<212> TYPE: DNA
<213> ORGANISM: Artificial Sequence
<220> FEATURE:
<223> OTHER INFORMATION: synthetic

<400> SEQUENCE: 229
caggtgcagc tggtggagtc tgggggaggc gtggtccagc ctgggaggtc cctgagactc        60
tcctgtgcag cctctggatt caccttcagt agctatggca tgcactgggt ccgccaggct       120
ccagtcaagg ggctggagtg gtggcattt atatcatatg atggaagtaa taaatactat        180
gcagactccg tgaagggccg attcaccatc tccagagaca attccaagaa cacgctgtat       240

```
ctccaaatga acagcctgac agctgaggac acggctgttt attactgtgc gaaagagtcc    300
attttagcag ccctctttga ctactggggc cagggaaccc tggtcaccgt ctcctca      357
```

<210> SEQ ID NO 230
<211> LENGTH: 119
<212> TYPE: PRT
<213> ORGANISM: Artificial Sequence
<220> FEATURE:
<223> OTHER INFORMATION: synthetic

<400> SEQUENCE: 230

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Val Lys Gly Leu Glu Trp Val
        35                  40                  45

Ala Phe Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Thr Ala Glu Asp Thr Ala Val Tyr Tyr Cys
                85                  90                  95

Ala Lys Glu Ser Ile Leu Ala Ala Leu Phe Asp Tyr Trp Gly Gln Gly
            100                 105                 110

Thr Leu Val Thr Val Ser Ser
        115
```

<210> SEQ ID NO 231
<211> LENGTH: 24
<212> TYPE: DNA
<213> ORGANISM: Artificial Sequence
<220> FEATURE:
<223> OTHER INFORMATION: synthetic

<400> SEQUENCE: 231

```
ggattcacct tcagtagcta tggc                                          24
```

<210> SEQ ID NO 232
<211> LENGTH: 8
<212> TYPE: PRT
<213> ORGANISM: Artificial Sequence
<220> FEATURE:
<223> OTHER INFORMATION: synthetic

<400> SEQUENCE: 232

```
Gly Phe Thr Phe Ser Ser Tyr Gly
1               5
```

<210> SEQ ID NO 233
<211> LENGTH: 24
<212> TYPE: DNA
<213> ORGANISM: Artificial Sequence
<220> FEATURE:
<223> OTHER INFORMATION: synthetic

<400> SEQUENCE: 233

```
atatcatatg atggaagtaa taaa                                          24
```

<210> SEQ ID NO 234
<211> LENGTH: 8

-continued

<212> TYPE: PRT
<213> ORGANISM: Artificial Sequence
<220> FEATURE:
<223> OTHER INFORMATION: synthetic

<400> SEQUENCE: 234

Ile Ser Tyr Asp Gly Ser Asn Lys
1               5

<210> SEQ ID NO 235
<211> LENGTH: 36
<212> TYPE: DNA
<213> ORGANISM: Artificial Sequence
<220> FEATURE:
<223> OTHER INFORMATION: synthetic

<400> SEQUENCE: 235
gcgaaagagt ccattttagc agccctcttt gactac                                36

<210> SEQ ID NO 236
<211> LENGTH: 12
<212> TYPE: PRT
<213> ORGANISM: Artificial Sequence
<220> FEATURE:
<223> OTHER INFORMATION: synthetic

<400> SEQUENCE: 236

Ala Lys Glu Ser Ile Leu Ala Ala Leu Phe Asp Tyr
1               5                   10

<210> SEQ ID NO 237
<211> LENGTH: 336
<212> TYPE: DNA
<213> ORGANISM: Artificial Sequence
<220> FEATURE:
<223> OTHER INFORMATION: synthetic

<400> SEQUENCE: 237
gacatcgtga tgacccagtc tccagactcc ctggctgtgt ctctgggcga gagggccacc        60
atcaactgca gtccagcca gagtgtttta tacagttcca acaataagaa ctacttagct        120
tggtaccagc agaaaccaag acagcctcct aagctgctca tttactgggc atctattcgg       180
gaatccgggg tccctgaccg attcagtggc agcgggtctg ggacagattt cattctcacc       240
atcagcagcc tgcaggctga agatgtggca gtttattact gtcagcaatt ttatagtatt       300
cccacttttg gccaggggac caagctggag atcaaa                                 336

<210> SEQ ID NO 238
<211> LENGTH: 112
<212> TYPE: PRT
<213> ORGANISM: Artificial Sequence
<220> FEATURE:
<223> OTHER INFORMATION: synthetic

<400> SEQUENCE: 238

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Arg Gln
        35                  40                  45

Pro Pro Lys Leu Leu Ile Tyr Trp Ala Ser Ile Arg Glu Ser Gly Val
    50                  55                  60

Pro Asp Arg Phe Ser Gly Ser Gly Ser Gly Thr Asp Phe Ile Leu Thr
65                  70                  75                  80

Ile Ser Ser Leu Gln Ala Glu Asp Val Ala Val Tyr Tyr Cys Gln Gln
                85                  90                  95

Phe Tyr Ser Ile Pro Thr Phe Gly Gln Gly Thr Lys Leu Glu Ile Lys
            100                 105                 110

<210> SEQ ID NO 239
<211> LENGTH: 36
<212> TYPE: DNA
<213> ORGANISM: Artificial Sequence
<220> FEATURE:
<223> OTHER INFORMATION: synthetic

<400> SEQUENCE: 239
cagagtgttt tatacagttc aacaataag aactac                                  36

<210> SEQ ID NO 240
<211> LENGTH: 12
<212> TYPE: PRT
<213> ORGANISM: Artificial Sequence
<220> FEATURE:
<223> OTHER INFORMATION: synthetic

<400> SEQUENCE: 240

Gln Ser Val Leu Tyr Ser Ser Asn Asn Lys Asn Tyr
1               5                   10

<210> SEQ ID NO 241
<211> LENGTH: 9
<212> TYPE: DNA
<213> ORGANISM: Artificial Sequence
<220> FEATURE:
<223> OTHER INFORMATION: synthetic

<400> SEQUENCE: 241 tgggcatct                                                               9

<210> SEQ ID NO 242
<211> LENGTH: 3
<212> TYPE: PRT
<213> ORGANISM: Artificial Sequence
<220> FEATURE:
<223> OTHER INFORMATION: synthetic

<400> SEQUENCE: 242

Trp Ala Ser
1

<210> SEQ ID NO 243
<211> LENGTH: 24
<212> TYPE: DNA
<213> ORGANISM: Artificial Sequence
<220> FEATURE:
<223> OTHER INFORMATION: synthetic

<400> SEQUENCE: 243
cagcaatttt atagtattcc cact                                              24

<210> SEQ ID NO 244
<211> LENGTH: 8
<212> TYPE: PRT
<213> ORGANISM: Artificial Sequence
<220> FEATURE:
<223> OTHER INFORMATION: synthetic

<400> SEQUENCE: 244

Gln Gln Phe Tyr Ser Ile Pro Thr
1               5

<210> SEQ ID NO 245
<211> LENGTH: 357
<212> TYPE: DNA
<213> ORGANISM: Artificial Sequence
<220> FEATURE:
<223> OTHER INFORMATION: synthetic

<400> SEQUENCE: 245
caggtgcagc tggtggagtc tgggggaggc gtggtccagc ctgggaggtc cctgagactc      60
tcctgtgcag cctctggatt cacctttagt agctatggca tgcactgggt ccgccaggct     120
ccagtcaagg ggctggagtg gtggcattt atatcaaatg ataaaagtaa taaatattat      180
gcagactcct tgaagggccg attcaccatc tccagagaca attccaagaa cacgctgtat     240
ctgcaaatga acagcctgac agctgaagac acggctgttt attactgtgc gaaagagtcc     300
attttagcag ccctctttga ctattggggc cagggaaccc tggtcaccgt ctcctca       357

<210> SEQ ID NO 246
<211> LENGTH: 119
<212> TYPE: PRT
<213> ORGANISM: Artificial Sequence
<220> FEATURE:
<223> OTHER INFORMATION: synthetic

<400> SEQUENCE: 246

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Val Lys Gly Leu Glu Trp Val
        35                  40                  45

Ala Phe Ile Ser Asn Asp Lys Ser Asn Lys Tyr Tyr Ala Asp Ser Leu
    50                  55                  60

Lys Gly Arg Phe Thr Ile Ser Arg Asp Asn Ser Lys Asn Thr Leu Tyr
65                  70                  75                  80

Leu Gln Met Asn Ser Leu Thr Ala Glu Asp Thr Ala Val Tyr Tyr Cys
                85                  90                  95

Ala Lys Glu Ser Ile Leu Ala Ala Leu Phe Asp Tyr Trp Gly Gln Gly
            100                 105                 110

Thr Leu Val Thr Val Ser Ser
        115

<210> SEQ ID NO 247
<211> LENGTH: 24
<212> TYPE: DNA
<213> ORGANISM: Artificial Sequence
<220> FEATURE:
<223> OTHER INFORMATION: synthetic

<400> SEQUENCE: 247
ggattcacct ttagtagcta tggc                                              24

<210> SEQ ID NO 248
<211> LENGTH: 8
<212> TYPE: PRT
<213> ORGANISM: Artificial Sequence
<220> FEATURE:

<223> OTHER INFORMATION: synthetic

<400> SEQUENCE: 248

Gly Phe Thr Phe Ser Ser Tyr Gly
1               5

<210> SEQ ID NO 249
<211> LENGTH: 24
<212> TYPE: DNA
<213> ORGANISM: Artificial Sequence
<220> FEATURE:
<223> OTHER INFORMATION: synthetic

<400> SEQUENCE: 249
atatcaaatg ataaaagtaa taaa                                          24

<210> SEQ ID NO 250
<211> LENGTH: 8
<212> TYPE: PRT
<213> ORGANISM: Artificial Sequence
<220> FEATURE:
<223> OTHER INFORMATION: synthetic

<400> SEQUENCE: 250

Ile Ser Asn Asp Lys Ser Asn Lys
1               5

<210> SEQ ID NO 251
<211> LENGTH: 36
<212> TYPE: DNA
<213> ORGANISM: Artificial Sequence
<220> FEATURE:
<223> OTHER INFORMATION: synthetic

<400> SEQUENCE: 251
gcgaaagagt ccattttagc agccctcttt gactat                             36

<210> SEQ ID NO 252
<211> LENGTH: 12
<212> TYPE: PRT
<213> ORGANISM: Artificial Sequence
<220> FEATURE:
<223> OTHER INFORMATION: synthetic

<400> SEQUENCE: 252

Ala Lys Glu Ser Ile Leu Ala Ala Leu Phe Asp Tyr
1               5                   10

<210> SEQ ID NO 253
<211> LENGTH: 336
<212> TYPE: DNA
<213> ORGANISM: Artificial Sequence
<220> FEATURE:
<223> OTHER INFORMATION: synthetic

<400> SEQUENCE: 253
gacatcgtga tgacccagtc tccagactcc ctggctgtgt ctctgggcga gagggccacc    60
atcaactgca agtccagcca gagtgtttta tacagctcca acaataagaa ctacttagct   120
tggtaccagc agaaaccaag acagcctcct aagctactca tttactgggc atctattcgg   180
gaatccgggg tccctgaccg attcagtggc agcgggtctg ggacagattt cactctcacc   240
atcagcagcc tgcaggctga agatgtggca gtttattact gtcaacaatt ttatagtgtt   300
cccacttttg gccaggggac caagctggag atcaaa                             336

<210> SEQ ID NO 254
<211> LENGTH: 112
<212> TYPE: PRT
<213> ORGANISM: Artificial Sequence
<220> FEATURE:
<223> OTHER INFORMATION: synthetic

<400> SEQUENCE: 254

```
Asp Ile Val Met Thr Gln Ser Pro Asp Ser Leu Ala Val Ser Leu Gly
1               5                   10                  15
Glu Arg Ala Thr Ile Asn Cys Lys Ser Gln Ser Val Leu Tyr Ser
            20                  25                  30
Ser Asn Asn Lys Asn Tyr Leu Ala Trp Tyr Gln Lys Pro Arg Gln
        35                  40                  45
Pro Pro Lys Leu Leu Ile Tyr Trp Ala Ser Ile Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Phe Tyr Ser Val Pro Thr Phe Gly Gln Gly Thr Lys Leu Glu Ile Lys
            100                 105                 110
```

<210> SEQ ID NO 255
<211> LENGTH: 36
<212> TYPE: DNA
<213> ORGANISM: Artificial Sequence
<220> FEATURE:
<223> OTHER INFORMATION: synthetic

<400> SEQUENCE: 255
cagagtgttt tatacagctc caacaataag aactac                     36

<210> SEQ ID NO 256
<211> LENGTH: 12
<212> TYPE: PRT
<213> ORGANISM: Artificial Sequence
<220> FEATURE:
<223> OTHER INFORMATION: synthetic

<400> SEQUENCE: 256

```
Gln Ser Val Leu Tyr Ser Ser Asn Asn Lys Asn Tyr
1               5                   10
```

<210> SEQ ID NO 257
<211> LENGTH: 9
<212> TYPE: DNA
<213> ORGANISM: Artificial Sequence
<220> FEATURE:
<223> OTHER INFORMATION: synthetic

<400> SEQUENCE: 257 tgggcatct                                                    9

<210> SEQ ID NO 258
<211> LENGTH: 3
<212> TYPE: PRT
<213> ORGANISM: Artificial Sequence
<220> FEATURE:
<223> OTHER INFORMATION: synthetic

<400> SEQUENCE: 258

Trp Ala Ser

<210> SEQ ID NO 259
<211> LENGTH: 24
<212> TYPE: DNA
<213> ORGANISM: Artificial Sequence
<220> FEATURE:
<223> OTHER INFORMATION: synthetic

<400> SEQUENCE: 259 caacaattt atagtgttcc cact                                              24

<210> SEQ ID NO 260
<211> LENGTH: 8
<212> TYPE: PRT
<213> ORGANISM: Artificial Sequence
<220> FEATURE:
<223> OTHER INFORMATION: synthetic

<400> SEQUENCE: 260

Gln Gln Phe Tyr Ser Val Pro Thr
1               5

<210> SEQ ID NO 261
<211> LENGTH: 357
<212> TYPE: DNA
<213> ORGANISM: Artificial Sequence
<220> FEATURE:
<223> OTHER INFORMATION: synthetic

<400> SEQUENCE: 261
caggtgcagc tggtggagtc tgggggaggc gtggtccagc ctggggaggtc cctgagactc      60 tcctgtgcag cctctggatt caccttcagt agctatggca tgcactgggt ccgccaggct     120
ccagtcaagg ggctggagtg ggtggcattt atatcatttg atggaagtaa taaatactat     180
acagactccg tgaagggccg attcaccatc tccagagaca attccaagaa cacgctgtat     240
ctccaaatga acagcctgac agctgaggac acggctattt attactgtgc gaaagagtcc     300
attttagcag ccctctttga ctactggggc cagggaaccc tggtcactgt ctcctca        357

<210> SEQ ID NO 262
<211> LENGTH: 119
<212> TYPE: PRT
<213> ORGANISM: Artificial Sequence
<220> FEATURE:
<223> OTHER INFORMATION: synthetic

<400> SEQUENCE: 262

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Val Lys Gly Leu Glu Trp Val
        35                  40                  45

Ala Phe Ile Ser Phe Asp Gly Ser Asn Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Thr Ala Glu Asp Thr Ala Ile Tyr Tyr Cys
                85                  90                  95

Ala Lys Glu Ser Ile Leu Ala Ala Leu Phe Asp Tyr Trp Gly Gln Gly
            100                 105                 110

Thr Leu Val Thr Val Ser Ser
        115

<210> SEQ ID NO 263
<211> LENGTH: 24
<212> TYPE: DNA
<213> ORGANISM: Artificial Sequence
<220> FEATURE:
<223> OTHER INFORMATION: synthetic

<400> SEQUENCE: 263
ggattcacct tcagtagcta tggc                                          24

<210> SEQ ID NO 264
<211> LENGTH: 8
<212> TYPE: PRT
<213> ORGANISM: Artificial Sequence
<220> FEATURE:
<223> OTHER INFORMATION: synthetic

<400> SEQUENCE: 264

Gly Phe Thr Phe Ser Ser Tyr Gly
1               5

<210> SEQ ID NO 265
<211> LENGTH: 24
<212> TYPE: DNA
<213> ORGANISM: Artificial Sequence
<220> FEATURE:
<223> OTHER INFORMATION: synthetic

<400> SEQUENCE: 265
atatcatttg atggaagtaa taaa                                          24

<210> SEQ ID NO 266
<211> LENGTH: 8
<212> TYPE: PRT
<213> ORGANISM: Artificial Sequence
<220> FEATURE:
<223> OTHER INFORMATION: synthetic

<400> SEQUENCE: 266

Ile Ser Phe Asp Gly Ser Asn Lys
1               5

<210> SEQ ID NO 267
<211> LENGTH: 36
<212> TYPE: DNA
<213> ORGANISM: Artificial Sequence
<220> FEATURE:
<223> OTHER INFORMATION: synthetic

<400> SEQUENCE: 267
gcgaaagagt ccattttagc agccctcttt gactac                             36

<210> SEQ ID NO 268
<211> LENGTH: 12
<212> TYPE: PRT
<213> ORGANISM: Artificial Sequence
<220> FEATURE:
<223> OTHER INFORMATION: synthetic

<400> SEQUENCE: 268

Ala Lys Glu Ser Ile Leu Ala Ala Leu Phe Asp Tyr
1               5                   10

<210> SEQ ID NO 269
<211> LENGTH: 336
<212> TYPE: DNA
<213> ORGANISM: Artificial Sequence
<220> FEATURE:
<223> OTHER INFORMATION: synthetic

<400> SEQUENCE: 269

```
gacatcgtga tgacccagtc tccagactcc ctggctgtgt ctctgggcga gagggccacc    60
atcaactgca agtccagcca gagtgtttta tacagctcca acaataagaa ctacttagct   120
tggtaccagc agaaaccaag acagcctcct aacctgctca tttactgggc atctattcgg   180
gaatccgggg tccctgaccg attcagtggc agcgggtctg ggacagattt cactctcacc   240
atcagcagcc tgcaggctga agatgtggca ttttattact gtcagcaatt ttatagtatt   300
cccactttg gccaggggac caagctggag atcaaa                             336
```

<210> SEQ ID NO 270
<211> LENGTH: 112
<212> TYPE: PRT
<213> ORGANISM: Artificial Sequence
<220> FEATURE:
<223> OTHER INFORMATION: synthetic

<400> SEQUENCE: 270

```
Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Tyr Ser
            20                  25                  30
Ser Asn Asn Lys Asn Tyr Leu Ala Trp Tyr Gln Gln Lys Pro Arg Gln
        35                  40                  45
Pro Pro Asn Leu Leu Ile Tyr Trp Ala Ser Ile Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Phe Tyr Tyr Cys Gln Gln
                85                  90                  95
Phe Tyr Ser Ile Pro Thr Phe Gly Gln Gly Thr Lys Leu Glu Ile Lys
            100                 105                 110
```

<210> SEQ ID NO 271
<211> LENGTH: 36
<212> TYPE: DNA
<213> ORGANISM: Artificial Sequence
<220> FEATURE:
<223> OTHER INFORMATION: synthetic

<400> SEQUENCE: 271

```
cagagtgttt tatacagctc caacaataag aactac                              36
```

<210> SEQ ID NO 272
<211> LENGTH: 12
<212> TYPE: PRT
<213> ORGANISM: Artificial Sequence
<220> FEATURE:
<223> OTHER INFORMATION: synthetic

<400> SEQUENCE: 272

```
Gln Ser Val Leu Tyr Ser Ser Asn Asn Lys Asn Tyr
1               5                   10
```

```
<210> SEQ ID NO 273
<211> LENGTH: 9
<212> TYPE: DNA
<213> ORGANISM: Artificial Sequence
<220> FEATURE:
<223> OTHER INFORMATION: synthetic

<400> SEQUENCE: 273 tgggcatct                                                                    9

<210> SEQ ID NO 274
<211> LENGTH: 3
<212> TYPE: PRT
<213> ORGANISM: Artificial Sequence
<220> FEATURE:
<223> OTHER INFORMATION: synthetic

<400> SEQUENCE: 274

Trp Ala Ser
1

<210> SEQ ID NO 275
<211> LENGTH: 24
<212> TYPE: DNA
<213> ORGANISM: Artificial Sequence
<220> FEATURE:
<223> OTHER INFORMATION: synthetic

<400> SEQUENCE: 275
cagcaatttt atagtattcc cact                                                  24

<210> SEQ ID NO 276
<211> LENGTH: 8
<212> TYPE: PRT
<213> ORGANISM: Artificial Sequence
<220> FEATURE:
<223> OTHER INFORMATION: synthetic

<400> SEQUENCE: 276

Gln Gln Phe Tyr Ser Ile Pro Thr
1               5

<210> SEQ ID NO 277
<211> LENGTH: 357
<212> TYPE: DNA
<213> ORGANISM: Artificial Sequence
<220> FEATURE:
<223> OTHER INFORMATION: synthetic

<400> SEQUENCE: 277
caggtgcagc tggtggagtc tgggggaggc gtggtccagc ctggggaggtc cctgagactc          60 tcctgtgcag cctctggatt cacctttagg acctatggca tgcactgggt ccgccaggct         120
ccagtcaagg ggctggagtg ggtggcattt atatcaaagg atggaagtga taaatactat         180
gtagactccg tgaagggccg attcaccatc tccagagaca attccaagaa cacgctgttt         240
ctgcaaatga acagcctgac agctgaggac acggctgttt attattgtgc gaaagagtcc         300
attttagcag ccctctttga ctactggggc cagggaaccc tggtcactgt ctcctca           357

<210> SEQ ID NO 278
<211> LENGTH: 119
<212> TYPE: PRT
<213> ORGANISM: Artificial Sequence
<220> FEATURE:
<223> OTHER INFORMATION: synthetic
```

<400> SEQUENCE: 278

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Arg Thr Tyr
            20                  25                  30

Gly Met His Trp Val Arg Gln Ala Pro Val Lys Gly Leu Glu Trp Val
        35                  40                  45

Ala Phe Ile Ser Lys Asp Gly Ser Asp Lys Tyr Val Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Thr Ala Glu Asp Thr Ala Val Tyr Tyr Cys
                85                  90                  95

Ala Lys Glu Ser Ile Leu Ala Ala Leu Phe Asp Tyr Trp Gly Gln Gly
            100                 105                 110

Thr Leu Val Thr Val Ser Ser
        115

<210> SEQ ID NO 279
<211> LENGTH: 24
<212> TYPE: DNA
<213> ORGANISM: Artificial Sequence
<220> FEATURE:
<223> OTHER INFORMATION: synthetic

<400> SEQUENCE: 279
ggattcacct ttaggaccta tggc                                    24

<210> SEQ ID NO 280
<211> LENGTH: 8
<212> TYPE: PRT
<213> ORGANISM: Artificial Sequence
<220> FEATURE:
<223> OTHER INFORMATION: synthetic

<400> SEQUENCE: 280

Gly Phe Thr Phe Arg Thr Tyr Gly
1               5

<210> SEQ ID NO 281
<211> LENGTH: 24
<212> TYPE: DNA
<213> ORGANISM: Artificial Sequence
<220> FEATURE:
<223> OTHER INFORMATION: synthetic

<400> SEQUENCE: 281
atatcaaagg atggaagtga taaa                                    24

<210> SEQ ID NO 282
<211> LENGTH: 8
<212> TYPE: PRT
<213> ORGANISM: Artificial Sequence
<220> FEATURE:
<223> OTHER INFORMATION: synthetic

<400> SEQUENCE: 282

Ile Ser Lys Asp Gly Ser Asp Lys
1               5

<210> SEQ ID NO 283
<211> LENGTH: 36

<212> TYPE: DNA
<213> ORGANISM: Artificial Sequence
<220> FEATURE:
<223> OTHER INFORMATION: synthetic

<400> SEQUENCE: 283
gcgaaagagt ccattttagc agccctcttt gactac                         36

<210> SEQ ID NO 284
<211> LENGTH: 12
<212> TYPE: PRT
<213> ORGANISM: Artificial Sequence
<220> FEATURE:
<223> OTHER INFORMATION: synthetic

<400> SEQUENCE: 284

Ala Lys Glu Ser Ile Leu Ala Ala Leu Phe Asp Tyr
1               5                   10

<210> SEQ ID NO 285
<211> LENGTH: 336
<212> TYPE: DNA
<213> ORGANISM: Artificial Sequence
<220> FEATURE:
<223> OTHER INFORMATION: synthetic

<400> SEQUENCE: 285
gacatcgtga tgacccagtc tccagactcc ctggctgtgt ctctgggcga gagggccacc    60
atcaactgca gtccagcca gagtgtttta tacagctcca acaataagaa ctacttagct   120
tggtaccagc agaaaccaag acagcctcct aaactcctca tttactgggc atctaatcgg   180
gaatccgggg tccctgaccg attcagtggc agcgggtctg ggacagattt cactctcacc   240
atcagcagcc tgcaggctga agatgtggca gtttattact gtcagcaatt ttatagtgtt   300
cccacttttg gccaggggac caagctggag atcaaa                            336

<210> SEQ ID NO 286
<211> LENGTH: 112
<212> TYPE: PRT
<213> ORGANISM: Artificial Sequence
<220> FEATURE:
<223> OTHER INFORMATION: synthetic

<400> SEQUENCE: 286

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Arg Gln
        35                  40                  45

Pro Pro Lys Leu Leu Ile Tyr Trp Ala Ser Asn Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Tyr Ser Val Pro Thr Phe Gly Gln Gly Thr Lys Leu Glu Ile Lys
            100                 105                 110

<210> SEQ ID NO 287
<211> LENGTH: 36
<212> TYPE: DNA

```
<213> ORGANISM: Artificial Sequence
<220> FEATURE:
<223> OTHER INFORMATION: synthetic

<400> SEQUENCE: 287
cagagtgttt tatacagctc caacaataag aactac                          36

<210> SEQ ID NO 288
<211> LENGTH: 12
<212> TYPE: PRT
<213> ORGANISM: Artificial Sequence
<220> FEATURE:
<223> OTHER INFORMATION: synthetic

<400> SEQUENCE: 288

Gln Ser Val Leu Tyr Ser Ser Asn Asn Lys Asn Tyr
1               5                   10

<210> SEQ ID NO 289
<211> LENGTH: 9
<212> TYPE: DNA
<213> ORGANISM: Artificial Sequence
<220> FEATURE:
<223> OTHER INFORMATION: synthetic

<400> SEQUENCE: 289 tgggcatct                                                         9

<210> SEQ ID NO 290
<211> LENGTH: 3
<212> TYPE: PRT
<213> ORGANISM: Artificial Sequence
<220> FEATURE:
<223> OTHER INFORMATION: synthetic

<400> SEQUENCE: 290

Trp Ala Ser
1

<210> SEQ ID NO 291
<211> LENGTH: 24
<212> TYPE: DNA
<213> ORGANISM: Artificial Sequence
<220> FEATURE:
<223> OTHER INFORMATION: synthetic

<400> SEQUENCE: 291
cagcaatttt atagtgttcc cact                                       24

<210> SEQ ID NO 292
<211> LENGTH: 8
<212> TYPE: PRT
<213> ORGANISM: Artificial Sequence
<220> FEATURE:
<223> OTHER INFORMATION: synthetic

<400> SEQUENCE: 292

Gln Gln Phe Tyr Ser Val Pro Thr
1               5

<210> SEQ ID NO 293
<211> LENGTH: 357
<212> TYPE: DNA
<213> ORGANISM: Artificial Sequence
<220> FEATURE:
<223> OTHER INFORMATION: synthetic
```

<400> SEQUENCE: 293

```
caggtgcagc tggtggagtc tgggggaggc gtggtccagc ctgggaggtc cctgagactc    60
tcctgtgcag cctctggatt cacctttagt agctatggca tgcactgggt ccgccaggct   120
ccagtcaagg gctggagtg gtggcattt atatcaaatg ataaaagtaa taaatactat    180
gcagactccg tgaagggccg attcaccatc tccagagaca attccaagaa cacgctgtat   240
ctgcaaatga acagcctgac agctgaggac acggctgttt attactgtgc gaaagagtcc   300
attttagcag ccctctttga ctcctggggc cagggaaccc tggtcaccgt ctcctca      357
```

<210> SEQ ID NO 294
<211> LENGTH: 119
<212> TYPE: PRT
<213> ORGANISM: Artificial Sequence
<220> FEATURE:
<223> OTHER INFORMATION: synthetic

<400> SEQUENCE: 294

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Val Lys Gly Leu Glu Trp Val
        35                  40                  45

Ala Phe Ile Ser Asn Asp Lys Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Thr Ala Glu Asp Thr Ala Val Tyr Tyr Cys
                85                  90                  95

Ala Lys Glu Ser Ile Leu Ala Ala Leu Phe Asp Ser Trp Gly Gln Gly
            100                 105                 110

Thr Leu Val Thr Val Ser Ser
        115
```

<210> SEQ ID NO 295
<211> LENGTH: 24
<212> TYPE: DNA
<213> ORGANISM: Artificial Sequence
<220> FEATURE:
<223> OTHER INFORMATION: synthetic

<400> SEQUENCE: 295

```
ggattcacct ttagtagcta tggc                                           24
```

<210> SEQ ID NO 296
<211> LENGTH: 8
<212> TYPE: PRT
<213> ORGANISM: Artificial Sequence
<220> FEATURE:
<223> OTHER INFORMATION: synthetic

<400> SEQUENCE: 296

```
Gly Phe Thr Phe Ser Ser Tyr Gly
1               5
```

<210> SEQ ID NO 297
<211> LENGTH: 24
<212> TYPE: DNA
<213> ORGANISM: Artificial Sequence
<220> FEATURE:

<223> OTHER INFORMATION: synthetic

<400> SEQUENCE: 297
atatcaaatg ataaaagtaa taaa                                              24

<210> SEQ ID NO 298
<211> LENGTH: 8
<212> TYPE: PRT
<213> ORGANISM: Artificial Sequence
<220> FEATURE:
<223> OTHER INFORMATION: synthetic

<400> SEQUENCE: 298

Ile Ser Asn Asp Lys Ser Asn Lys
1               5

<210> SEQ ID NO 299
<211> LENGTH: 36
<212> TYPE: DNA
<213> ORGANISM: Artificial Sequence
<220> FEATURE:
<223> OTHER INFORMATION: synthetic

<400> SEQUENCE: 299
gcgaaagagt ccattttagc agccctcttt gactcc                                 36

<210> SEQ ID NO 300
<211> LENGTH: 12
<212> TYPE: PRT
<213> ORGANISM: Artificial Sequence
<220> FEATURE:
<223> OTHER INFORMATION: synthetic

<400> SEQUENCE: 300

Ala Lys Glu Ser Ile Leu Ala Ala Leu Phe Asp Ser
1               5                   10

<210> SEQ ID NO 301
<211> LENGTH: 336
<212> TYPE: DNA
<213> ORGANISM: Artificial Sequence
<220> FEATURE:
<223> OTHER INFORMATION: synthetic

<400> SEQUENCE: 301
gacatcgtga tgacccagtc tccagactcc ctggctgtgt ctctgggcga gagggccacc       60
atcaactgca gtccagcca gagtgtttta tacagctcca acaataagaa ctacttagct       120
tggtaccagc agaaaccaag acagcctcct aagctgctca tttactgggc atctattcgg      180
gaatccgggg tccctgaccg attcagtggc agcgggtctg ggcagattt cactctcacc       240 atcagcagcc tgcaggctgc agatgtggca gtttattact gtcagcaatt ttatagtgtt      300 cccactttg gccaggggac caagctggag atcaaa                                  336

<210> SEQ ID NO 302
<211> LENGTH: 112
<212> TYPE: PRT
<213> ORGANISM: Artificial Sequence
<220> FEATURE:
<223> OTHER INFORMATION: synthetic

<400> SEQUENCE: 302

Asp Ile Val Met Thr Gln Ser Pro Asp Ser Leu Ala Val Ser Leu Gly
1               5                   10                  15

```
        Glu Arg Ala Thr Ile Asn Cys Lys Ser Ser Gln Ser Val Leu Tyr Ser
                     20                  25                  30

Ser Asn Asn Lys Asn Tyr Leu Ala Trp Tyr Gln Gln Lys Pro Arg Gln
                 35                  40                  45

Pro Pro Lys Leu Leu Ile Tyr Trp Ala Ser Ile Arg Glu Ser Gly Val
         50                  55                  60

Pro Asp Arg Phe Ser Gly Ser Gly Ser Gly Ala Asp Phe Thr Leu Thr
         65                  70                  75                  80

Ile Ser Ser Leu Gln Ala Ala Asp Val Ala Val Tyr Tyr Cys Gln Gln
                         85                  90                  95

Phe Tyr Ser Val Pro Thr Phe Gly Gln Gly Thr Lys Leu Glu Ile Lys
                    100                 105                 110

<210> SEQ ID NO 303
<211> LENGTH: 36
<212> TYPE: DNA
<213> ORGANISM: Artificial Sequence
<220> FEATURE:
<223> OTHER INFORMATION: synthetic

<400> SEQUENCE: 303
cagagtgttt tatacagctc caacaataag aactac                              36

<210> SEQ ID NO 304
<211> LENGTH: 12
<212> TYPE: PRT
<213> ORGANISM: Artificial Sequence
<220> FEATURE:
<223> OTHER INFORMATION: synthetic

<400> SEQUENCE: 304

Gln Ser Val Leu Tyr Ser Ser Asn Asn Lys Asn Tyr
 1               5                  10

<210> SEQ ID NO 305
<211> LENGTH: 9
<212> TYPE: DNA
<213> ORGANISM: Artificial Sequence
<220> FEATURE:
<223> OTHER INFORMATION: synthetic

<400> SEQUENCE: 305 tgggcatct                                                             9

<210> SEQ ID NO 306
<211> LENGTH: 3
<212> TYPE: PRT
<213> ORGANISM: Artificial Sequence
<220> FEATURE:
<223> OTHER INFORMATION: synthetic

<400> SEQUENCE: 306

Trp Ala Ser
 1

<210> SEQ ID NO 307
<211> LENGTH: 24
<212> TYPE: DNA
<213> ORGANISM: Artificial Sequence
<220> FEATURE:
<223> OTHER INFORMATION: synthetic

<400> SEQUENCE: 307
cagcaatttt atagtgttcc cact                                            24
```

```
<210> SEQ ID NO 308
<211> LENGTH: 8
<212> TYPE: PRT
<213> ORGANISM: Artificial Sequence
<220> FEATURE:
<223> OTHER INFORMATION: synthetic

<400> SEQUENCE: 308

Gln Gln Phe Tyr Ser Val Pro Thr
1               5
```